US009642997B2

(12) United States Patent
Ignon et al.

(10) Patent No.: US 9,642,997 B2
(45) Date of Patent: *May 9, 2017

(54) DEVICES FOR TREATING SKIN USING TREATMENT MATERIALS LOCATED ALONG A TIP

(71) Applicant: EDGE SYSTEMS LLC, Signal Hill, CA (US)

(72) Inventors: Roger Ignon, Redondo Beach, CA (US); Ed F. Nicolas, Wilmington, CA (US)

(73) Assignee: Edge Systems LLC, Signal Hill, CA (US)

( * ) Notice: Subject to any disclaimer, the term of this patent is extended or adjusted under 35 U.S.C. 154(b) by 23 days.

This patent is subject to a terminal disclaimer.

(21) Appl. No.: 14/455,762

(22) Filed: Aug. 8, 2014

(65) Prior Publication Data

US 2015/0032047 A1   Jan. 29, 2015

Related U.S. Application Data

(63) Continuation of application No. 12/832,663, filed on Jul. 8, 2010, now Pat. No. 8,814,836, which is a
(Continued)

(51) Int. Cl.
*A61M 35/00* (2006.01)
*A61B 17/54* (2006.01)
(Continued)

(52) U.S. Cl.
CPC .......... *A61M 35/003* (2013.01); *A61B 17/32* (2013.01); *A61B 17/54* (2013.01); *A61M 37/00* (2013.01);
(Continued)

(58) Field of Classification Search
CPC . A61M 35/00; A61F 7/00; A61H 1/00; A61H 19/00; A61H 23/00
(Continued)

(56) References Cited

U.S. PATENT DOCUMENTS 2,608,032 A   8/1952 Garver
2,631,583 A   3/1953 Lavergne
(Continued)

FOREIGN PATENT DOCUMENTS

DE   34 21 390 A1   12/1985
DE   234 608   4/1986
(Continued)

OTHER PUBLICATIONS

Ex Parte Reexamination Certificate U.S. Pat. No. 6,241,739 C1, Microdermabrasion Device and Method of Treating the Skin Surface, Inventor Stephen H. Waldron, Dec. 11, 2007, and file history through Aug. 8, 2006.
(Continued)

*Primary Examiner* — Michele M Kidwell
*Assistant Examiner* — Ilya Treyger
(74) *Attorney, Agent, or Firm* — Knobbe, Martens, Olson & Bear, LLP

(57) ABSTRACT

According to some embodiments, a microdermabrasion device for treating skin comprises a handpiece assembly having a distal end and a proximal end. The handpiece assembly includes at least one delivery conduit and at least one waste conduit. The microdermabrasion device additionally comprises a tip configured to be positioned along the distal end of the handpiece assembly, wherein the tip is adapted to contact skin surface. In several embodiments, the tip comprises a lip, a first opening in fluid communication with the fluid delivery conduit and a second opening in fluid communication with the waste conduit. In one embodiment,
(Continued)

the device includes one or more abrasive elements positioned along a distal end of the tip, wherein the abrasive elements are configured to selectively remove skin as the tip is moved relative to a skin surface.

20 Claims, 61 Drawing Sheets

Related U.S. Application Data continuation-in-part of application No. 12/362,353, filed on Jan. 29, 2009, now Pat. No. 9,056,193.

(60) Provisional application No. 61/024,504, filed on Jan. 29, 2008, provisional application No. 61/224,044, filed on Jul. 8, 2009, provisional application No. 61/229,674, filed on Jul. 29, 2009, provisional application No. 61/254,152, filed on Oct. 22, 2009.

(51) Int. Cl.
*A61M 37/00* (2006.01)
*A61H 1/00* (2006.01)
*A61B 17/00* (2006.01)
*A61B 17/30* (2006.01)
*A61B 17/32* (2006.01)

(52) U.S. Cl.
CPC ............ *A61B 2017/00084* (2013.01); *A61B 2017/00438* (2013.01); *A61B 2017/00893* (2013.01); *A61B 2017/306* (2013.01); *A61B 2017/320004* (2013.01); *A61B 2017/320064* (2013.01)

(58) Field of Classification Search
USPC ........................................ 604/289, 290, 291
See application file for complete search history.

(56) References Cited

U.S. PATENT DOCUMENTS

| | | | |
|---|---|---|---|
| 2,701,559 A | 2/1955 | Cooper | |
| 2,712,823 A | 7/1955 | Kurtin | |
| 2,867,214 A | 1/1959 | Wilson | |
| 2,881,763 A | 4/1959 | Robbins | |
| 2,921,585 A | 1/1960 | Schumann | |
| 3,085,573 A | 4/1963 | Meyer et al. | |
| 3,214,869 A | 11/1965 | Stryker | |
| 3,476,112 A | 11/1969 | Elstein | |
| 3,574,239 A | 4/1971 | Sollerud | |
| 3,715,838 A | 2/1973 | Young et al. | |
| 3,865,352 A | 2/1975 | Nelson et al. | |
| 3,948,265 A | 4/1976 | Al Ami | |
| 3,964,212 A | 6/1976 | Karden | |
| 3,977,084 A | 8/1976 | Sloan | |
| 4,121,388 A | 10/1978 | Wilson | |
| 4,155,721 A | 5/1979 | Fletcher | |
| 4,170,821 A | 10/1979 | Booth | |
| 4,182,329 A | 1/1980 | Smit et al. | |
| 4,203,431 A | 5/1980 | Abura et al. | |
| 4,216,233 A | 8/1980 | Stein | |
| 4,299,219 A | 11/1981 | Norris, Jr. | |
| 4,378,804 A | 4/1983 | Cortese | |
| 4,560,373 A | 12/1985 | Sugino et al. | |
| 4,646,480 A | 3/1987 | Williams | |
| 4,646,482 A | 3/1987 | Chitjian | |
| 4,655,743 A | 4/1987 | Hyde | |
| 4,676,749 A | 6/1987 | Mabille | |
| 4,706,676 A | 11/1987 | Peck | |
| 4,754,756 A | 7/1988 | Shelanski | |
| 4,757,814 A | 7/1988 | Wang et al. | |
| 4,764,362 A | 8/1988 | Barchas | |
| 4,795,421 A | 1/1989 | Blasius, Jr. et al. | |
| 4,875,287 A * | 10/1989 | Creasy et al. | 30/34.05 |
| 4,886,078 A | 12/1989 | Shiffman | |
| 4,887,994 A | 12/1989 | Bedford | |
| 4,900,316 A | 2/1990 | Yamamoto | |
| 4,917,086 A | 4/1990 | Feltovich et al. | |
| 4,925,450 A | 5/1990 | Imonti et al. | |
| 4,957,747 A | 9/1990 | Stiefel | |
| 5,006,004 A | 4/1991 | Dirksing et al. | |
| 5,006,339 A | 4/1991 | Bargery et al. | |
| 5,012,797 A | 5/1991 | Liang et al. | |
| 5,035,089 A | 7/1991 | Tillman et al. | |
| 5,037,431 A | 8/1991 | Summers et al. | |
| 5,037,432 A | 8/1991 | Molinari | |
| 5,100,412 A | 3/1992 | Rosso | |
| 5,100,424 A | 3/1992 | Jang | |
| 5,119,839 A | 6/1992 | Rudolph | |
| 5,122,153 A | 6/1992 | Harrel | |
| 5,207,234 A | 5/1993 | Rosso | |
| 5,222,956 A | 6/1993 | Waldron | |
| 5,242,433 A | 9/1993 | Smith et al. | |
| 5,254,109 A | 10/1993 | Smith et al. | |
| 5,368,581 A | 11/1994 | Smith et al. | |
| 5,391,151 A | 2/1995 | Wilmot | |
| 5,417,674 A | 5/1995 | Smith et al. | |
| 5,419,772 A | 5/1995 | Teitz et al. | |
| 5,460,620 A | 10/1995 | Smith et al. | |
| 5,470,323 A | 11/1995 | Smith et al. | |
| 5,484,427 A | 1/1996 | Gibbons | |
| 5,562,642 A | 10/1996 | Smith et al. | |
| 5,611,687 A | 3/1997 | Wagner | |
| 5,612,797 A | 3/1997 | Clarke | |
| 5,674,235 A | 10/1997 | Parisi | |
| 5,676,643 A | 10/1997 | Cann et al. | |
| 5,676,648 A | 10/1997 | Henley | |
| 5,683,971 A | 11/1997 | Rose et al. | |
| 5,697,920 A | 12/1997 | Gibbons | |
| 5,707,383 A | 1/1998 | Bays | |
| 5,713,785 A | 2/1998 | Nishio | |
| 5,735,833 A | 4/1998 | Olson | |
| 5,759,185 A | 6/1998 | Grinberg | |
| 5,779,519 A | 7/1998 | Oliver | |
| 5,800,446 A | 9/1998 | Banuchi | |
| 5,807,353 A | 9/1998 | Schmitz | |
| 5,810,842 A | 9/1998 | Di Fiore et al. | |
| 5,813,416 A | 9/1998 | Rudolph | |
| 5,817,050 A | 10/1998 | Klein | |
| 5,846,215 A | 12/1998 | Zygmont | |
| 5,848,998 A | 12/1998 | Marasco, Jr. | |
| 5,861,142 A * | 1/1999 | Schick | 424/61 |
| 5,873,881 A | 2/1999 | McEwen et al. | |
| 5,879,323 A | 3/1999 | Henley | |
| 5,882,201 A | 3/1999 | Salem | |
| 5,885,260 A | 3/1999 | Mehl, Sr. et al. | |
| 5,908,401 A | 6/1999 | Henley | |
| 5,919,152 A | 7/1999 | Zygmont | |
| 5,954,730 A | 9/1999 | Bernabei | |
| 5,971,999 A | 10/1999 | Naldoni | |
| 5,980,555 A | 11/1999 | Barbut et al. | |
| 6,019,749 A | 2/2000 | Fields et al. | |
| 6,024,733 A | 2/2000 | Eggers et al. | |
| 6,027,402 A | 2/2000 | Oliver | |
| 6,039,745 A | 3/2000 | Di Fiore et al. | |
| 6,042,552 A | 3/2000 | Cornier | |
| 6,080,165 A | 6/2000 | DeJacma | |
| 6,080,166 A | 6/2000 | McEwen et al. | |
| 6,090,085 A | 7/2000 | Mehl, Sr. et al. | |
| 6,120,512 A | 9/2000 | Bernabei | |
| 6,129,701 A | 10/2000 | Cimino | |
| 6,136,008 A | 10/2000 | Becker et al. | |
| 6,139,553 A | 10/2000 | Dotan | |
| 6,139,554 A | 10/2000 | Karkar et al. | |
| 6,142,155 A | 11/2000 | Rudolph | |
| 6,149,634 A | 11/2000 | Bernabei | |
| 6,159,226 A | 12/2000 | Kim | |
| 6,162,218 A | 12/2000 | Elbrecht et al. | |
| 6,162,232 A | 12/2000 | Shadduck | |
| 6,183,451 B1 | 2/2001 | Mehl, Sr. et al. | |
| 6,183,483 B1 | 2/2001 | Chang | |
| 6,193,589 B1 | 2/2001 | Khalaj | |

(56) References Cited

U.S. PATENT DOCUMENTS

| | | |
|---|---|---|
| 6,231,593 B1 | 5/2001 | Meserol |
| 6,235,039 B1 | 5/2001 | Parkin et al. |
| 6,238,275 B1 | 5/2001 | Metcalf et al. |
| 6,241,739 B1 | 6/2001 | Waldron |
| 6,264,666 B1 | 7/2001 | Coleman et al. |
| 6,277,128 B1 | 8/2001 | Muldner |
| 6,283,978 B1 | 9/2001 | Cheski et al. |
| 6,299,620 B1 | 10/2001 | Shadduck |
| 6,306,119 B1 | 10/2001 | Weber et al. |
| 6,306,147 B1 | 10/2001 | Bernabei et al. |
| 6,322,568 B1 | 11/2001 | Bernabei et al. |
| 6,368,333 B2 | 4/2002 | Bernabei et al. |
| 6,387,103 B2 | 5/2002 | Shadduck |
| 6,401,289 B1 | 6/2002 | Herbert |
| 6,409,736 B1 | 6/2002 | Bernabei |
| 6,410,599 B1 | 6/2002 | Johnson |
| RE37,796 E | 7/2002 | Henley |
| 6,414,032 B1 | 7/2002 | Johnson |
| 6,420,431 B1 | 7/2002 | Johnson |
| 6,423,078 B1 | 7/2002 | Bays et al. |
| 6,423,750 B1 | 7/2002 | Johnson |
| 6,432,113 B1 | 8/2002 | Parkin et al. |
| 6,432,114 B1 | 8/2002 | Rosso |
| 6,471,712 B2 | 10/2002 | Burres |
| 6,477,410 B1 | 11/2002 | Henley et al. |
| 6,482,212 B1 | 11/2002 | Bernabei et al. |
| 6,488,646 B1 | 12/2002 | Zygmont |
| 6,494,856 B1 | 12/2002 | Zygmont |
| 6,500,183 B1 | 12/2002 | Waldron |
| 6,503,256 B2 | 1/2003 | Parkin et al. |
| 6,511,486 B2 | 1/2003 | Mercier et al. |
| 6,514,262 B1 | 2/2003 | Di Fiore et al. |
| 6,527,783 B1* | 3/2003 | Ignon .................... 606/131 |
| 6,535,761 B2 | 3/2003 | Bernabei |
| 6,540,757 B1 | 4/2003 | Hruska et al. |
| 6,562,013 B1 | 5/2003 | Marasco, Jr. |
| 6,562,050 B1 | 5/2003 | Owen |
| 6,564,093 B1 | 5/2003 | Ostrow et al. |
| 6,565,535 B2 | 5/2003 | Zaias et al. |
| 6,582,442 B2 | 6/2003 | Simon et al. |
| 6,589,218 B2 | 7/2003 | Garcia |
| 6,592,595 B1 | 7/2003 | Mallett et al. |
| 6,629,983 B1 | 10/2003 | Ignon |
| 6,641,591 B1 | 11/2003 | Shadduck |
| 6,645,184 B1 | 11/2003 | Zelickson et al. |
| 6,652,888 B2 | 11/2003 | Rhoades |
| 6,673,081 B1 | 1/2004 | Tavger et al. |
| 6,673,082 B2 | 1/2004 | Mallett et al. |
| 6,685,853 B1 | 2/2004 | Angelopoulos et al. |
| 6,687,537 B2 | 2/2004 | Bernabei |
| 6,695,853 B2 | 2/2004 | Karasiuk |
| 6,735,470 B2 | 5/2004 | Henley et al. |
| 6,743,211 B1 | 6/2004 | Prausnitz et al. |
| 6,743,215 B2 | 6/2004 | Bernabei |
| 6,764,493 B1 | 7/2004 | Weber et al. |
| 6,869,611 B1 | 3/2005 | Kligman et al. |
| 6,905,487 B2 | 6/2005 | Zimmerman |
| 6,911,031 B2 | 6/2005 | Muldner |
| 6,924,649 B2 | 8/2005 | Knoedgen |
| 6,926,681 B1 | 8/2005 | Ramey et al. |
| 6,942,649 B2 | 9/2005 | Ignon et al. |
| 7,001,355 B2 | 2/2006 | Nunomura et al. |
| 7,004,933 B2 | 2/2006 | McCaniel |
| 7,044,938 B2 | 5/2006 | La Bianco et al. |
| 7,052,503 B2 | 5/2006 | Bernabei |
| 7,069,073 B2 | 6/2006 | Henley et al. |
| 7,070,488 B2 | 7/2006 | Suissa et al. |
| 7,083,580 B2 | 8/2006 | Bernabei |
| 7,087,063 B2 | 8/2006 | Carson et al. |
| 7,094,252 B2 | 8/2006 | Koop |
| 7,115,275 B2 | 10/2006 | Clarot et al. |
| 7,135,011 B2 | 11/2006 | Powers et al. |
| 7,153,311 B2 | 12/2006 | Chung |
| 7,197,359 B1 | 3/2007 | Tokudome et al. |
| 7,198,623 B2 | 4/2007 | Fischer et al. |
| 7,232,444 B2 | 6/2007 | Chang |
| 7,241,208 B2 | 7/2007 | Suissa et al. |
| 7,276,051 B1 | 10/2007 | Henley et al. |
| 7,314,326 B2 | 1/2008 | Rosenberg |
| 7,316,657 B2 | 1/2008 | Kleinhenz et al. |
| 7,318,828 B1 | 1/2008 | Revivo |
| 7,320,691 B2 | 1/2008 | Pilcher et al. |
| 7,320,801 B2 | 1/2008 | Kelly |
| 7,354,423 B2 | 4/2008 | Zelickson et al. |
| 7,364,565 B2 | 4/2008 | Freeman |
| 7,384,405 B2 | 6/2008 | Rhoades |
| 7,427,273 B2 | 9/2008 | Mitsui |
| 7,458,944 B2 | 12/2008 | Liste et al. |
| 7,476,205 B2 | 1/2009 | Erdmann |
| 7,477,938 B2 | 1/2009 | Sun et al. |
| 7,482,314 B2 | 1/2009 | Grimes et al. |
| 7,489,989 B2 | 2/2009 | Sukhanov et al. |
| 7,507,228 B2 | 3/2009 | Sun et al. |
| 7,582,067 B2 | 9/2009 | Van Acker |
| 7,597,900 B2 | 10/2009 | Zimmer et al. |
| 7,597,901 B2 | 10/2009 | Clarot et al. |
| 7,658,742 B2 | 2/2010 | Karasiuk |
| 7,678,120 B2 | 3/2010 | Shadduck |
| 7,744,582 B2 | 6/2010 | Sadowski et al. |
| 7,789,886 B2 | 9/2010 | Shadduck |
| 7,837,695 B2 | 11/2010 | Hart et al. |
| 7,901,373 B2 | 3/2011 | Tavger |
| 7,951,156 B2 | 5/2011 | Karasiuk |
| 8,025,669 B1 | 9/2011 | David et al. |
| RE42,960 E | 11/2011 | Waldron |
| 8,048,089 B2 | 11/2011 | Ignon et al. |
| 8,066,716 B2 | 11/2011 | Shadduck |
| 8,088,085 B2 | 1/2012 | Thiebaut et al. |
| 8,128,638 B2 | 3/2012 | Karasiuk et al. |
| 8,221,437 B2 | 7/2012 | Waldron et al. |
| 8,236,008 B2 | 8/2012 | Boone, III et al. |
| 8,277,287 B2 | 10/2012 | Hart |
| 8,337,513 B2 | 12/2012 | Shadduck |
| 8,343,116 B2 | 1/2013 | Ignon et al. |
| 8,814,836 B2 | 8/2014 | Ignon et al. |
| 9,056,193 B2 | 6/2015 | Ignon et al. |
| 2001/0023351 A1 | 9/2001 | Eilers |
| 2001/0049511 A1 | 12/2001 | Coleman et al. |
| 2002/0016601 A1 | 2/2002 | Shadduck |
| 2002/0041891 A1 | 4/2002 | Cheski |
| 2002/0058952 A1 | 5/2002 | Weber et al. |
| 2002/0107527 A1 | 8/2002 | Burres |
| 2002/0133110 A1 | 9/2002 | Citow |
| 2002/0133176 A1 | 9/2002 | Parkin et al. |
| 2002/0151826 A1 | 10/2002 | Ramey et al. |
| 2002/0151908 A1 | 10/2002 | Mallett, Sr. |
| 2002/0188261 A1 | 12/2002 | Hruska |
| 2003/0012415 A1 | 1/2003 | Cossel |
| 2003/0018252 A1 | 1/2003 | Duchon et al. |
| 2003/0060834 A1 | 3/2003 | Muldner |
| 2003/0093040 A1 | 5/2003 | Mikszta et al. |
| 2003/0093089 A1 | 5/2003 | Greenberg |
| 2003/0097139 A1 | 5/2003 | Karasiuk |
| 2003/0167032 A1 | 9/2003 | Ignon |
| 2003/0187462 A1 | 10/2003 | Chang |
| 2003/0208159 A1* | 11/2003 | Ignon et al. .................. 604/140 |
| 2003/0212127 A1 | 11/2003 | Glassman et al. |
| 2003/0212415 A1 | 11/2003 | Karasiuk |
| 2004/0010222 A1 | 1/2004 | Nunomura et al. |
| 2004/0010269 A1 | 1/2004 | Grimes et al. |
| 2004/0015139 A1 | 1/2004 | LaBianco |
| 2004/0087972 A1 | 5/2004 | Mulholland et al. |
| 2004/0092895 A1 | 5/2004 | Harmon |
| 2004/0092959 A1 | 5/2004 | Bernaz |
| 2004/0097967 A1 | 5/2004 | Ignon |
| 2004/0122447 A1 | 6/2004 | Harmon et al. |
| 2004/0143274 A1 | 7/2004 | Shadduck |
| 2004/0162565 A1 | 8/2004 | Carson et al. |
| 2004/0166172 A1 | 8/2004 | Rosati et al. |
| 2004/0219179 A1 | 11/2004 | McDaniel |
| 2004/0236291 A1 | 11/2004 | Zelickson et al. |
| 2004/0243149 A1 | 12/2004 | Lee, Jr. |
| 2004/0254587 A1 | 12/2004 | Park |
| 2004/0267285 A1 | 12/2004 | Chang |

(56) References Cited

U.S. PATENT DOCUMENTS

| | | |
|---|---|---|
| 2005/0037034 A1 | 2/2005 | Rhoades |
| 2005/0038448 A1 | 2/2005 | Chung |
| 2005/0059940 A1 | 3/2005 | Weber et al. |
| 2005/0084509 A1 | 4/2005 | Bernstein |
| 2005/0148958 A1 | 7/2005 | Rucinski |
| 2005/0203111 A1 | 9/2005 | David |
| 2005/0209611 A1 | 9/2005 | Greenberg |
| 2005/0283176 A1 | 12/2005 | Law |
| 2006/0002960 A1 | 1/2006 | Zoeteweij et al. |
| 2006/0116674 A1 | 6/2006 | Goble et al. |
| 2006/0161178 A1 | 7/2006 | Lee |
| 2006/0189964 A1 | 8/2006 | Anderson |
| 2006/0191562 A1 | 8/2006 | Nunomura |
| 2006/0200099 A1 | 9/2006 | La Bianco et al. |
| 2006/0200172 A1 | 9/2006 | Shadduck |
| 2006/0200173 A1 | 9/2006 | Shadduck |
| 2006/0212029 A1 | 9/2006 | Arcusa Villacampa et al. |
| 2006/0253125 A1 | 11/2006 | Ignon |
| 2006/0264893 A1 | 11/2006 | Sage, Jr. et al. |
| 2007/0005078 A1 | 1/2007 | Hart et al. |
| 2007/0043382 A1 | 2/2007 | Cheney |
| 2007/0065515 A1 | 3/2007 | Key |
| 2007/0088371 A1 | 4/2007 | Karasiuk |
| 2007/0123808 A1 | 5/2007 | Rhoades |
| 2007/0154502 A1 | 7/2007 | Hattendorf et al. |
| 2007/0156124 A1 | 7/2007 | Ignon et al. |
| 2007/0178121 A1 | 8/2007 | First et al. |
| 2007/0198031 A1 | 8/2007 | Kellogg |
| 2007/0208353 A1 | 9/2007 | Shadduck |
| 2007/0239173 A1 | 10/2007 | Khalaj |
| 2008/0027328 A1 | 1/2008 | Klopotek et al. |
| 2008/0091179 A1 | 4/2008 | Durkin et al. |
| 2008/0103563 A1 | 5/2008 | Powell |
| 2008/0119781 A1 | 5/2008 | King |
| 2008/0132914 A1 | 6/2008 | Bossard et al. |
| 2008/0139974 A1 | 6/2008 | Da Silva |
| 2008/0154161 A1 | 6/2008 | Abbott |
| 2008/0193493 A1 | 8/2008 | Rhoades |
| 2008/0200861 A1 | 8/2008 | Shalev et al. |
| 2008/0208146 A1 | 8/2008 | Brandwein et al. |
| 2008/0214987 A1 | 9/2008 | Xu |
| 2008/0215068 A1 | 9/2008 | Hart et al. |
| 2008/0221548 A1 | 9/2008 | Danenberg et al. |
| 2008/0243039 A1 | 10/2008 | Rhoades |
| 2008/0287864 A1 | 11/2008 | Rosenberg |
| 2008/0300529 A1 | 12/2008 | Reinstein |
| 2008/0300552 A1 | 12/2008 | Cichocki et al. |
| 2009/0048557 A1 | 2/2009 | Yeshurun et al. |
| 2009/0053390 A1 | 2/2009 | Sakou et al. |
| 2009/0062815 A1 | 3/2009 | Karasiuk et al. |
| 2009/0099091 A1 | 4/2009 | Hantash |
| 2009/0099093 A1 | 4/2009 | Hantash |
| 2009/0124985 A1 | 5/2009 | Hasenoehrl et al. |
| 2009/0138026 A1 | 5/2009 | Wu |
| 2009/0177171 A1 | 7/2009 | Ignon et al. |
| 2009/0192442 A1 | 7/2009 | Ignon et al. |
| 2009/0222023 A1 | 9/2009 | Boone, III et al. |
| 2010/0045427 A1 | 2/2010 | Boone, III et al. |
| 2010/0049177 A1 | 2/2010 | Boone, III et al. |
| 2010/0049210 A1 | 2/2010 | Boone, III et al. |
| 2011/0054490 A1 | 3/2011 | Hart |
| 2011/0066162 A1 | 3/2011 | Cohen |
| 2011/0082415 A1 | 4/2011 | Ignon et al. |
| 2012/0022435 A1 | 1/2012 | Ignon et al. |
| 2012/0041338 A1 | 2/2012 | Chickering, III et al. |
| 2012/0136374 A1 | 5/2012 | Karasiuk |
| 2013/0018317 A1 | 1/2013 | Bobroff et al. |
| 2013/0066336 A1 | 3/2013 | Boone, III et al. |
| 2013/0096577 A1 | 4/2013 | Shadduck |
| 2013/0102978 A1 | 4/2013 | Ignon et al. |
| 2013/0144280 A1 | 6/2013 | Eckhouse et al. |
| 2013/0158547 A1 | 6/2013 | David |
| 2014/0343481 A1 | 11/2014 | Ignon |
| 2014/0343574 A1 | 11/2014 | Ignon et al. |
| 2015/0230824 A1 | 8/2015 | Shadduck |
| 2015/0230825 A1 | 8/2015 | Shadduck |
| 2015/0231379 A1 | 8/2015 | Ignon |
| 2015/0265822 A1 | 9/2015 | Ignon et al. |
| 2015/0272632 A1 | 10/2015 | Seelig |
| 2015/0290442 A1 | 10/2015 | Ignon et al. |
| 2016/0038183 A1 | 2/2016 | Ignon et al. |

FOREIGN PATENT DOCUMENTS

| | | |
|---|---|---|
| DE | 10 2004 015815 A1 | 11/2005 |
| EP | 0 258 901 | 9/1987 |
| EP | 0 564 392 | 3/1993 |
| IT | 553 076 | 12/1956 |
| IT | 118 49 22 | 3/1985 |
| JP | 1993-088552 | 12/1993 |
| JP | 09-294747 | 11/1997 |
| JP | 2003-339713 | 12/2003 |
| JP | 2006-503627 | 2/2006 |
| JP | 2006-204767 | 10/2006 |
| KR | 20-0280320 | 7/2002 |
| WO | WO 00/15300 | 3/2000 |
| WO | WO 01/93931 | 12/2001 |
| WO | WO 03/073917 | 9/2003 |
| WO | WO 2004/037098 | 5/2004 |
| WO | WO 2005/070313 | 8/2005 |
| WO | WO 2006/018731 | 2/2006 |
| WO | WO 2007/114904 | 10/2007 |
| WO | WO 2012/145667 | 10/2012 |

OTHER PUBLICATIONS

File History of Reissue U.S. Appl. No. 11/027,590, filed Dec. 29, 2004 (Reissue of U.S. Pat. No. 6,500,183, issued Dec. 31, 2002).

File History of Reexamination U.S. Appl. No. 90/007,683 (Reexamination of U.S. Pat. No. 6,241,739, issued Jun. 5, 2001).

Cox III et al., *Decreased Splatter in Dermabrasion*, Arch Facial Plastic Surgery, Jan.-Mar. 2000, vol. 2, pp. 23-26.

Ditre et al., *Effect of a-hydroxy acids on photoaged skin: A pilot clinical, histologic, and ultrastructural study*, Journal of American Academy of Dermatology, Feb. 1996, vol. 34, No. 2, Part 1, pp. 187-195.

Harris et al., *Combining Manual Dermasanding with Low Stregnth Trichloroacetic Acid to Improve Antinically Injured Skin*, The Journal of Dermatologic Surgery and Oncology, Jul. 1994, vol. 20, No. 7, pp. 436-442.

U.S. Appl. No. 13/620,164, filed Sep. 14, 2012, Instruments and Techniques for Controlled Removal of Epidermal Layers.

U.S. Appl. No. 14/702,509, filed May 1, 2015, Devices and Systems for Treating the Skin Using Vaccum.

U.S. Appl. No. 14/698,673, filed Apr. 28, 2015, Console System for the Treatment of Skin.

U.S. Appl. No. 14/698,713, filed Apr. 28, 2015, Methods and Systems for Extraction of Materials From Skin.

U.S. Appl. No. 14/700,789, filed Apr. 30, 2015, Tip With Embedded Materials for Skin Treatment.

U.S. Appl. No. 11/370,200, filed Mar. 7, 2006, Microdermabrasion Method and Apparatus.

U.S. Appl. No. 14/734,995, filed Jun. 9, 2015, Devices and Systems for Treating Skin Surfaces.

U.S. Appl. No. 15/344,357, filed Nov. 4, 2016, Devices and Methods for Skin Treatment.

U.S. Appl. No. 14/211,089, filed Mar. 14, 2014, Skin Treatment Systems and Methods Using Needles.

U.S. Appl. No. 14/211,290, filed Mar. 14, 2014, Devices, Systems and Methods for Treating the Skin.

U.S. Appl. No. 14/774,641, filed Sep. 10, 2015, Devices, Systems and Methods for Treating the Skin.

U.S. Appl. No. 14/998,375, filed Dec. 23, 2015, Devices and Methods for Treating the Skin Using a Rollerball or a Wicking Member.

U.S. Appl. No. 15/204,939, filed Jul. 7, 2016, Devices, Systems and Methods for Promoting Hair Growth.

* cited by examiner

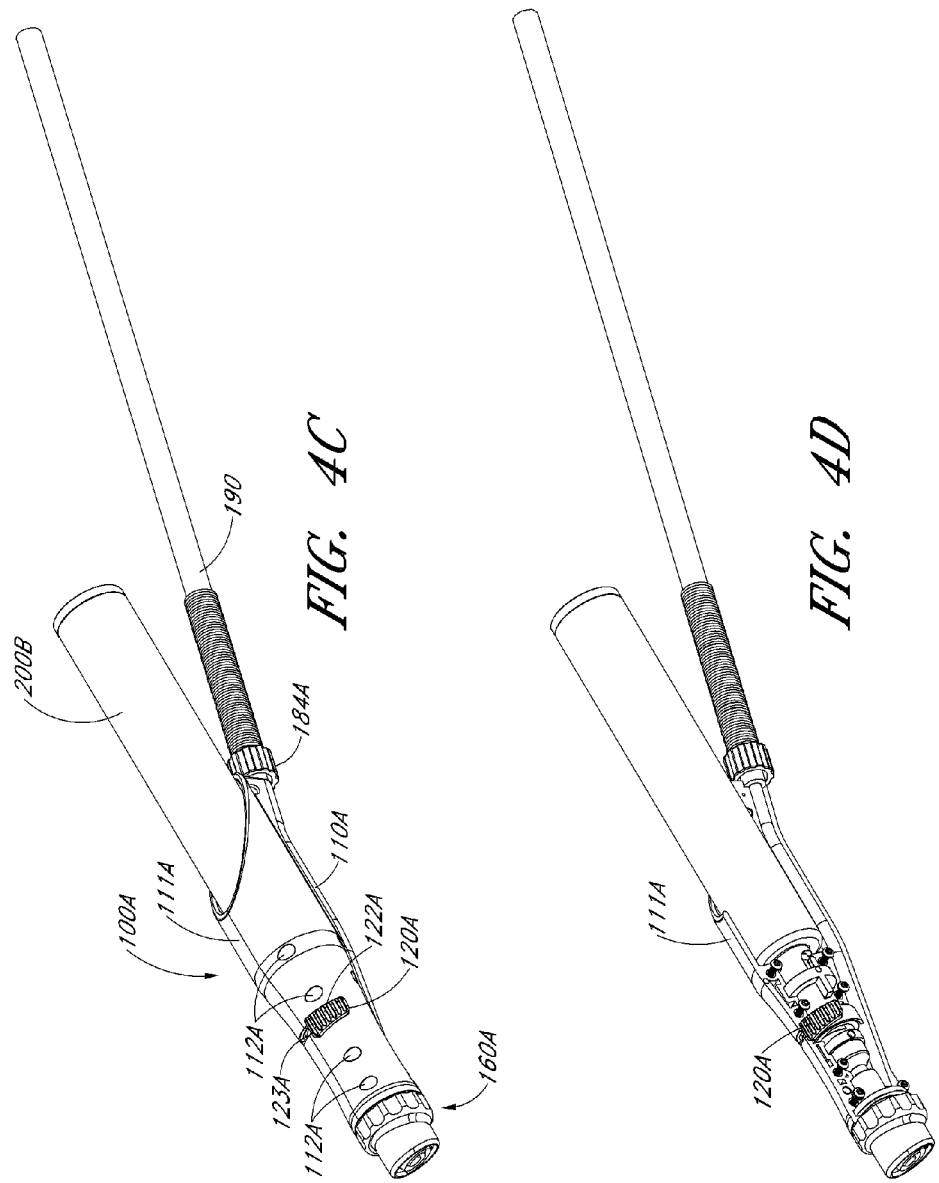

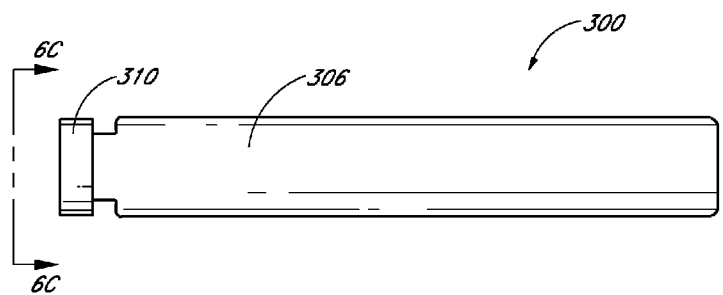
FIG. 6A
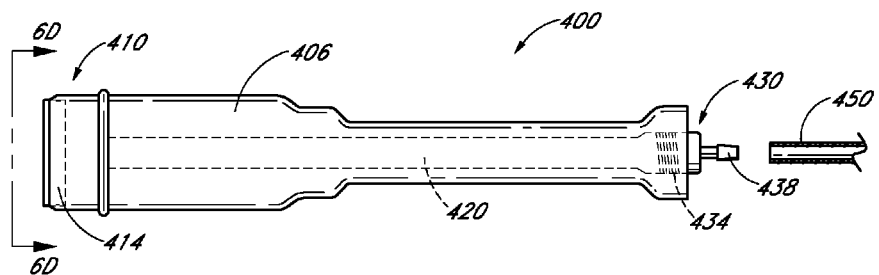
FIG. 6B
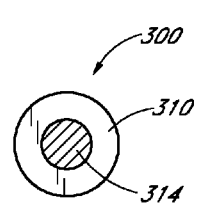 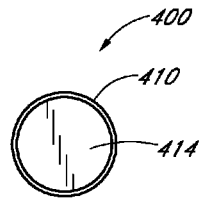
FIG. 6C    FIG. 6D

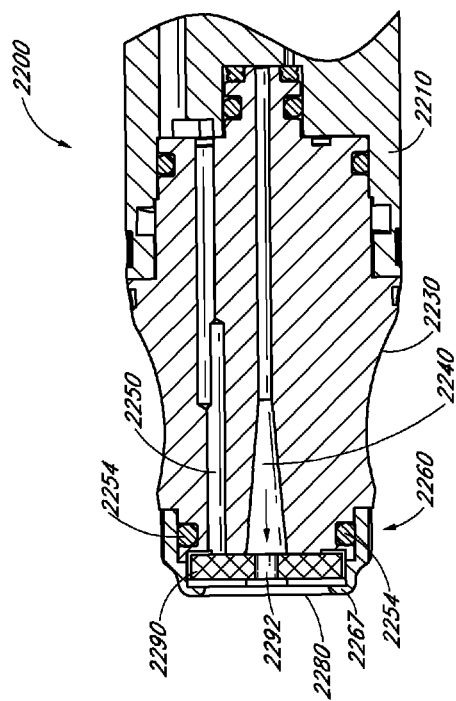
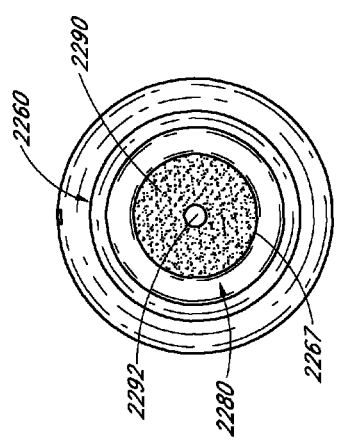
FIG. 23A
FIG. 23B

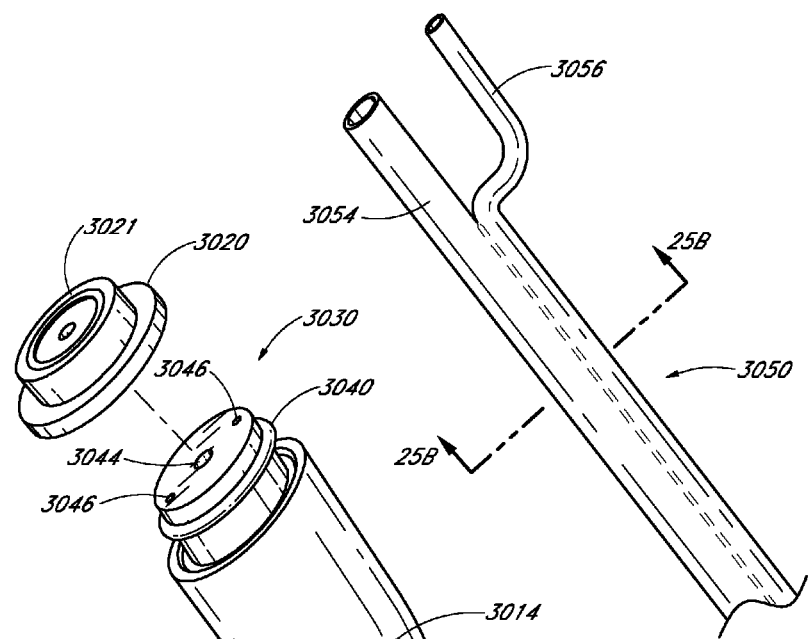
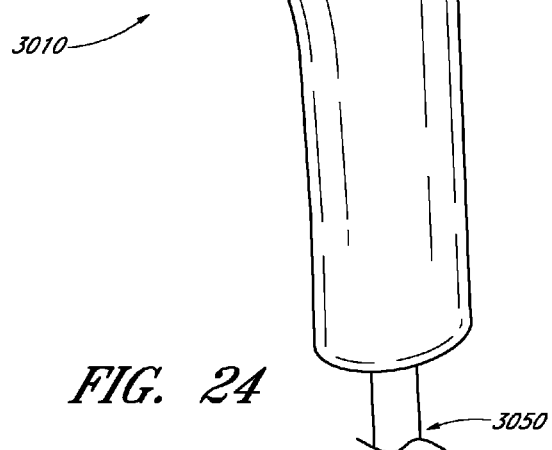
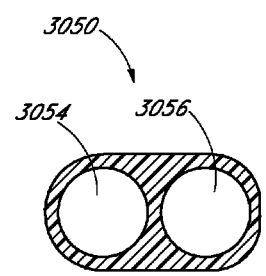
FIG. 25A
FIG. 24
FIG. 25B

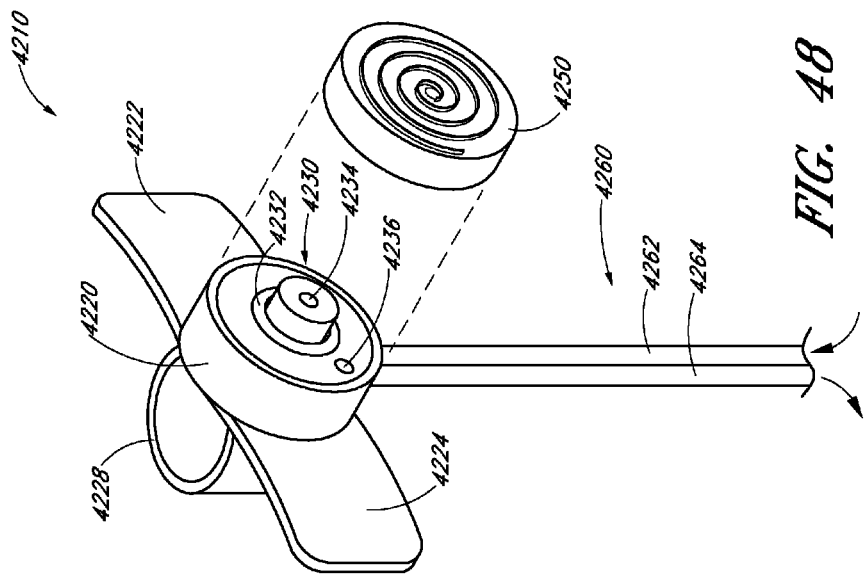
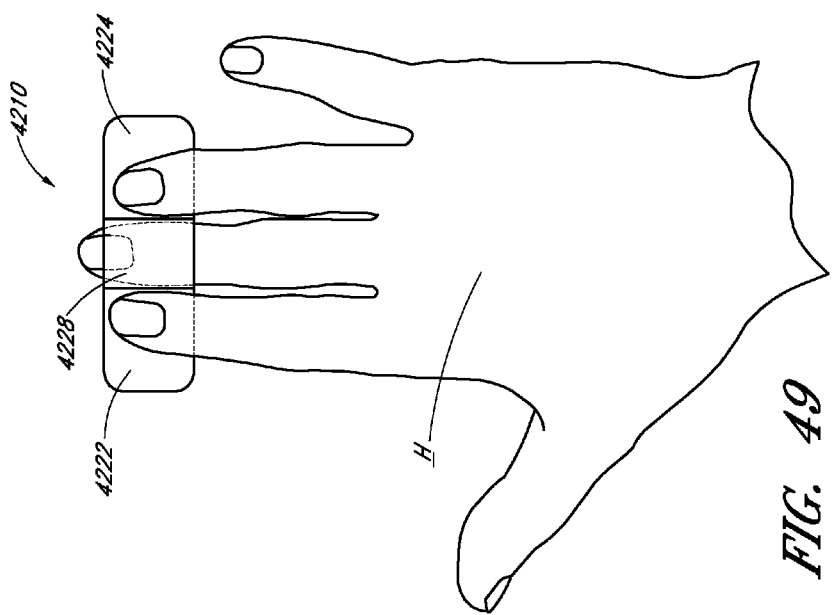

DEVICES FOR TREATING SKIN USING TREATMENT MATERIALS LOCATED ALONG A TIP

RELATED APPLICATIONS AND INCORPORATION BY REFERENCE

This application is a continuation of U.S. patent application Ser. No. 12/832,663, filed Jul. 8, 2010, which is a continuation-in-part of U.S. patent application Ser. No. 12/362,353, filed Jan. 29, 2009, which claims the priority benefit under 35 U.S.C. §119(e) of U.S. Provisional Patent Application No. 61/024,504, filed Jan. 29, 2008. All of the foregoing application are hereby incorporated by reference and made a part of the present specification. This application also claims the priority benefit under 35 U.S.C. §119(e) of U.S. Provisional Patent Application No. 61/224,044, filed Jul. 8, 2009, U.S. Provisional Patent Application No. 61/229,674, filed Jul. 29, 2009, and U.S. Provisional Patent Application No. 61/254,152, filed Oct. 22, 2009, all of which are hereby incorporated by reference and made a part of the present specification. In addition, the entirety of U.S. patent application Ser. No. 12/346,582, filed Dec. 30, 2008 and published on Jul. 9, 2009 as U.S. Publication No. 2009/0177171, is hereby incorporated by reference herein and made a part of the present specification.

BACKGROUND

Field of the Inventions

This application relates generally to skin treatment, and more specifically, to apparatuses, systems and methods for treating a person's skin.

Description of the Related Art

Abrasion of the outer layer or epidermis of the skin is desirable to smooth or blend scars, blemishes or other skin conditions that may be caused by, for example, sun exposure, acne, other skin disorders, aging and/or the like. Standard techniques used to abrade the skin have generally been separated into two fields that are commonly referred to as dermabrasion and microdermabrasion. In both techniques, portions of the epidermis (e.g., the stratum corneum) are removed. As part of its normal regeneration function, the body then replaces the lost skin cells, resulting in a new outer layer of skin. Additionally, despite the mild edema and erythema associated with the procedures, the skin eventually looks and feels smoother than prior to the treatment because of the new outer layer of skin.

Dermabrasion generally refers to a procedure in which the outer surface of the skin is removed due to mechanical rubbing by a handpiece with an abrasive element that is often in the form of a burr, wheel, disc or the like. This process tends to be messy and painful, sometimes necessitating the administration of a local anesthetic to the person being treated. In general, dermabrasion leaves the skin red and raw-looking. The removed skin can take several months to regrow and heal. Recent efforts have led to the use of lasers instead of abrasive elements, resulting in less bleeding. However, the pain and messiness of such procedures normally remain.

Efforts have been made to decrease the mess caused by the process waste, such as, for example, removed skin, blood, other debris and the like, by adding a suction element. As the process waste is drawn into the suction opening, skin that has not been removed is also pulled against the grit surrounding the suction opening, so the procedure remains relatively messy due to the abrasion that takes place outside of the handpiece by the grit.

In general, microdermabrasion refers generally to a procedure in which the surface of the skin is removed by mechanical rubbing using a handpiece that can discharge a stream of sand or grit. For example, a handpiece can be used to direct a fluid containing crystals of aluminum oxide, sodium chloride and/or sodium bicarbonate. The velocity and momentum of the grit helps wear away cell layers of the skin with each pass of the handpiece. Alternatively, new "crystal-free" microdermabrasion techniques utilize a diamond-tipped handpiece without a stream of grit.

Efforts to add a suction element have been more successful in microdermabrasion than in dermabrasion, because the handpiece applying the stream of grit is more controllable to a localized area. That is, as the removed skin is drawn into the suction opening, skin that has not been removed is also pulled towards the handpiece where it is treated with the grit stream, allowing for simultaneous local treatment and suction.

Microdermabrasion typically removes moisture from the skin. Thus, the procedure is generally followed by the application of moisturizing creams, other agents and/or other materials. However, similar to topical application of moisturizing creams prior to microdermabrasion, the moisturizing elements only work as deep as the active ingredients can passively migrate through the remaining epidermis.

SUMMARY

According to some embodiments, a microdermabrasion device for treating skin comprises a handpiece assembly having a distal end and a proximal end. The handpiece assembly includes at least one delivery conduit and at least one waste conduit. The microdermabrasion device additionally comprises a tip configured to be positioned along the distal end of the handpiece assembly, wherein the tip is adapted to contact skin surface. According to some embodiments, the microdermabrasion device further includes a flow control device or feature included within the handpiece assembly to regulate the flow of fluids through the delivery conduit. In several embodiments, the tip comprises a lip, a first opening in fluid communication with the fluid delivery conduit and a second opening in fluid communication with the waste conduit. In one embodiment, the device includes one or more abrasive elements positioned along a distal end of the tip, wherein the abrasive elements are configured to selectively remove skin as the tip is moved relative to a skin surface. In some embodiments, the first opening, the second opening and the abrasive elements of the tip are positioned within an interior of an outer periphery formed by the lip. In some embodiments, the waste conduit is in fluid communication with a vacuum source to selectively remove debris away from the tip. In one embodiment, the delivery conduit is in fluid communication with the at least one waste conduit and the vacuum source when the lip contacts a skin surface. In some embodiments, the delivery conduit is configured to selectively deliver at least one time-release material to the skin surface being treated.

According to some embodiments, the flow control device comprises a valve (e.g., a needle valve). In some embodiments, the abrasive element comprises a protruding member, a spiral ridge or an abrasive surface. In other embodiments, the abrasive element comprises an abrasive disc, an abrasive surface and/or any other member that is configured to be separated from the tip or that is configured to be permanently attached to the tip. In one embodiment, the tip is removable from the handpiece assembly. In other embodiments, the time-release material comprises a plurality of microcapsules, capsules or other enclosures configured to release their internal contents at various times following delivery to the skin surface. In some embodiments, the time-release material comprises salicylic acid. In other embodiments, the time-release material comprises one or more other active and/or non-active ingredients (e.g., azelaic acid, topical retinoids, benzoyl peroxide, topical antibiotics, other anti-acne materials, saline, other dilutants or fluids, soaps, hardening agents, gels, other binders, lotions, moisturizers, peptides, amino acids, UVA and/or UVB sunblocks, other sunblocking agents, skin tightening agents, hyaluronic acid (HA), other hydration agents, hair removal or hair growth suppression agents, medicaments and pharmaceuticals, etc.), either alone or in combination with one another.

In one embodiment, the time-release material is impregnated along at least a portion of the tip. In other embodiments, the time-release material is initially contained within a cartridge or other container that is in fluid communication with the delivery conduit when the cartridge or other container is secured to the handpiece assembly. In other embodiments, the time release material is delivered to the tip of the handpiece without any prior dilution or premixing. In some embodiments, the handpiece assembly comprises a recess configured to removably receive a cartridge, wherein an internal content of the cartridge is placed in fluid communication with the delivery conduit when the cartridge is secured within the recess of the handpiece assembly. In some embodiments, the cartridge or container comprises a movable piston therein, wherein the movable piston configured to urge an internal content of the cartridge toward an outlet of the cartridge. In some embodiments, the cartridge or container comprises an airless pump design or configuration. In one embodiment, the time-release material is configured to treat a skin disorder or condition (e.g., acne, oily or dry skin, etc.).

According to certain arrangements, a device for treating a skin surface includes a handpiece assembly having a distal end and a proximal end such that the handpiece assembly comprises at least one delivery conduit and at least one waste conduit. The device additionally comprises a tip configured to be positioned along the distal end of the handpiece assembly, such that the tip is adapted to contact the skin surface being treated. According to certain embodiments, the tip comprises a peripheral lip, a first opening in fluid communication with the fluid delivery conduit and a second opening in fluid communication with the waste conduit and an abrasive element or surface positioned along a distal end of the tip, said abrasive element or surface configured to remove skin. In one embodiment, the first opening, the second opening and the abrasive element of the disc are positioned along an interior of the peripheral lip. In another arrangement, one or more waste conduits are configured to be in fluid communication with a vacuum to selectively remove debris away from the tip. In other configurations, a delivery conduit is placed in fluid communication with the waste conduit and the vacuum when the peripheral lip contacts a skin surface. In yet other embodiments, one or more time-release materials are configured to be delivered to the skin surface being treated.

In some embodiments, the handpiece assembly comprises a housing having a clamshell design. In one embodiment, a housing of the handpiece assembly comprises two or more portions that are configured to removably or permanently attach to each other (e.g., using screws, other fasteners, snap fit or friction fit connections, adhesives, welds and/or any other connection method or device). In some embodiments, the two or more portions of the housing are configured to be manufactured using an injection molding procedure or any other molding or manufacturing process (e.g., compression molding, thermoforming, extrusion, etc.). In one embodiment, the two portions or more portions of the housing comprise a plastic, metal, alloy and/or any other synthetic or natural material.

According to other embodiments, the device additionally includes a valve configured to control a flowrate of a fluid being delivered through the fluid delivery conduit to the tip. In another arrangement, the abrasive element or structure comprises one or more protruding members, spiral ridges and/or abrasive surfaces. In certain embodiments, the time-release material comprises a plurality of microcapsules or capsules configured to release their internal contents at various times following delivery to the skin surface. In one embodiment, the time-release materials comprise one or more of the following: peptides, amino acids, UVA and/or UVB sunblocks, other sunblocking agents, skin tightening agents, hyaluronic acid (HA), other hydration agents, hair removal or hair growth suppression agents, medicaments and pharmaceuticals, combinations thereof and/or any other substance. In other arrangements, time-release materials are impregnated along at least a portion of the tip. In yet other embodiments, the cartridge or other container is in fluid communication with the handpiece assembly. In certain embodiments, the time-release materials are configured to be released to the skin surface after contact with water or another dilutant. In other arrangements, the time-release materials are configured to treat acne or another skin disorder.

According to certain embodiments of the present application, a handpiece assembly for treating a skin surface comprises a recess configured to receive a cartridge or other container. The cartridge or other container comprises one or more treatment materials, such as, for example, human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, acids, anesthetics, medicants, other non-active or active compounds, other fluids or materials, combination or mixtures thereof and/or any other substance. In one embodiment, the handpiece assembly comprises a valve or other flow control device or feature to enable a user to selectively regulate a flowrate of a treatment material through the handpiece assembly. In other embodiments, the cartridge or other container comprises an inlet configured to be in fluid communication with water, saline, another dilutant or dissolvent or another fluid. The water, saline, another dilutant or dissolvent or another fluid is configured to be delivered through the inlet and to an interior of the cartridge so as to mix or combine with a treatment material contained therein. In some embodiments, the treatment material contained within the cartridge or container is a liquid, solid, gel, granulated material or concentrated solution. In some embodiments, one or more treatment fluids are conveyed from an outlet of the cartridge or container to a tip attached to a distal end of the handpiece assembly.

According to certain arrangements, treatment materials that are provided to the skin interface during a dermabrasion procedure are configured to be released or otherwise made available to a user's skin over a pre-selected, relatively extended time period. Such time release materials can be provided in the form of microcapsules, other capsules or enclosures and/or the like.

Regardless of the form in which they are provided (e.g., within microcapsules or other enclosures), time-release products or materials can be delivered to a skin surface directly through a cartridge or other container. Such a cartridge can be positioned within a handpiece assembly, such as, for example, those illustrated in FIGS. 1-4F, 13A-16B and 18B herein. Cartridges or other containers containing such time-release materials can be provided in various locations of a handpiece assembly, including, without limitation, a recess of the main portion, underneath or near a removable tip and/or the like. In certain embodiments, a cartridge or other container containing one or more time-release materials is separate from the handpiece assembly. For example, as illustrated in FIG. 18A, such a cartridge or other container can be placed along a delivery line, which selectively supplies fluids and/or other materials through the cartridge to a handpiece assembly. In other arrangements, such as, for example, those illustrated in FIGS. 6B, 7, 17 and 20A-23B herein, time-release materials can be provided to the handpiece assembly from one or more upstream containers or other sources via a delivery line. By way of example, in accordance with the configuration depicted herein in FIGS. 7 and 17, time-release and/or other products and substances can be placed within one or more containers of a manifold system. Such materials can be subsequently delivered through a handpiece assembly using one or more conduits to the skin area being treated.

In yet other arrangements, time-release materials are advantageously provided, either alone or in combination with one or more other substances, within a recess, cavity or other opening or a tip or other portion of a skin treatment system. For example, such recesses can be provided along a distal surface of the tip, as illustrated in FIGS. 12A-12C and discussed in greater detail herein. In certain embodiments, one or more time-release materials are embedded, impregnated, placed, stored and/or otherwise disposed on one or more surfaces or areas of the tip or other portion or component of the skin treatment system (e.g., the foam pads of FIG. 19A-20B). Such time-release materials, which may be provided alone or in combination with any other materials, can comprise microcapsules, other capsules, solids, semi-solids, other dried substances, gels, concentrated solutions and/or the like. In some arrangements, time-release materials and/or other substances are provided in capsules (e.g., microcapsules), caps, loose form (e.g., positioned on or within a recess, other portion of the tip, within a cartridge or other container, adhered to one or more surfaces, etc.), as a tablet, pill, disc or other dissolvable solid, saturated within a foam pad or other sponge-like material and/or the like.

Regardless of where the time-release materials are positioned relative to the handpiece assembly (e.g., within a cartridge or other container, within or outside of a handpiece assembly, in a recess or other opening of a tip or other portion of a handpiece assembly, within a foam pad, on a surface of a tip or other portion of a handpiece assembly, etc.), water (e.g., distilled, tap water, filtered, etc.), saline, other dilutants and/or other fluids can be used to selectively dissolve, liquefy, melt, soften, dilute or otherwise prepare the time-release and/or any other materials. Accordingly, the desired salicylic acid, other anti-acne materials, human growth factors, cytokines, soluble collagen, antioxidants, matrix proteins, serums, water, saline, other dilutants or dissolvents, vitamins, chemical exfoliation agents, lotions, soothing agents, brightening or lightening agents, peptides, amino acids, other acids, anesthetics, UVA and/or UVB sunblocks, other sunblocking agents, skin tightening agents, hyaluronic acid (HA), other hydration agents, hair removal or hair growth suppression agents, medicaments and pharmaceuticals, other non-active or active compounds, other fluids or materials, combination or mixtures thereof and/or any other substance can be advantageously provided to the skin surface being treated, as desired or required.

According to certain embodiments, time-release materials include one or more active ingredients that target specific skin conditions or types. For instance, a time-release product used to help control skin acne can include salicylic acid. The salicylic acid can be provided alone or in combination with one or more other active and/or non-active ingredients (e.g., azelaic acid, topical retinoids, benzoyl peroxide, topical antibiotics, other anti-acne materials, saline, other dilutants or fluids, soaps, hardening agents, gels, other binders, lotions, moisturizers, peptides, amino acids, UVA and/or UVB sunblocks, other sunblocking agents, skin tightening agents, hyaluronic acid (HA), other hydration agents, hair removal or hair growth suppression agents, medicaments and pharmaceuticals, etc.).

Time-release salicylic acid capsules (e.g., microcapsules) and/or any other active or non-active ingredients included in a skin treatment material can be encapsulated within a solid binder, such as, for example, soap or gel. Thus, when water or another fluid is added to the material, the treatment material can at least partially dissolve, advantageously releasing capsules onto the skin surface. The capsules can be configured to release their internal contents at different time intervals after being deposited on or near a person's skin.

Alternatively, as discussed in greater detail herein, such microcapsules or other time-release materials can be provided within a cartridge, another container, a recess or other opening and/or the like. According to certain embodiments, the microcapsules or other time-release materials are included within a binder or are provided in loose form (e.g., as a solid, within a liquid, gel, other fluid or other medium, etc.). Thus, time-release materials can be selectively delivered to the skin (or be initially present at a tip-skin interface) in one or more different forms. Regardless of the exact manner in which they are provided to a person's skin, such time-release materials can help target certain skin ailments or conditions (e.g., acne, eczema, psoriasis, etc.), conditions (e.g., dry skin, oily skin, etc.) and/or the like.

In some embodiments, microcapsules and/or other time-release products delivered to the skin surface are configured to be released or otherwise become available to the skin at different times from each other. For example, microcapsules can be adapted to release salicylic acid and/or any other active or non-active ingredients contained therein in various time intervals (e.g., quarter-hour, half-hour, one-hour, two-hour, three-hour, etc.). Accordingly, the desired materials can be provided to a target skin surface to have an effect on such a surface over a longer period of time. This can facilitate a particular treatment procedure by effectively prolonging the overall treatment time-period. For example, in some embodiments, an acne treatment is more effective if salicylic acid is released over a targeted skin surface during a longer time period (e.g., less than 30 minutes, 1 hour, 2 hours, 4 hours, 6 hours, 8 hours, 10 hours, 12 hours, 24 hours, 36 hours, 48 hours, more than 48 hours, etc.).

In one embodiment, time-release materials are provided to a dermabrasion system which is adapted to treat skin having acne or another skin condition. A handpiece assembly having an abrasive distal end, such as, for example, a tip in accordance with any of the arrangements illustrated or otherwise disclosed herein, or equivalents thereof, can be used to treat a skin surface of a patient. As the tip is moved across the target skin area, exfoliated skin, infected waste and/or other materials can be advantageously removed. In addition, the treatment system can be configured to selectively deposit time-release product onto the treated skin before, after and/or contemporaneously with the exfoliation process. As discussed in greater detail herein, the time-release product can be delivered from a cartridge or other container located either within a handpiece assembly or separate from it. In some arrangements, water, saline and/or other dilutants are required to at least partially dissolve or otherwise release such substances (e.g., from a binder, gel, solid, etc.). Salicylic acid and/or any other materials contained within the time-release product (e.g., microcapsules, other capsules, caps, etc.) and/or other materials delivered to the patient's skin can be advantageously released over a longer time-period so as to help prevent or reduce the likelihood of bacterial infection, pain or discomfort, sensitivity to sunlight or other light sources and/or the like.

According to certain arrangements, time-release capsules or other materials containing salicylic acid and/or other skin solutions can be embedded on or near a surface of a tip using a binder. For example, glycerin soap or other base materials or hardening agents can be used to bind the time-release materials. As water, saline or other dilutants or fluids are selectively delivered to the bound materials, time-release materials can dissolve, allowing salicylic acid capsules to be released to a target area of the skin. In one configuration, the time-release materials comprise approximately 30% of the bound mixture by volume, while the soap or other base material and/or hardening agent comprises the remaining approximately 70%. In other embodiments, the volumetric ratio of time-release materials to base materials and hardening agents can be greater or less than 3:7, as required or desired (e.g., less than approximately 1:9, approximately 1:4, 2:3, 1:1, 3:2, 7:3, 4:1, more than approximately 4:1, etc.).

According to certain arrangements, a disc, plate or other member having diamonds or any other abrasive element is removably positioned within an interior region of the tip (e.g., generally between the tip and adjustable distal portion or any other component of the handpiece assembly). Such a disc, which is configured to contact and abrade skin through one or more openings of the tip, can be conveniently removed for cleaning, replacement and/or any other purpose According to other embodiments, a treatment material disposed on or near the tip of the handpiece assembly is configured to be mixed or combined with water, saline or another fluid being delivered through the handpiece assembly to create a treatment fluid. In certain embodiments, the treatment material is provided as a solid, semi-solid, gel, granulated material or concentrated fluid or solution. In some arrangements, the treatment material is positioned within a recess of the tip, between the tip and a main body portion of the handpiece assembly or within the main body portion of the handpiece assembly. In some embodiments, water, saline, treatment fluid or other fluid being conveyed through the handpiece assembly is configured to be heated.

According to certain embodiments of the present application, a device for treating a skin surface comprises a handpiece assembly having a distal end and a proximal end. The handpiece assembly comprises at least one delivery conduit and at least one waste conduit. The handpiece assembly further comprising a recess or other opening configured to receive a cartridge or other container having an interior cavity. In one embodiment, the interior cavity of the cartridge is placed in fluid communication with the fluid delivery conduit when the cartridge is secured within the recess. The device additionally includes a tip positioned along the distal end of the handpiece assembly, such that the tip is configured to contact the skin surface. In certain embodiments, the tip comprises a peripheral lip, a first opening in fluid communication with the fluid delivery conduit and a second opening in fluid communication with the waste conduit and an abrasive element. The first opening, the second opening and the abrasive element are generally positioned along an interior of the peripheral lip. In one embodiment, the waste conduit is configured to be in fluid communication with a vacuum to selectively remove debris away from the tip. In other arrangements, the delivery conduit is placed in fluid communication with the waste conduit and the vacuum when the peripheral lip contacts a skin surface.

In certain arrangements, the device further includes a valve generally positioned between the interior cavity of the cartridge and the fluid delivery conduit. The valve can be adapted to control the flowrate of a fluid being conveyed from the interior cavity of the cartridge to the tip. In other embodiments, the handpiece assembly comprises an adjustable intermediate space positioned generally between the interior cavity of the cartridge and the fluid delivery conduit. In one arrangement, a volume of the adjustable intermediate space can be selectively modified by moving an actuator on the handpiece assembly. In other configurations, the handpiece assembly comprises a stem in fluid communication with the fluid delivery conduit. The stem can be adapted to extend into the interior cavity of a cartridge when the cartridge is positioned with the recess of the handpiece assembly. In other embodiments, the tip is selectively removable from the handpiece assembly. In one arrangement, the abrasive element comprises a plurality of posts, other protruding members, a spiral-shaped ridge, an abrasive surface, a foam pad, another type of pad and/or the like. In some arrangements, the device further includes a heating element configured to selectively heat a fluid being conveyed through the delivery conduit, another interior passage or conduit of the handpiece assembly, the tip, an inlet line and/or the like. In other embodiments, the cartridge comprises an inlet configured to be placed in fluid communication with a delivery source.

According to other arrangements, a skin treatment system includes a handpiece assembly having a distal end and a proximal end. The handpiece assembly comprises a fluid delivery conduit. In one embodiment, the handpiece assembly comprises a first portion and a second portion, with the first portion being selectively movable relative to the second portion. The skin treatment system further includes a tip adapted to contact skin and positioned on the distal end of the handpiece assembly. In one embodiment, the tip comprises a first opening, which is in fluid communication with the fluid delivery conduit, and an abrasive element. The system further comprises an intermediate space generally defined between the first and second portions of the handpiece assembly. Movement of the first portion with respect to the second portion can modify the volume of the intermediate space and generally control the flowrate of a fluid being conveyed through the fluid delivery conduit. In some embodiments, the system further includes an actuator on the handpiece assembly for moving the first portion relative to the second portion.

According to other embodiments, movement of the first portion with respect to the second portion is produced by rotating the second portion relative to the first portion. In some arrangements, the tip is selectively removable from the second portion. In another adaptation, the tip comprises a plurality of posts or protruding members configured to treat skin. In other arrangements, the tip comprises one or more ridges (e.g., spiral-shaped ridges), abrasive surfaces or elements and/or other features or components configured to treat skin. In certain embodiments, the handpiece assembly further comprises a waste channel in fluid communication with a second opening in the tip. In another embodiment, the handpiece assembly includes a recessed area configured to receive a cartridge comprising at least one treatment fluid or material. In other arrangements, the cartridge includes an interior portion which is at least partially defined by a membrane. The membrane can be configured to be pierced by a hollow spike of the first portion of the handpiece assembly when the cartridge is properly inserted within the recessed area, so that the hollow spike is placed in fluid communication with the delivery channel. In certain configurations, the interior portion of the cartridge comprises human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, acids, anesthetics, medicants, other non-active or active compounds, other fluids or materials, combination or mixtures thereof and/or any other substance. In other arrangements, the device comprises a heater configured to selectively heat a fluid being conveyed through the fluid delivery conduit toward the tip.

According to certain embodiments, a method of providing a treatment fluid to a skin surface while treating said skin surface with a handpiece device includes providing at least one treatment material on or within a handpiece device. In one arrangement, a tip is configured to be removably positioned along a distal end of a main body portion of the handpiece assembly. The tip can be adapted to abrade or otherwise treat skin when moved relative to a skin surface. The treatment method additionally includes directing a first fluid through a delivery passage of the handpiece assembly so that said delivery passage generally contacts at least one treatment material of the tip. In some arrangements, the treatment material is configured to at least partially dissolve, dilute or combine with the first fluid so as to create a desired treatment fluid. Further, the treatment fluid can be configured to be provided to the tip and to the skin surface being treated while a distal end of the tip is being translated over said skin surface.

In some arrangements, the treatment material comprises a solid, granular material, gel or concentrated solution and/or any other material. In other embodiments, the first fluid comprises water (e.g., sterile, tap, distilled, filtered, etc.), saline, other dilutants or dissolvents and/or any other fluid. In other arrangements, the treatment fluid comprises human growth factors, cytokines, soluble collagen, antioxidants or matrix proteins. In another embodiment, the treatment material is positioned in or near the tip, such as, for example, within a post, other protruding member, other recess, underneath the tip and/or like. In other arrangements, the treatment material comprises a disc, tablet, capsule, granular material, gel and/or the like. In one embodiment, the treatment material is configured to be positioned within a cage or other porous container. In other arrangements, the disc, table, capsule or other treatment material is configured to be secured generally between the main body portion and the tip of the handpiece assembly. In one configuration, the method further includes regulating a flowrate of the first fluid by selectively controlling a valve on the handpiece assembly. In another arrangement, the method additionally includes selectively heating the first fluid using a heating member positioned in thermal communication with the delivery passage of the handpiece assembly. In some embodiments, the treatment material is positioned within a cartridge which is configured to be removably secured to a receiving area of the handpiece assembly.

According to some embodiments disclosed in the present application, a device for treating the skin comprises a handpiece assembly having a distal end and a proximal end, a cartridge comprising an interior cavity and a tip on the distal end of the handpiece assembly. The handpiece assembly includes a fluid delivery conduit and a waste conduit. In addition, the cartridge is coupled to the handpiece assembly, with the interior cavity of the cartridge being in fluid communication with the fluid delivery conduit. Further, the tip is configured to contact the skin. The tip comprises a peripheral lip, a first opening in fluid communication with the fluid delivery conduit, a second opening in fluid communication with the waste conduit and an abrasive element. The first opening, the second opening and the abrasive element of the tip are generally positioned within the peripheral lip.

In some embodiments, the device further comprises a valve positioned between the interior cavity of the cartridge and the fluid delivery conduit. In one embodiment, the handpiece assembly comprises an adjustable intermediate space positioned generally between the interior cavity of the cartridge and the fluid delivery conduit. In another arrangement, a volume of the adjustable intermediate space can be selectively modified by moving an actuator on the handpiece assembly. In other embodiments, the handpiece assembly comprises a recessed area configured to receive the cartridge.

According to other embodiments, the handpiece assembly comprises a stem that is in fluid communication with the fluid delivery conduit as the stem is configured to extend into the interior cavity of a cartridge when the cartridge is coupled to the handpiece assembly. In another embodiment, the tip is selectively removable from the handpiece assembly. In some arrangements, the abrasive element comprises a plurality of protruding members. In other embodiments, the tip comprises an abrasive edge.

According to another embodiment, a system for treating the skin comprises a handpiece assembly having a distal end and a proximal end and a tip on the distal end of the handpiece assembly configured to contact the skin. The handpiece assembly includes a fluid delivery conduit and first and second portions. Further, the tip includes a first opening in fluid communication with the fluid delivery conduit and an abrasive element. An intermediate space generally defined between the first and second portions of the handpiece assembly is in fluid communication with the fluid delivery conduit. In one embodiment, movement of the first portion with respect to the second portion modifies the volume of the intermediate space to control a flowrate through the fluid delivery conduit. The system further comprises an actuator on the handpiece assembly for actuating movement between the first portion and the second portion.

In some embodiments, movement of the first portion with respect to the second portion is produced by rotating the second portion relative to the first portion. In other embodiments, the tip is selectively removable from the second portion. In still other arrangements, the tip comprises a plurality of protruding members configured to treat skin. In another embodiment, the tip comprises an abrasive surface configured to treat skin.

According to some embodiments, the handpiece assembly further comprises a waste channel in fluid communication with a second opening in the tip. In another arrangement, the handpiece assembly includes a recessed area configured to receive a cartridge comprising at least one treatment fluid or material. In other embodiments, the cartridge includes an interior portion at least partially defined by a membrane. The membrane is configured to be pierced by a hollow spike of the first portion of the handpiece assembly. Further, the hollow spike is in fluid communication with the delivery channel. In one embodiment, the interior portion of the cartridge comprises human growth factors, cytokines, soluble collagen, antioxidants and/or matrix proteins.

According to other embodiments, the present application discloses a method for treating the skin of a patient with a skin treatment device having a working end that includes an abrading structure configured to engage and abrade skin. The method includes placing the working end of the skin treatment device against the skin of the patient, translating the working end over the skin to abrade a skin surface, providing a treatment fluid to the skin through an opening in the working end and aspirating skin debris from the skin surface through an aspiration opening in the working end of the skin treatment device. In some embodiments, the treatment fluid comprises human growth factors, cytokines, soluble collagen, antioxidants and/or matrix proteins.

According to some embodiments disclosed in the present application, a device for treating the skin comprises a handpiece assembly having a distal end and a proximal end. The handpiece assembly includes a fluid delivery conduit and a waste conduit. In addition, the handpiece assembly is adapted to receive a cartridge having an interior cavity. Further, the device includes a tip attached to the distal end of the handpiece assembly and comprising a surface configured to treat skin. The waste conduit is configured to be in fluid communication with a vacuum source and the fluid delivery conduit is configured to be in fluid communication with an interior cavity of a cartridge when a cartridge is secured to the handpiece assembly.

In some embodiments, the handpiece assembly comprises a flow control feature configured to selectively regulate a flowrate through the fluid delivery conduit. In another arrangement, the handpiece assembly includes a main body portion and an adjustable portion attached to the main body portion. The flow control feature can comprise an adjustable intermediate space generally located between the main body portion and the adjustable portion. In other embodiments, a volume of the adjustable intermediate space can be selectively modified by moving the main body portion relative to the adjustable portion of the handpiece assembly.

In one embodiment, the handpiece assembly comprises a recessed area configured to secure a cartridge. In another arrangement, the handpiece assembly comprises a stem adapted to access an interior cavity of a cartridge when a cartridge is secured to the handpiece assembly. According to some embodiments, the tip is selectively removable from the handpiece assembly. In other embodiments, the tip comprises a plurality of protruding members configured to treat skin. In still other arrangements, the tip comprises an abrasive surface configured to treat skin.

According to another embodiment, a system for treating the skin includes a handpiece assembly. The handpiece assembly comprises a tip configured to treat skin, a first portion and a second portion. The first portion includes a delivery conduit, which has a first longitudinal axis, and is configured to be in fluid communication with at least one fluid source. Further, the second portion includes a distal end and a proximal end, with the proximal end being attached to the main body portion and the distal end being attached to the tip. The second portion includes a delivery channel having a second longitudinal axis and being in fluid communication with the tip and the delivery conduit. In addition, the second portion further comprises a removal channel being in fluid communication with the tip and a suction source. In some embodiments, an intermediate space is generally defined between the first and second portions of the handpiece assembly. Such an intermediate space is in fluid communication with the delivery conduit of the first portion and the delivery channel of the second portion. Further, a volume of the intermediate space is configured to be adjusted by selectively modifying a separation distance between the first portion and the second portion. Accordingly, a flowrate from a fluid source to the tip can be selectively controlled by modifying the separation distance between the first portion and the second portion.

In some embodiments, the separation distance between the first portion and the second portion is modified by rotating the second portion relative to the first portion. In other arrangements, the first longitudinal axis of the delivery conduit is generally offset with the second longitudinal axis of the delivery channel. In one embodiment, the tip is selectively removable from the second portion.

According to some embodiments, the tip comprises a plurality of protruding members configured to treat skin. In other embodiments, the tip comprises an abrasive surface configured to treat skin. In one embodiment, the first portion further comprises a waste channel in fluid communication with the removal channel of the second portion. In another arrangement, the first portion includes a recessed area configured to receive a cartridge comprising at least one treatment fluid or material. In some embodiments, the cartridge includes an interior portion at least partially defined by a membrane which is configured to be pierced by a hollow spike of the first portion of the handpiece assembly. The hollow spike is in fluid communication with the delivery channel. According to other embodiments, the cartridge the interior portion of the cartridge comprises human growth factors, cytokines, soluble collagen, antioxidants or matrix proteins.

According to other embodiments disclosed in the present application, a method of treating the skin comprises providing a handpiece assembly comprising a body and a tip having a distal end. The handpiece assembly includes a delivery conduit and a waste conduit that are in fluid communication with the distal end of the tip. The method further includes placing the delivery conduit of the handpiece assembly in fluid communication with a fluid source for providing at least one treatment fluid to the distal end of the tip and placing the waste conduit of the handpiece assembly in fluid communication with a suction source for removing waste materials from the distal end of the tip. In addition, the method comprises moving the handpiece assembly along a person's skin and activating the suction source to remove a volume of waste materials from the distal end of the tip and to simultaneously deliver a volume of the treatment fluid to the distal end of the tip. In one embodiment, the flowrate at which treatment fluids and/or other materials are delivered to the tip can be varied by a valve or other flow control feature of the handpiece assembly. In some embodiments, the treatment fluid comprises human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents (e.g., kojic acid), peptides, acids, anesthetics, medicants, other non-active or active compounds, other fluids or materials, combination or mixtures thereof and/or any other substance.

BRIEF DESCRIPTION OF THE DRAWINGS

These and other features, aspects and advantages of the present inventions are described with reference to drawings of certain preferred embodiments, which are intended to illustrate, but not to limit, the present inventions. It is to be understood that the attached drawings are for the purpose of illustrating concepts of the present inventions and may not be to scale.

FIGS. 4C and 4D illustrate perspective views of a handpiece assembly according to another embodiment;

FIG. 6A illustrates a side view of one embodiment of a cartridge adapted to be inserted within a handpiece assembly;

FIG. 6B illustrates a side view of another embodiment of a cartridge adapted to be inserted within a handpiece assembly;

FIG. 6C illustrates a front view of the cartridge of FIG. 6A;

FIG. 6D illustrates a front view of the cartridge of FIG. 6B;

FIG. 23A illustrates a cross-sectional view of the handpiece assembly of FIG. 22;

FIG. 23B illustrates a front view of the handpiece assembly of FIG. 22;

FIG. 24 illustrates a perspective view of a handpiece assembly for use in a skin treatment system according to one embodiment;

FIG. 25A illustrates a perspective view of one embodiment of a conduit adapted for use in the handpiece assembly of FIG. 24;

FIG. 25B illustrates a cross-sectional view of one embodiment of the tubing of FIG. 25A;

FIG. 48 illustrates a perspective view of a skin treatment device according to another embodiment; and FIG. 49 illustrates a front view of the skin treatment device of FIG. 48 positioned on a user's hand.

DETAILED DESCRIPTION

Figure 1:
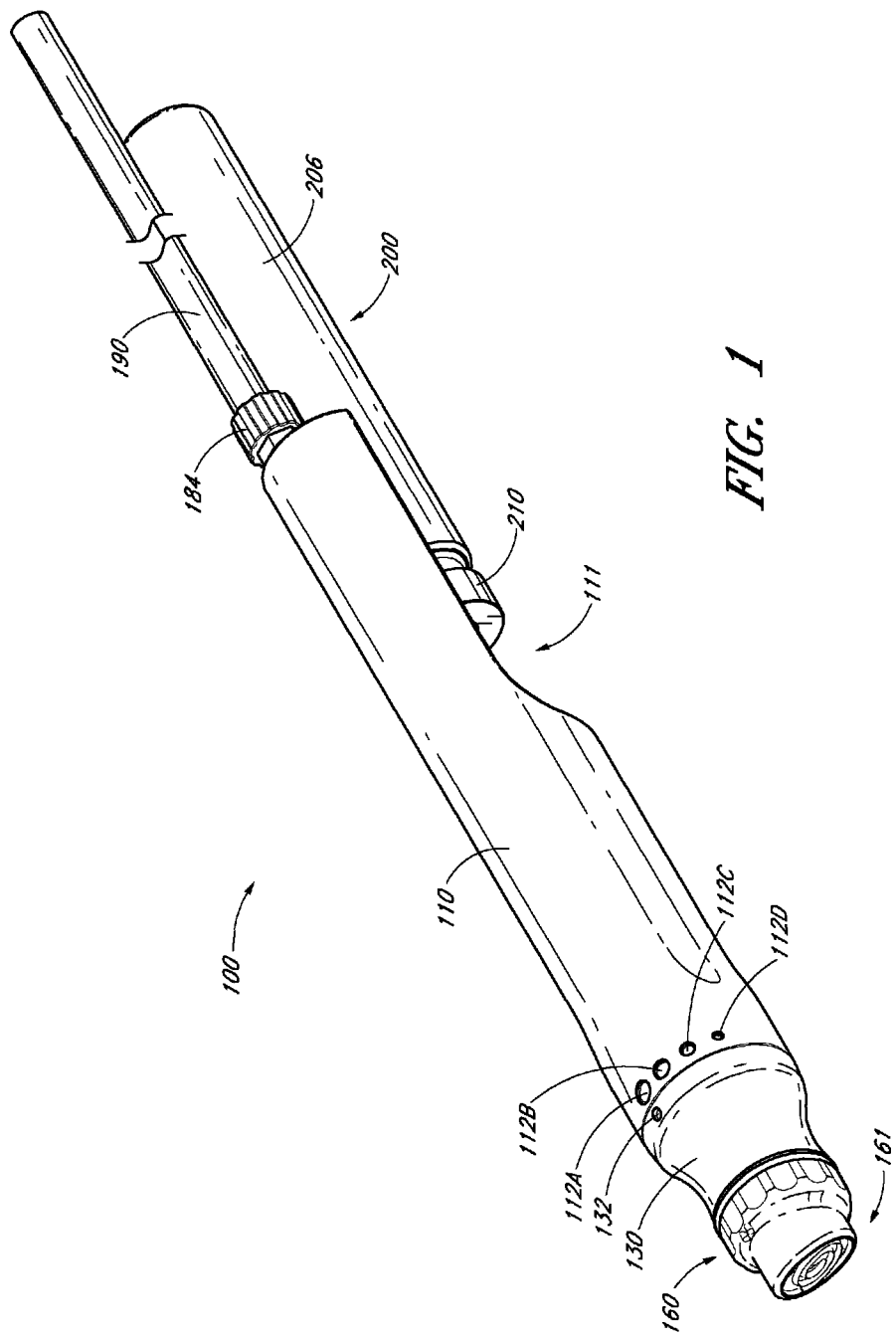
FIG. 1 illustrates a perspective view of a handpiece assembly configured for use with a skin treatment system according to one embodiment.

FIG. 1 illustrates one embodiment of a handpiece assembly 100 configured for use with a skin treatment system. Although the various embodiments of a handpiece assembly, a tip and related components have specific relevance to a skin treatment system, the features, advantages and other characteristics disclosed herein may have direct or indirect applicability in other applications, such as, for example, other medical devices, mechanical devices and/or the like. As shown, the handpiece assembly 100 can include a main body portion 110, an adjustable distal portion 130 and a tip 160. In addition, as illustrated in the depicted embodiment, the handpiece assembly 100 can include one or more connections that are configured to transfer fluids or other materials to and/or from the working end of the assembly 100. For example, as discussed in greater detailed herein, the handpiece assembly 100 can be in fluid communication with a waste conduit 190 that is adapted to remove exfoliated skin, serums, salicylic acid, other anti-acne acids and materials, microcapsules, capsules, other time-release products and substances, other fluids or materials and/or the like from the working surface.

With continued reference to FIG. 1, the handpiece assembly 100 can be advantageously configured to receive a cartridge 200. In some embodiments, the cartridge 200 comprises human growth factors, cytokines, soluble collagen, antioxidants, matrix proteins, serums, salicylic acid, other anti-acne acids and materials, microcapsules, capsules, other time-release products and substances (e.g., capsules, microcapsules, etc.), water (e.g., distilled, tap water, filtered, etc.), saline, other dilutants or dissolvents, vitamins, chemical exfoliation agents, lotions, soothing agents, brightening or lightening agents (e.g., kojic acid), peptides, acids, anesthetics, medicants, other non-active or active compounds, other fluids or materials, combination or mixtures thereof and/or any other substance. As discussed in greater detail herein, such materials can be selectively delivered to a user's skin while the handpiece assembly 100 is being used. In some embodiments, the handpiece assembly 100 includes an adjustable valve or other flow control feature to enable a user to regulate the rate of delivery of such fluids or other materials to the treatment surface.

In alternative embodiments, such as, for example, those discussed herein with reference to FIGS. 11-16, 19A, 19B, 20A-20D, 21A, 21B and 24-48, one or more materials can be strategically embedded, impregnated, placed, stored and/or otherwise disposed on one or more surfaces or areas of the tip or other portion or component of the skin treatment system (e.g., the foam pads of FIG. 19A-20B). Such materials can comprise solids, semi-solids, other dried substances, gels, concentrated solutions and/or the like. For example, such materials can be provided in loose form (e.g., positioned on or within a recess, other portion of the tip, within a cartridge or other container, adhered to one or more surfaces, etc.), as a tablet, capsule, pill, disc or other dissolvable solid, saturated within a foam pad or other sponge-like material and/or the like. Thus, in certain arrangements, water (e.g., distilled, tap water, filtered, etc.), saline, other dilutants and/or other fluids which are delivered to the tip can selectively dissolve, liquefy, melt, soften, dilute or otherwise prepare the materials embedded, impregnated and/or otherwise positioned on the tip, within a cartridge or other container and/or on or within another portion or component of a skin treatment system (e.g., handpiece assembly, fluid line upstream of the handpiece assembly, etc.). Accordingly, the desired human growth factors, cytokines, soluble collagen, antioxidants, matrix proteins, serums, salicylic acid, other anti-acne acids and materials, microcapsules, capsules, other time-release products and substances, peptides, amino acids, UVA and/or UVB sunblocks, other sunblocking agents, skin tightening agents, hyaluronic acid (HA), other hydration agents, hair removal or hair growth suppression agents, medicaments and pharmaceuticals, water, saline, other dilutants or dissolvents, vitamins, chemical exfoliation agents, lotions, soothing agents, skin brightening or lightening agents, other acids, anesthetics, medicants, other non-active or active compounds, other fluids or materials, combination or mixtures thereof and/or any other substance can be advantageously provided to the skin surface being treated, as desired or required.

In addition, as illustrated in FIG. 1, the handpiece assembly 100 can be connected to a vacuum. For example, the waste conduit 190 of the handpiece assembly can be placed in fluid communication with a suction source in order to remove exfoliated skin, spent fluids, waste materials and/or other substances away from the treatment surface. According to certain arrangements, the handpiece assembly 100 is configured to receive one or more removable tips 160, which may be selected based upon the specific procedure being performed, the desired result and/or any other considerations. Additional details regarding removable tips are provided with reference to certain embodiments disclosed herein.

Figure 2A:
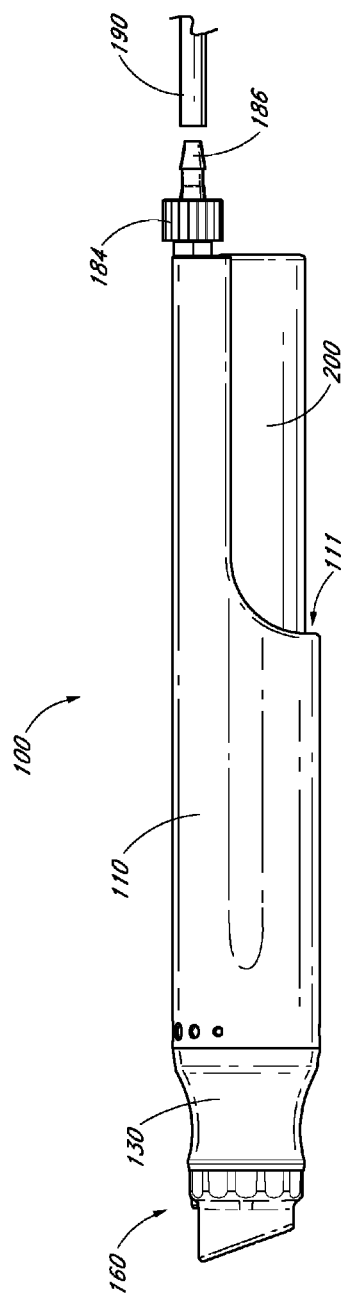
FIG. 2A illustrates a side view of the handpiece assembly of FIG. 1.
Figure 2B:
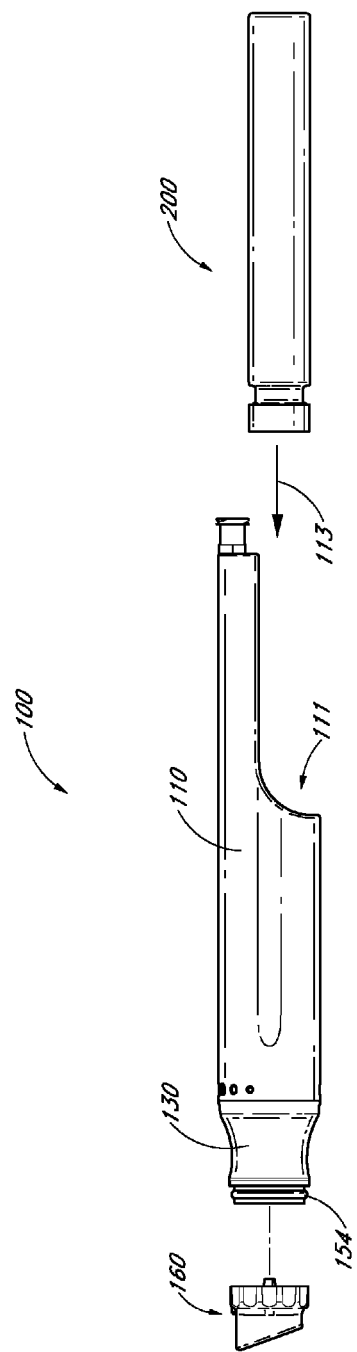
FIG. 2B illustrates an exploded side view of the handpiece assembly of FIG. 1.

With reference to FIGS. 2A and 2B, the handpiece assembly 100 can comprise a recess 111 along the main body portion 110. Such a recess 111 or other region can be sized, shaped and otherwise adapted to receive a cartridge 200. In any of the embodiments described herein, the cartridge 200 can include, without limitation, a standard or non-standard vial, ampoule or any other container. As discussed in greater detail herein, the handpiece assembly 100 can be configured to secure the cartridge 200 or other container within the recess 111 or any other area during use. In some embodiments, serums, salicylic acid, other anti-acne acids and materials, microcapsules, capsules, other time-release products and substances, other fluids and/or other materials contained within the cartridge 200 can be drawn toward the tip 160 using one or more suction sources (e.g., the vacuum source configured to remove waste materials from the tip 160). In other embodiments, the fluids and/or other materials contained within the cartridge gravity flow toward the tip 160 or are conveyed with the help of a fluid transfer device. The cartridge 200 can be selectively removed from the handpiece assembly 100 when a desired volume or other amount of serum or other material has been delivered to the tip 160.

In other arrangements, two or more different cartridges 200 can be used during a skin treatment procedure. For example, a particular procedure may require the contents (e.g., serums, salicylic acid, other anti-acne acids and materials, microcapsules, capsules, other time-release products and substances, proteins, brightening or lightening agents, peptides, other fluids or substances, etc.) of two or more different cartridges 200. Thus, a user can load and/or unload a combination of cartridges 200 or other containers within a handpiece assembly 100 during a treatment procedure, either at the same time or sequentially (e.g., one after another). With continued reference to FIG. 2B, the cartridge 200 can be inserted into the recess 111 in a direction generally represented by arrow 113.

Figure 3A:
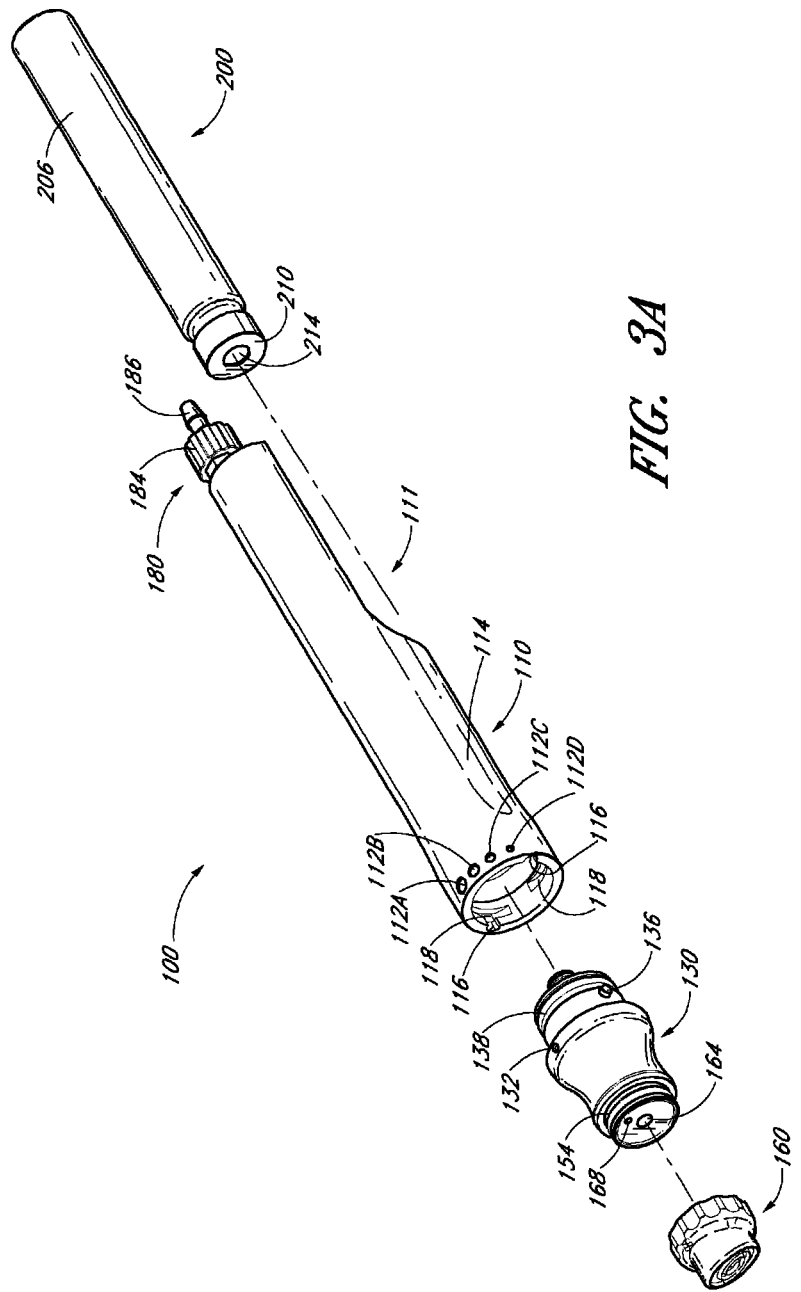
FIG. 3A illustrates an exploded perspective view of the handpiece assembly of FIG. 1.

FIG. 3A illustrates an exploded perspective view of one embodiment of a handpiece assembly 100 identical or similar to the one depicted in FIG. 1. As shown, the handpiece assembly 100 can comprise a main body portion 110 and an adjustable distal portion 130 rotatably attached thereto. As discussed and illustrated with reference to certain embodiments disclosed herein, rotation of the adjustable distal portion 130 relative to the main portion 110 can advantageously permit a user to regulate the flow of serums, other fluids, materials and/or the like being delivered from the container 200 to the tip 160 of the handpiece assembly 100.

As illustrated in FIG. 3A, the adjustable distal portion 130 of the handpiece assembly 100 can comprise one or more tabs 136 or other protruding members that are configured to align with corresponding recesses 116 or other features of the main body portion 110. In one embodiment, once the tabs 136 of the distal portion 130 are aligned with the recesses 116, the adjustable distal portion 130 can be moved toward the main body portion 110 until the tabs 136 reach a recessed annular ring 118. Consequently, the distal portion 130 can be rotated relative to the main body portion 110 so that the tabs 136 slide or otherwise move within the recessed annular ring 118 of the main body portion 110. Such a feature can help secure the adjustable distal portion 130 to the main body portion 110. As discussed in greater detail herein, rotation of the adjustable distal portion 130 relative to the main body portion 110 can help regulate the flowrate of fluids or other substances from a cartridge 200 to the tip 160 of the handpiece assembly 100. In other arrangements, the main body portion 110 comprises one or more other protruding members or features, and the adjustable distal portion 130 comprises corresponding recessed or other receiving areas or portion. Alternatively, one or more other interconnecting members or features can be used to secure the main body portion 110 to the adjustable distal portion 130.

In the embodiment illustrated in FIG. 3A, the distal portion 130 comprises one or more O-rings 138 or other sealing members to prevent undesirable leaks between the main body portion 110 and the adjustable distal portion 130. Further, the opposite end of the adjustable distal portion 130 can be shaped, sized and otherwise configured to receive a tip 160. In some embodiments, the tips 160 are removable, allowing a user to select between different tip designs, as desired or required by a particular application or use. In alternative arrangements, however, the tip 160 is permanently or semi-permanently attached to the handpiece assembly 100. Further, as shown in FIG. 3A, one or more O-rings 154 or other sealing members can be positioned between a tip 160 and the adjustable distal portion 130 of the handpiece assembly 100.

Figure 3B:
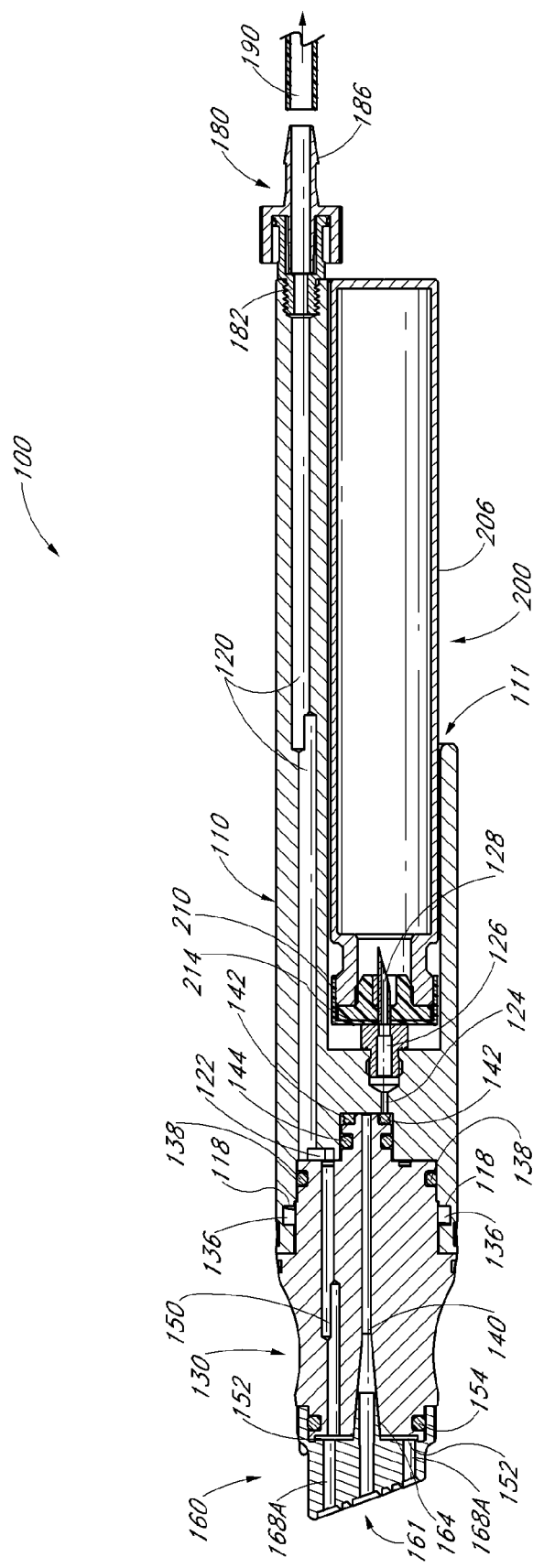
FIG. 3B illustrates a longitudinal cross-sectional view of the handpiece assembly of FIG. 1.

FIG. 3B illustrates a cross-sectional view of the handpiece assembly 100 depicted in FIG. 3A. In the illustrated embodiment, a cartridge 200 has been secured within a recess 111 or other receiving area of the handpiece assembly 100. The size, shape, location and/or other details of the recess 111 can vary, depending on the size of the cartridge 200 that will be inserted therein or as otherwise required or desired. As shown in FIG. 3A, the cartridge 200 can include a main cylindrical portion 206 and a nozzle portion 210. In some arrangements, the nozzle portion 210 comprises a septum 214, membrane or other member that can be pierced, punctured or otherwise compromised to access the interior contents of the cartridge 200 (e.g., serum, other liquids or materials, etc.). The septum 214 can include one or more flexible, rigid and/or semi-rigid materials, such as, for example, rubber, plastic, paper and/or the like.

The cartridge 200 can include one or more suitable materials, such as, for example, glass, metals (e.g., stainless steel), plastic, other synthetic or natural materials and/or the like. In some embodiments, for instance, a nozzle portion 210 comprising aluminum or other metal is crimped onto a glass main cylindrical portion 206 of the cartridge 200. However, the nozzle portion 210 and the main cylindrical portion 206 of the cartridge 200 can comprise any other materials. However, the nozzle portion 210 can be attached to the cylindrical portion 206 using one or more other methods or devices, such as, for example, a threaded connection, snap connection, adhesives, other fasteners and/or the like. In still other embodiments, the cartridge 200 may include more or fewer portions, compartments, features and/or the like, as desired or required.

With continued reference to FIG. 3B, the interior of the recess 111 of the handpiece assembly 100 can comprise a hollow spike 126 or other piercing member. As shown, the spike 126 can be sized, shaped, positioned and otherwise configured to penetrate the septum 214, membrane or other member of a cartridge 200 when a cartridge 200 is pushed sufficiently far within the recess 111. In other embodiments, the spike 126 or other member can be adapted to access an interior portion of a cartridge 200 in one or more other ways. Accordingly, once the cartridge 200 has been properly inserted into the handpiece assembly 100 and the septum 214 of the cartridge 200 has been compromised, the hollow spike 126 can be placed in fluid communication with the interior contents (e.g., human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance, etc.) of the cartridge 200. In other arrangements, as discussed in greater detail herein, the cartridge 200 can comprise water, saline, other dilutants or dissolvents and/or other fluids that can be selectively delivered to the tip 160 to dissolve, dilute and/or otherwise come in contact with one or more solids, granular materials, gels, concentrated solution and/or other substances positioned within, on and/or near the tip or other portion of a handpiece assembly.

In the illustrated embodiment, the spike 126 includes an angled or sloped tip 128 to further facilitate the piercing or puncturing of the cartridge's septum 214 or other sealing member. Although not illustrated herein, the handpiece assembly 100 can include one or more other needles that are configured to penetrate into the interior of a cartridge 200. For example, one or more vent needles can be used to facilitate the removal of fluids and/or other materials from a cartridge 200 which has been loaded into a handpiece assembly 100.

As discussed, the cartridge 200 can be sized, shaped and otherwise configured to snugly or generally snugly fit within the handpiece assembly 100. Therefore, in some arrangements, the cartridge 200 is secured to the handpiece assembly 100 by friction or by the generally tight tolerances of the recess 111 of the handpiece assembly 100. In FIG. 3B, the friction between spike 126 and the septum 214 or other sealing member can help maintain the cartridge 200 within the handpiece assembly 100.

In other embodiments, however, a cartridge 200 can be secured to one or more other portions of a handpiece assembly 100. In addition, the handpiece assembly 100 can include one or more other methods or devices for securing a cartridge 200. For example, the handpiece assembly 100 can include tabs, flanges, other protrusion members and/or any other features or items that help positively engage one or more portions of the cartridge 200 positioned therein. In some embodiments, delivery of a cartridge 200 to a desired depth of the recess 111 or other receiving area of the handpiece assembly 100 can produce an audible click, a positive engagement mechanism and/or the like. Such features can help notify the user that a cartridge 200 has been property secured within the handpiece assembly 100. In other arrangements, a separate device, such as, as a locking cap, strap or other member can be used to ensure that the cartridge 200 remains in fluid communication with the spike 126 and within the recess 111 or other desired receiving location of the handpiece assembly 100 during use.

Figure 4A:
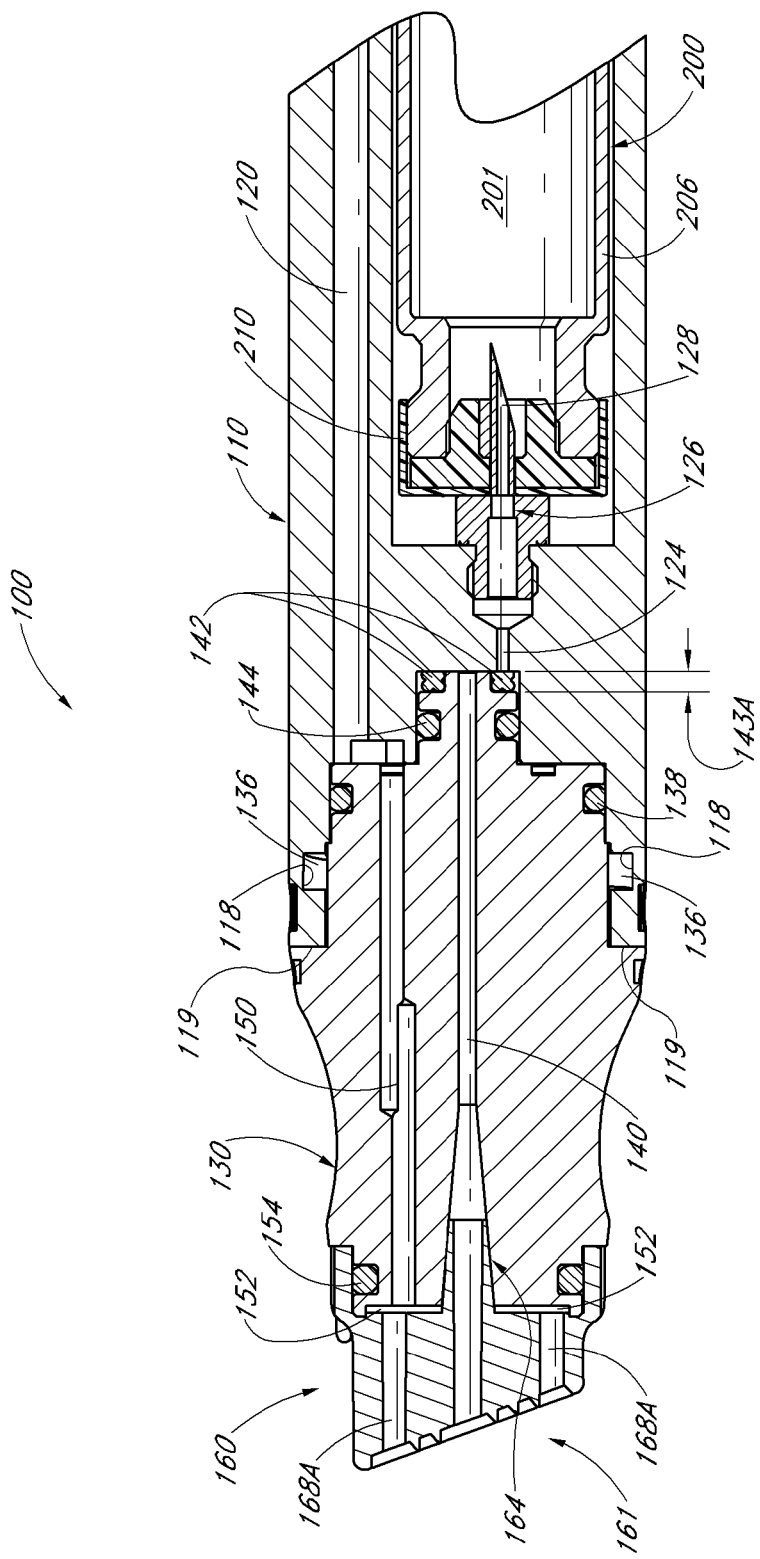
FIG. 4A illustrates a partial cross-sectional view of the handpiece assembly of FIG. 1 with an internal fluid delivery valve in a first position.

FIG. 4A illustrates a cross-sectional view of the handpiece assembly 100 comprising a spike 126 that is in fluid communication with the interior 201 of a cartridge 200. As shown, a delivery conduit 124 can be used to place the spike 126 in fluid communication with an intermediate region or space 142 generally formed between the main body portion 110 and the adjustable distal portion 130. One or more O-rings 144 or other sealing members can be used to ensure that fluid remains within this intermediate region 142. Further, the handpiece assembly 100 can be configured so that a user can selectively modify the size of the intermediate region 142. For example, as illustrated by the differences between FIGS. 4A and 4B, rotation of the adjustable distal portion 130 relative to the main body portion 110 can alter the width 143A, 143B of the intermediate region 142. In some embodiments, rotation of the adjustable distal portion 130 relative to the main body portion 110 causes the two portions 130, 110 to move closer to or further apart from each other, depending on the direction of rotation. Consequently, the width 143A, 143B, and thus the overall size, of the intermediate region 142 can be selectively varied by a user during a treatment procedure, as desired or required.

In some embodiments, the longitudinal axes of the delivery conduit 124 and the spike 126 can be offset (e.g., generally not aligned) with each other. This can permit the width 143A, 143B or other separation distance between the main body portion 110 and the adjustable distal portion 130 to be selectively varied. As discussed in greater detail herein, this can help modify the hydraulic characteristics of fluids and/or other materials being conveyed from the spike 126 to the delivery conduit 124, and thus, from a cartridge 200 or other fluid source to the tip 160 of the handpiece assembly 100. In some embodiments, the longitudinal axes of the delivery conduit 124 and the spike 126 remain offset as the adjustable distal portion 130 is rotated or otherwise moved relative to the main body portion 110.

In the illustrated embodiment, the distance between the recessed annular ring 118 of the main body portion 110 and the interface 119 between the main body portion 110 and the adjustable distal portion 130 varies depending on the circumferential position of the annular ring 118. In other words, by rotating the adjustable distal portion 130 relative to the main body portion 110, the distance between these portions 130, 110 can be selectively adjusted.

With continued reference to FIG. 4A, the adjustable distal portion 130 can include a delivery channel 140 or other conduit that places the intermediate region 142 in fluid communication with the tip 160. However, in order for serums or other materials to be delivered from the intermediate region 142 to the tip 160, a fluid path must be created between the intermediate region 142 and the delivery channel 140 through the adjustable distal portion 130. In FIG. 4A, there is little or no space between the distal portion 130 and the main body portion 110. Therefore, fluids or other materials will be prevented or severely limited from flowing from the intermediate region 142, and thus the cartridge 200, to the tip 160 of the handpiece assembly 100.

Figure 4B:
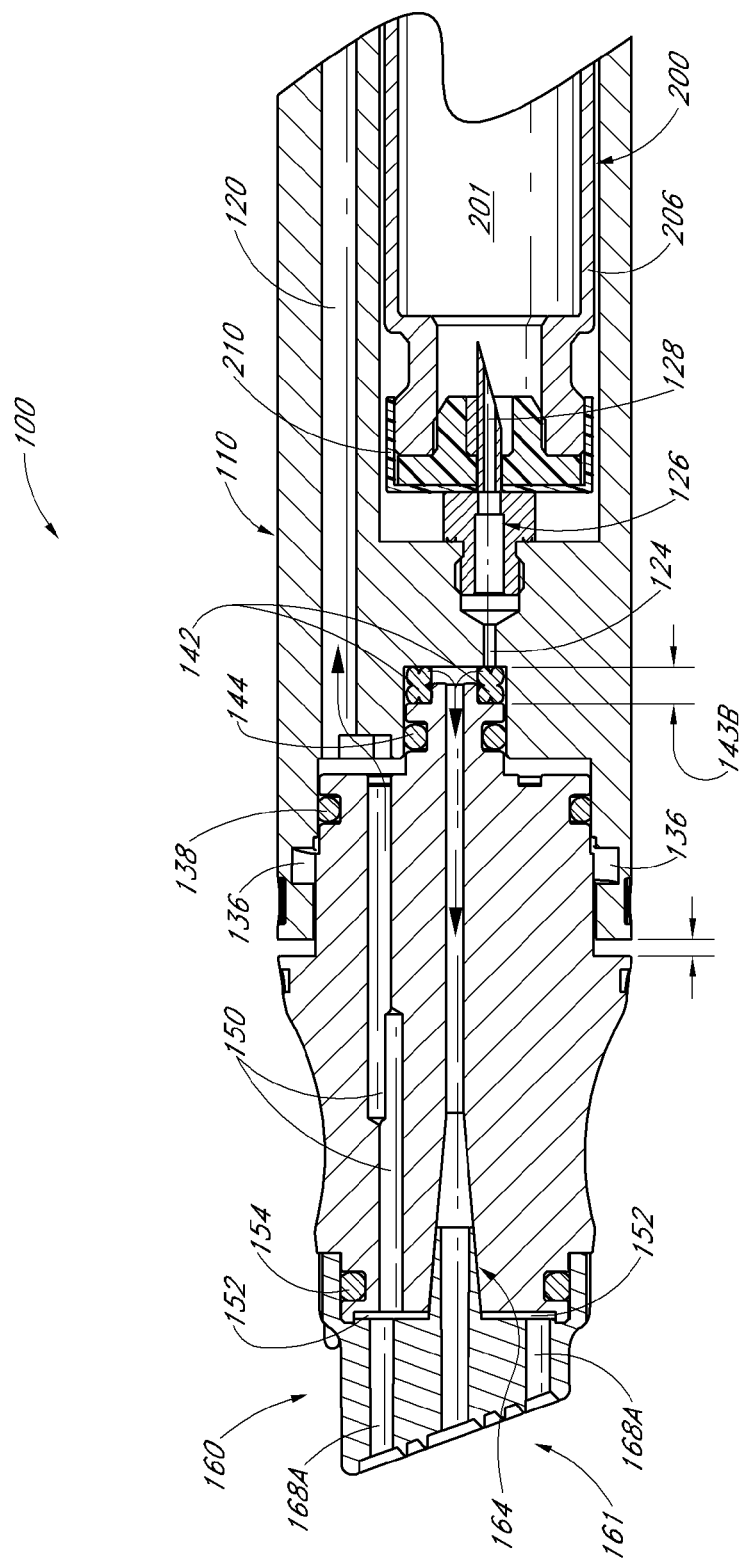
FIG. 4B illustrates a partial cross-sectional view of the handpiece assembly of FIG. 1 with an internal fluid delivery valve in a second position.

Alternatively, as illustrated in FIG. 4B, when sufficient separation exists between the adjacent surfaces of the adjustable distal portion 130 and the main body housing 110, a flow path is created from the intermediate region 142 to the delivery channel 140 of the distal portion 130. Accordingly, serums and/or other fluids or materials can be conveyed from the cartridge 200 toward the tip 160 of the handpiece assembly 100. Accordingly, by rotating the adjustable distal portion 130 relative to the main body housing 110, as discussed herein, the flowrate of liquids and/or other materials from the cartridge 200 toward the tip 160 can be selectively regulated.

With continued reference to FIGS. 1 and 3A, the adjustable distal portion 130 can include a setting indicator 132 along its exterior surface, near the interface of the adjustable distal portion 130 and the adjacent main body portion 110. Likewise, the main body portion 110 can include a plurality of corresponding markers 112A-112D with which the indicator 132 of the distal portion 130 can align. In the illustrated embodiment, the main body portion 110 comprises a total of four markers 112A-112D, each corresponding to a different flowrate setting through the handpiece assembly 100. However, a handpiece assembly 100 can include more or fewer indicators 132 and/or markers 112A-112D, as desired or required by a particular application or use. As discussed, rotation of the adjustable distal portion 130 relative to the main body portion 110 can vary the distance between the two portions 110, 130. Thus, the flow path for serums and/or other fluids or materials through the handpiece assembly 100 can be adjusted.

In the embodiment illustrated in FIGS. 1 and 3A, the markers 112A-112D along the outside of the main body portion are generally circular in shape. Further, the diameter of each of the markers 112A-112D varies depending on the relative flowrate through the handpiece assembly 100 to which each marker corresponds or relates. For example, in some embodiments, the larger markers represent a greater separation distance between adjacent surfaces of the adjustable distal portion 130 and the main body portion 110, and thus, a relatively higher flowrate of fluids and/or other materials from the cartridge 200 through the handpiece assembly 100 to the tip 160. As shown, the handpiece assembly 100 can be configured so that a user selects a flowrate setting by aligning the setting indicator 132 on the distal portion 130 with the desired marker 112A-112D on the main body portion 110. In accordance with the arrangements disclosed herein, this can be accomplished by rotating the adjustable distal portion 130 relative to the main body portion 110.

However, a handpiece assembly 100 can include one or more other methods of selecting a desired flowrate of fluids and/or other materials therethrough. For example, in some embodiments, the handpiece assembly 100 includes one or more dials, knobs, buttons and/or other devices or features for adjusting the flowrate. Such controllers can be graduated so as to permit a user to select a specific flowrate or relative flow setting (e.g., "HIGH," "MEDIUM," "LOW," etc.). In other arrangements, the handpiece assembly 100 comprises a display (e.g., LED, LCD, etc.) that is adapted to provide information regarding a current flowrate or setting. Further, such a display can be configured to permit users to make flowrate adjustments (e.g., touchscreen display). Further, selection devices or features (e.g., knobs, buttons, dials, etc.) and/or displays can be positioned on the handpiece assembly 100. Alternatively, the controllers can be separate from the handpiece assembly. For example, such devices or features can be connected to the assembly through one or more hardwired and/or wireless connections (e.g., cable, Ethernet line, radio frequency, Bluetooth, Wi-Fi, etc.).

In other embodiments, a handpiece assembly 100 includes one or more different methods and/or devices for controlling the flowrate of fluids or other materials from a cartridge 200 toward the tip 160. For example, the handpiece assembly 100 can comprise different types of flow control valves or devices than those disclosed herein. Regardless of the exact flow control method or device used, it may be desirable to provide users with the ability to selectively regulate the rate at which serums, other fluids or materials and/or the like are delivered from a cartridge 200 to the tip 160 of the handpiece assembly 100. This can further enhance a particular skin treatment procedure by allowing a desired volume of fluids or other materials to be delivered to the treatment surface (e.g., skin-tip interface). For instance, during the initial exfoliation phase, a relatively high volume of serum or other lubricating fluids may be desired. However, during subsequent stages of a treatment procedure, a reduced flowrate of fluids and/or other substances may be desired or required.

With continued reference to FIG. 3B, the tip 160 can include an internal delivery stem 164 or other conduit that is configured receive fluids and/or other substances from the delivery channel 140 of the adjustable distal portion 130 and convey them to the distal end 161 of the tip 160. As illustrated in FIGS. 3B, 4A and 4B, the internal stem 164 of the tip 160 can be sized, shaped and otherwise configured to be in fluid communication with the delivery channel 140 extending through the interior of the distal portion 130. In some embodiments, a handpiece assembly 100 includes two or more internal delivery channels 140 or other conduits through which fluids and/or other materials may be conveyed. Likewise, the tip 160 can include additional delivery stems 164 or other conduits configured to transfer fluids and/or other materials toward the distal end 161 of the tip 160.

As depicted in FIG. 3B, the tip 160 can include one or more removal conduits 168A. According to certain embodiments, such conduits 168A are also in fluid communication with the distal end 161 of the tip 160. The removal conduits 168A can be advantageously sized, shaped, located and otherwise configured to transfer exfoliated skin, spent serums and other waste materials away from the treatment surface. In some arrangements, a tip 160 comprises a plurality of removal conduits 168A located at or near the tip periphery. However, in other embodiments, the quantity, spacing, location and other details of the removal conduits 168A can vary, as desired or required by a particular application or use.

With continued reference to the cross-sectional views of FIGS. 3B, 4A and 4B, exfoliated skin, spent serums, other fluids and/or any other materials can be transferred from the distal end 161 of the tip 160 to a common collection area 152 located at or near a proximal end of the tip 160. According to some embodiments, the collection area 152 is positioned at or near the location where the tip 160 attaches to the adjustable distal portion 130. Accordingly, exfoliated skin, spent or waste fluids and/or other materials can be delivered into one or more removal channels 150 of the distal portion 130. In addition, the main body portion 110 can include one or more waste channels 120 or conduits that are configured to be in fluid communication with the removal channels 150 of the distal portion 130. In the depicted embodiments, a cavity 122 or other common area is used to place the channels 120 of the main body portion 110 in fluid communication with the removal channels 150 of the distal portion 130. Such a cavity or other common area can be located at or near the interface of the adjacent portions 110, 130 of the handpiece assembly 100. Further, the cavity 122 can be advantageously configured to maintain the waste channel 120 in fluid communication with the removal channel 150 throughout the entire range of relative movement between the main body portion 110 and the adjustable distal portion 130. As shown, the cavity 122 or other common area can comprise an annular region that completely or partially extends around an interior portion of the handpiece assembly 100.

In some embodiments, the main body portion 110 of the handpiece assembly 100 includes a discharge nozzle 180 or port. As illustrated in FIG. 3B, the nozzle 180 can include a threaded portion 182 that attaches to the handpiece assembly 100. The nozzle can further include a fitting generally opposite of the threaded portion 182 that is shaped, sized and otherwise configured to receive tubing 190 or some other fluid line or conduit. The nozzle 180 can comprise a different shape, size or general design than illustrated in FIG. 3B. In addition, the nozzle 180 can be adapted to connect to the handpiece assembly 100 and/or tubing 190 (or fluid conduits) using other methods or devices. For example, the nozzle 180 can form a generally uniform structure with an adjacent portion of the handpiece assembly 100. According to another arrangement, the nozzle 180 includes a quick-connect fitting to facilitate connection to and/or removal from a waste conduit (e.g., rubber or other flexible tubing, hose or other line). Regardless of its exact shape, size, method of attachment and/or other characteristics or details, the nozzle 180 can be advantageously configured to place the handpiece assembly 100 in fluid communication with a vacuum or other suction source (e.g., via the tubing 180 or other conduit) that can selectively remove exfoliated skin, spent serums other fluids and/or any other materials away from the skin surface being treated.

According to some embodiments, the conduit 190 or other channel (e.g., flexible tubing or hose) to which the handpiece assembly 100 connect are in fluid communication with a vacuum or other suction source (e.g., pump, other fluid transfer device, etc.). Thus, exfoliated skin, spent fluids and/or other waste materials can be transported away from the distal end 161 of the tip 160 to a canister (not shown) or other waste source. The rate of transfer of such waste materials can depend on one or more factors, such as, for example, the setting of the vacuum or suction source, the characteristics (e.g., diameter, length, smoothness, etc.) of the various conduits or channels 168A, 150, 120, 180, 190 through which the waste materials are conveyed, the viscosity, density and other fluid properties of the waste materials and/or the like.

According to some embodiments, a handpiece assembly 100A can include a clamshell design. For example, in the arrangement illustrated in FIGS. 4C-4E, the housing of the handpiece assembly 100A comprises two halves 110A, 111A that are sized, shaped and otherwise configured to removably mate with one another. As shown in FIGS. 4C and 4D, the two portions 110A, 111A of the handpiece assembly housing can be secured to each other using screws 112A or other fasteners. Alternatively, the various portions of the housing can be secured to each other using any other attachment device or method, such as, for example, welds, adhesives, clips, tabs, rivets, press fit connections, friction fit connections, snap fit connections and/or the like.

Such a split configuration, in which the internal components are positioned between the two or more separate portions, can facilitate the manufacture and assembly of a handpiece assembly 100A. For example, the separate housing portions 110A, 11A can be advantageously manufactured using an injection mold or other molding or casting process (e.g., compression molding, thermoforming, etc.). This can permit the handpiece housing to be manufactured relatively inexpensively, quickly and efficiently. The housing can comprise any rigid or semi-rigid material, such as, for example, thermoplastic, metal, alloy and/or the like.

Figure 4E:
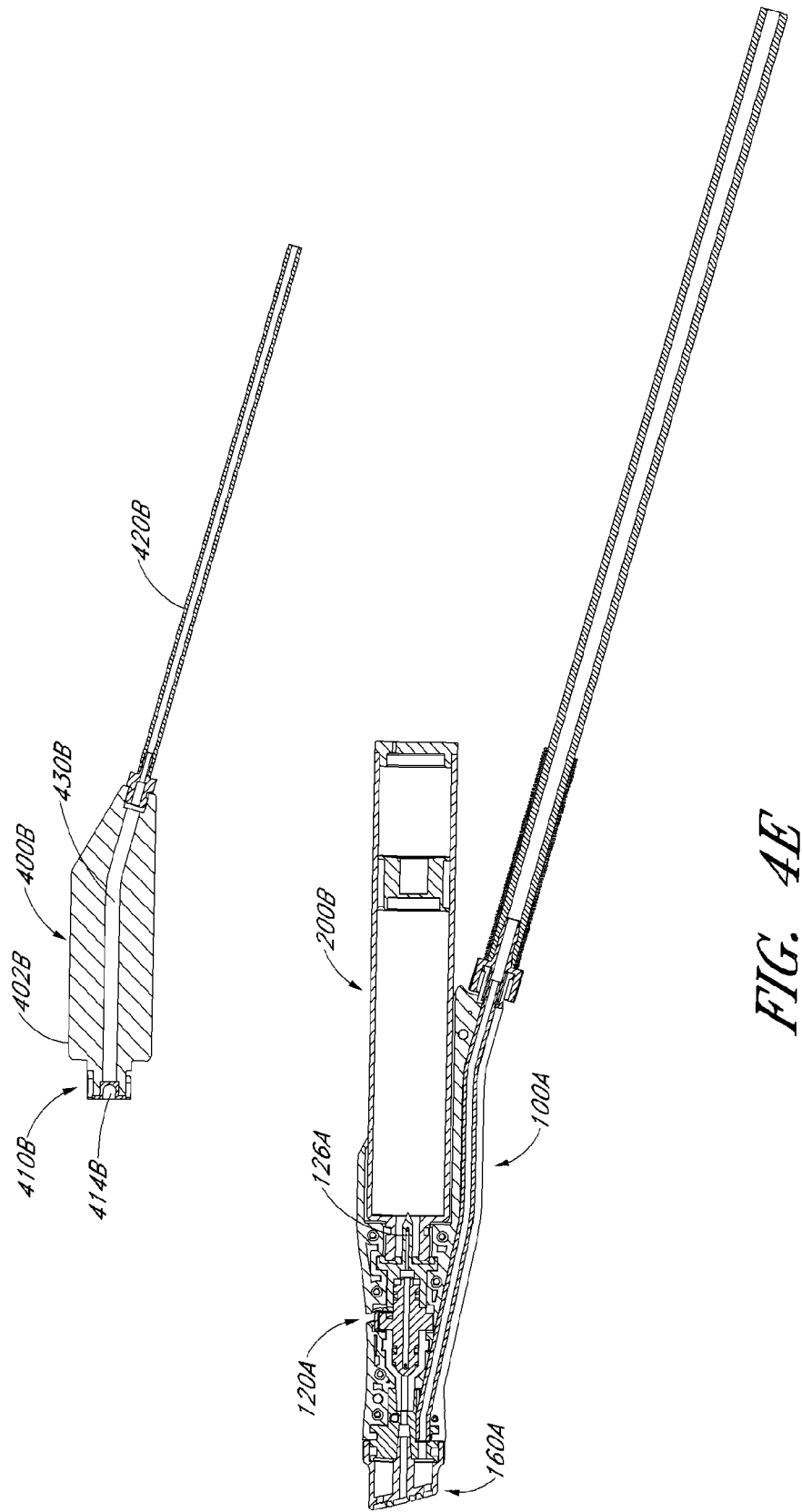
FIG. 4E illustrates a cross-sectional view of the handpiece assembly of FIGS. 4C and 4D.

As discussed herein, in some embodiments, the flow of serums, other fluids and/or any other materials from a cartridge 200B or other source through the handpiece assembly 100A can be regulated by the user using one or more valves. In FIGS. 4C-4E, the flowrate of such fluids and/or other materials through the handpiece assembly 100A can be controlled using a needle valve 120A or similar flow control device or feature. Therefore, according to some embodiments, the need to provide a housing having a movable portion that is configured to rotate relative to a stationary portion (e.g., FIGS. 1-4B) can be eliminated.

With continued reference to FIGS. 4C-4E, a user can easily adjust the delivery of serums and/or other fluids or materials toward the tip 160A by operating a handle or tab 122A of the valve 120A. As illustrated in FIGS. 4C and 4D, the handle or tab 122A is configured to rotate or otherwise move within a corresponding slot 123A of the handpiece housing. In some embodiments, the handle or tab 122A is resiliently biased (e.g., in the fully open position, in the fully closed position, an intermediate position, etc.), as desired or required. According to some arrangements, the use of such a needle valve or other valve assembly within the handpiece assembly 100A can simplify the overall design of the assembly 100A, allow for more accurate delivery of fluids and/or other materials through the handpiece assembly and/or provide one or more other benefits or advantages. Such a needle valve with an external handle or controller can be incorporated into any of the embodiments disclosed herein, including, for example, the handpiece assemblies discussed herein with reference to FIGS. 24-48. For example, as discussed in greater detail below, a needle valve or other flow control feature 3822' can be included in the handpiece assembly illustrated in FIG. 42.

As illustrated in FIG. 4E, the handpiece assembly 100A can be configured to receive a removable cartridge 200B within its recessed proximal portion. Alternatively, the handpiece assembly 100A can be adapted to receive a supply cartridge 400B that is in fluid communication with one or more separate fluid and/or other material sources. For example, the supply cartridge 400B can include a fluid line 420B that is connected to a larger fluid supply (e.g., a bottle, reservoir, etc.), a manifold and/or the like. Thus, fluids and/or other materials can be easily and conveniently delivered into and through the handpiece assembly 100A using such a supply cartridge 400B. The use of supply cartridges 400B can reduce the frequency of replacing separate cartridges 200B within the handpiece assembly.

With continued reference to FIG. 4E, the supply cartridge 400B can include a main body portion 402B that is sized, shaped and otherwise configured to fit within a corresponding recess of the handpiece assembly 100A. The distal end of the cartridge 400B can include a head or neck 410B portion that is adapted to receive the puncturing spike 126A of the handpiece assembly 100A when properly inserted therein. In any of the embodiments disclosed herein, or equivalents thereof, a supply cartridge or any other cartridge configured for placement within a handpiece assembly can include a check valve (or other one-way valve) 414B, a septum and/or the like. For example, as illustrated in FIG. 4E, the head 410B of the supply cartridge 400B comprises a one-way valve 414B that helps prevent fluids and/or other materials from leaking out of the internal passage 430B of the cartridge 400B when the cartridge 400B is removed from the handpiece assembly 100A. In some embodiments, such a one-way valve 414B is held in place using an adjacent septum or other securement member or feature.

Figure 4F:
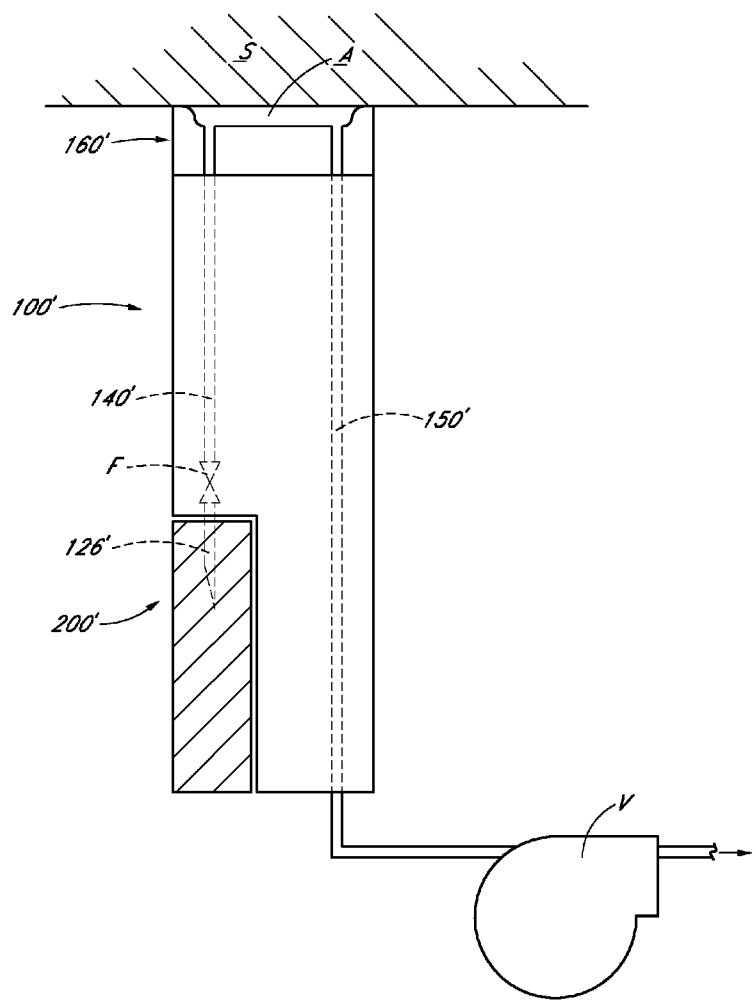
FIG. 4F schematically illustrates a handpiece assembly which comprises a cartridge and which is in fluid communication with a vacuum source according to one embodiment.

FIG. 4F schematically illustrates one embodiment of a handpiece assembly 100' which comprises a cartridge 200' and which is in fluid communication with a vacuum V or other suction source. In the depicted arrangement, the vacuum V is configured to remove waste materials from the tip 160' and help deliver serums, other fluids and/or any other materials from the cartridge 200' to the tip 160'. When the tip 160' is positioned against the skin S being treated, suction created by the vacuum source V can be transmitted to the delivery channel 140' of the assembly 100'. In some embodiments, such a suction force within the delivery channel 140' remains intact as long as the tip 160' is maintained against or substantially against the skin S. Consequently, the suction force can be transferred to the delivery channel 140' via an enclosed or substantially enclosed area A near the working surface of the tip 160'.

With continued reference to FIG. 4F, human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents (e.g., kojic acid), peptides, peeling agents, acids, anesthetics, medicants, other non-active or active compounds, other fluids or materials, combination or mixtures thereof and/or any other substance situated within a cartridge 200' can be placed in fluid communication with the delivery channel 140' using a spike 126' or other member. A valve F or other flow control device or mechanism can be used to regulate the rate at which such fluids and/or other materials are transferred to the tip 160'. For example, the handpiece assembly 100' can comprise a main body portion that is movable (e.g., rotatable) relative to a distal portion as disclosed herein with reference to FIGS. 1-3B and 5A. As discussed, the relative movement of these portions can help regulate the flowrate of serums, other fluids and/or other materials from the cartridge 200' to the tip 160' of the handpiece assembly 100'. In alternative embodiments, as discussed in greater detail herein, the delivery channel 140' can be configured to convey water, saline, other dilutants or dissolvents and/or other fluids from the cartridge 200' to the tip 160'. Accordingly, solid materials, gels, other concentrated materials and/or other substances positioned on or near the tip 160' can be advantageously mixed or combined with these fluids to produce a desired and/or required effect.

In other embodiments, however, the contents of a container 200' are transferred to the tip 160' using one or more other methods or devices, either in addition to or in lieu of the methods discussed herein with reference to FIG. 4F. For example, the handpiece assembly 100' can comprise an internal pump or other fluid transfer device that is configured to convey serums, other fluids and/or other materials from the cartridge 200' to the tip 160'. In other embodiments, the internal contents of the cartridge 200' are configured to, at least partially, gravity flow toward the tip 160' of the assembly 100'. One or more other ways of transferring fluids and other materials to the tip 160' of the handpiece assembly 100' can be used, either in lieu of or in combination with methods and devices disclosed herein.

In any of the embodiments of a handpiece assembly disclosed herein, including but not limited to those illustrated and discussed with reference to FIGS. 1, 2A, 2B, 3A, 3B, 4A-4F, 5A-5C, 7, 14A, 16A, 17, 18A, 18B, 19A, 19B, 20A-20D, 21A and 21B, or variations thereof, the direction of flow through the various channels, conduits and/or other hydraulic components of the tip, handpiece assembly and other components of a skin treatment system can be reversed. By way of example, in the arrangement shown in FIGS. 1-4B, the handpiece assembly 100 can be differently configured so that spent fluids, exfoliated skin, debris and other waste materials are removed away from the skin through a centrally located opening in the tip (e.g., the delivery stem 164) and/or a centrally located channel (e.g., the delivery channel 140) of the handpiece assembly 100. In such embodiments, one or more of the fluid channels, connectors and/or other fluid lines may need to be reconfigured to adequately place the centrally-located removal opening of the tip in fluid communication with a vacuum or other suction source, as desired or required.

Further, the serums, other fluids and/or other materials can be delivered to the tip 160 (e.g., from a cartridge, an external source, etc.) through one or more peripheral or other non-centrally located channels, conduits and/or other lines or fittings. For instance, in the handpiece assembly 100 illustrated in FIGS. 1-4B, such fluids and/or other materials can be routed through channels 150 of the assembly and/or waste conduits 168A of the tip 160. Thus, one or more of the channels, connectors and/or other hydraulic components may need to be reconfigured to adequately place the non-centrally located delivery openings of the tip in fluid communication with corresponding delivery lines of the handpiece assembly 100.

Accordingly, in any of the embodiments disclosed herein, water (e.g., distilled, tap water, sterile, filtered, etc.), saline, serums, salicylic acid, other anti-acne acids and materials, microcapsules, capsules, other time-release products and substances, growth factors, other dilutants, other solutions, mixtures or fluids and/or the like can be delivered to the tip through one or more centrally and/or non-centrally located (e.g., peripheral, offset, etc.) openings. Thus, the flow pattern of such fluids and/or other materials across the tip (e.g., from the tip inlet to the tip outlet) can be advantageously controlled as desired or required for a particular application or use. For instance, in some embodiments, it may be desirable to introduce fluids and/or other materials through one, two or more peripheral or non-centrally located openings (e.g., 572A, 572B) of a tip (e.g., 560 of FIG. 8A), and to collect the spent fluids, removed skin, other debris and other waste materials through a centrally-located opening (e.g., 570).

Figure 5A:
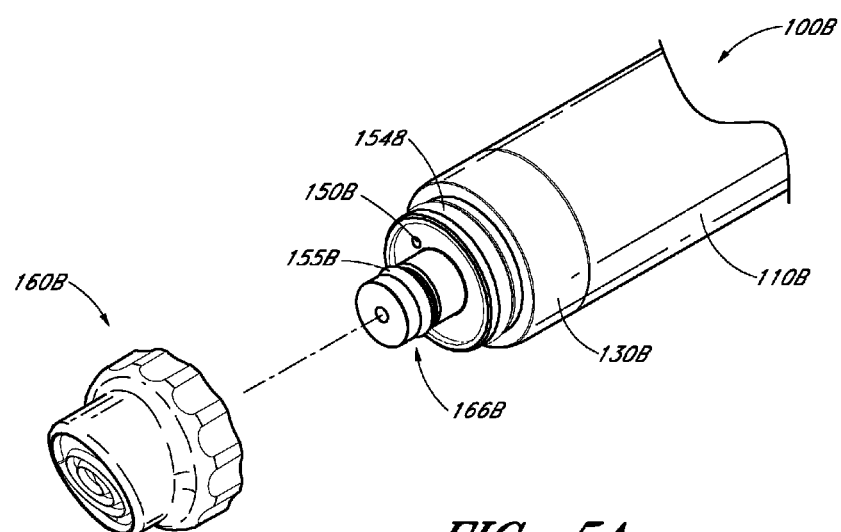
FIG. 5A illustrates an exploded perspective view of a handpiece assembly according to another embodiment.

FIG. 5A illustrates a partial exploded view of another embodiment of a handpiece assembly 100B. As with the arrangement of FIG. 3A, the depicted handpiece assembly 100B can be configured to receive a removable tip 160B along its distal end. Further, as with other embodiments discussed and illustrated herein, the handpiece assembly 100B can include an adjustable distal portion 130B that is selectively movable (e.g., rotatable) relative to the adjacent main body portion 110B. Such relative rotation or other movement can advantageously permit a user to regulate the flow of serums, salicylic acid, other anti-acne acids and materials, microcapsules, capsules, other time-release products and substances, chemical exfoliation compounds or mixtures, antioxidants, growth factors, lotions, vitamins, medicants, brightening or lightening agents, peptides, peeling agents, acids, other active or non-active agents, water (e.g., distilled, tap water, filtered, sterile, etc.), saline, other dilutants, other fluids or materials and/or the like being delivered to the tip 160B of the handpiece assembly 100B.

Figure 5B:
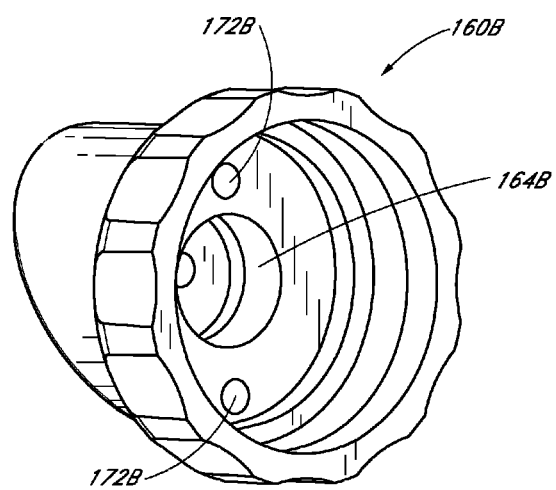
FIG. 5B illustrates a bottom perspective view of one embodiment of a tip configured to be secured to the handpiece assembly of FIG. 5A.

In FIG. 5A, the adjustable distal portion 130B of the handpiece assembly 100B comprises a nozzle 166B or other member that helps place the tip 160B in fluid communication with a vacuum source and/or a fluid delivery source. In some embodiments, the tip 160B is advantageously designed to receive or otherwise accommodate the nozzle 164B. For example, as illustrated in FIG. 5B, an interior portion of the tip 160B can include a recess 164B that is shaped, sized and otherwise configured to receive the nozzle 166B of the adjustable distal portion 130B. As shown, the handpiece assembly 100B and/or the tip 160B can include one or more O-rings 154B, 155B, gaskets and/or other sealing members or devices to help reduce or eliminate the likelihood of leaks as fluids and other materials are transferred between the handpiece assembly 100B and the tip 160B. The tip 160B can be secured to the distal end of the handpiece assembly 100B using a friction connection, a threaded connection, a snap connection, another type of mechanical connection and/or any other type of attachment device or method.

Such configurations in which the distal end of a handpiece assembly comprises a nozzle, fitting or other protruding member that is adapted to be secured within a corresponding recess, other feature or other area of the tip can be incorporated into any of the handpiece assembly and/or tip embodiments disclosed herein, or variations thereof. As discussed in greater detail herein, such a nozzle-recess connection can be configured to place the tip in fluid communication with either a suction source or a fluid delivery source, as desired or required. One or more additional openings, conduits, channels and/or other hydraulic components in the tip and/or the handpiece assembly can be configured to transfer fluids and/or materials to and/or from the tip.

Figure 5C:
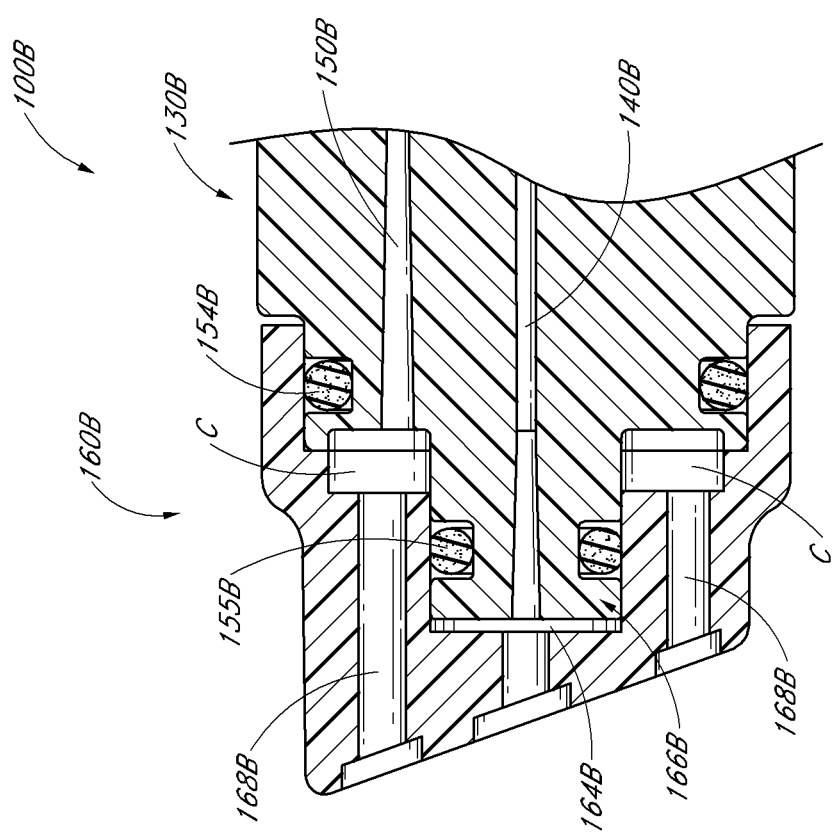
FIG. 5C illustrates a cross-sectional view of the handpiece assembly and the tip of FIG. 5A.

With reference to the cross-sectional view of FIG. 5C, once the tip 160B has been properly secured to the handpiece assembly 100B (e.g., to the adjustable distal portion 130B), the distal end of the tip 160B can be placed in fluid communication with one or more delivery channels 150B and/or waste channels 140B of the handpiece assembly 100B. For example, in the embodiment depicted in FIG. 5C, serums, salicylic acid, other anti-acne acids and materials, microcapsules, capsules, other time-release products and substances, water (e.g., distilled, tap water, filtered, etc.), other dilutants, other fluids or materials and/or the like can be delivered to the tip 160 through a delivery conduit 150B of the handpiece assembly 100B, through a common area C (e.g., located between the tip 160B and the adjustable distal portion 130B of the handpiece assembly 100B) and through two peripherally located delivery conduits 168B of the tip 160B. In addition, waste materials can be removed from the tip through a centrally-located opening and recess 164B of the tip 160B and a waste channel of the handpiece assembly 100B. However, as discussed, in alternative embodiments, the direction of flow through such channels, conduits and/or other hydraulic components of the tip 160B and/or the handpiece assembly 100B can be reversed or otherwise varied, as desired or required.

FIG. 6A illustrates a side view of one embodiment of a cartridge 300 configured to be secured within or onto a handpiece assembly as disclosed herein. The cartridge 300 can include a main cylindrical portion 306 and a nozzle portion 310 or closure. As illustrated in FIG. 6C, the closure 310 can comprise a septum 314, membrane or other member that can be pierced, punctured or otherwise compromised to access the interior contents of the cartridge 300 (e.g., serum, other liquids or materials, etc.). In some embodiments, for example, the septum 314 or other member is adapted to be selectively pierced or punctured by a hollow spike, needle or similar device when the cartridge 300 is inserted into the handpiece assembly. As discussed, the septum 314 can include one or more flexible materials, such as, for example, rubber, plastic, paper and/or the like.

For any embodiments of a cartridge, vial or other container disclosed herein, the septum 314, membrane or other surface configured to be pierced, punctured or otherwise compromised can be re-sealable. In other words, such a septum 314 can be adapted to re-seal the internal contents of the cartridge 300 when the cartridge is removed from the handpiece assembly. Therefore, leakage of serums, other fluids and/or other materials contained within a cartridge can be reduced or prevented. In addition, the septum 314 can help ensure against contamination of the internal contents by preventing one or more materials from entering the cartridge.

As discussed, cartridges configured to be secured within a handpiece assembly can include any combination of serums, salicylic acid, other anti-acne acids and materials, microcapsules, capsules, other time-release products and substances, human growth factors, cytokines, collagen, brightening or lightening agents, peptides, peeling agents, acids, antioxidants, matrix proteins, saline, water (e.g., distilled, tap water, filtered, etc.) and/or other liquids or substances, as desired or required by a particular application or use. In certain embodiments, a treatment protocol may require the use of one, two or more different cartridges for a specific procedure. Thus, cartridges can be removed from or inserted into a handpiece assembly prior to or during a particular procedure.

Another embodiment of a cartridge 400 that is sized, shaped and otherwise configured for placement within a handpiece assembly is illustrated in FIG. 6B. As shown, the cartridge 400 can include a tip 410 and a main tubular portion 406. With reference to the front view of FIG. 6D, at least a portion of the end surface 414 of the tip 410 can include one or more septa, membranes or other layers or members that are configured to be pierced, punctured or otherwise compromised by a spike or other protruding member when the cartridge 400 is secured in a handpiece assembly.

With continued reference to FIG. 6B, the cartridge 400 can include an internal channel 420 that is adapted to be in fluid communication with a tubular spike or other protruding member of the handpiece assembly when a surface 414 of the cartridge 400 is pierced or punctured (e.g., when the cartridge 400 is properly inserted within a handpiece assembly). In some embodiments, as illustrated in FIG. 6B, the cartridge 400 includes a nozzle 430 or other fitting that is sized, shaped and otherwise configured to receive or connect to a fluid line 450 or other conduit. For example, in the depicted arrangement, the nozzle 430 includes a port 438 to which tubing or some other fluid conduit 450 can attach. In some embodiments, the nozzle 430 is secured to the cartridge 400 using a threaded connection 434. However, one or more other types of methods or devices can be used to join the nozzle 430 to the cartridge 400. In other embodiments, the cartridge 400 and the nozzle 430 form a generally unitary structure (e.g., molded as a single member).

A cartridge 400, such as the one illustrated in FIG. 6B, can advantageously permit a user to deliver human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance to a handpiece assembly from one or more external fluid sources. For example, in some embodiments, the conduit 450 to which the cartridge 400 is connected, is placed in fluid communication with one or more containers. Such containers can comprise the desired serums, salicylic acid, other anti-acne acids and materials, microcapsules, capsules, other time-release products and substances, human growth factors, cytokines, collagen, antioxidants, matrix proteins, brightening or lightening agents, peptides, peeling agents, acids, medicants, other fluids or substances, combinations thereof and/or the like, as desired or required by a particular treatment. Thus, the cartridge 400 can be used as an interface between the handpiece assembly and a relatively larger source of treatment media. For example, the cartridge 400 can be placed in fluid communication with a multi-container system such as the one disclosed in U.S. patent application Ser. No. 11/392,348, filed on Mar. 29, 2006 and published on Jul. 5, 2007 as U.S. Publication 2007/0156124, the entirety of which is hereby incorporated by reference herein.

According to certain arrangements, a cartridge 400 includes one or more solids, granular materials, gels, concentrated fluids and/or other substances that are adapted to dissolve, dilute, soften or otherwise mix when contacted by water, saline, other dilutants or dissolvents and/or other fluids. Thus, such materials or other substances can be placed within the cartridge 400 in one or more forms, such as, for example, as powder, granular material, a tablet, a capsule, a pill, other dissolvable solid, a concentrated solution, a gel and/or the like. In other embodiments, such solids, gels and/or other materials can be situated on the tip or other portion of the system (e.g., within a post or recess, adhered to one or more other exposed or hidden surfaces, within a removable cartridge upstream of the handpiece assembly as illustrated, for example, in FIG. 18A, etc.), impregnated into a foam pad or other member (see, as depicted in FIGS. 19A, 19B and 20A-20C) and/or at any other location. Regardless of their exact composition, location and/or other details, such materials and/or other substances can be configured to dissolve, dilute and/or otherwise mix with water, saline and/or other fluids being conveyed through the cartridge 400.

As discussed, in any of the embodiments of the cartridge (e.g., vial, ampoule, other standard or non-standard container, etc.) disclosed herein, the cartridge can be configured to releasably lock or otherwise secure to one or more portions of a handpiece assembly (e.g., recess). In other embodiments, a cartridge includes threads, tabs, slots and/or other features that are configured to engage corresponding portions of the handpiece assembly. In alternative arrangements, the cartridge is adapted to remain within a receiving portion of the handpiece assembly by friction or some other mechanism or feature, as desired or required.

In any of the embodiments disclosed herein, a cartridge configured to be removably positioned within a corresponding recess of a handpiece assembly can comprise a piston or other movable member within its interior. Accordingly, the internal volume of the cartridge containing the fluid and/or other material to be selectively delivered to the handpiece assembly can be reduced as fluid and/or other material is expelled from the cartridge. This can help ensure that the internal portion of the cartridge that contains the serum, other liquid and/or other material to be delivered to the handpiece assembly does not include air or other gases. Thus, the treatment media can be consistently and reliably maintained at the distal end of the cartridge interior (e.g., toward the cartridge outlet) during a treatment procedure, regardless if and how a user tilts or otherwise maneuvers the handpiece assembly.

Figure 6E:
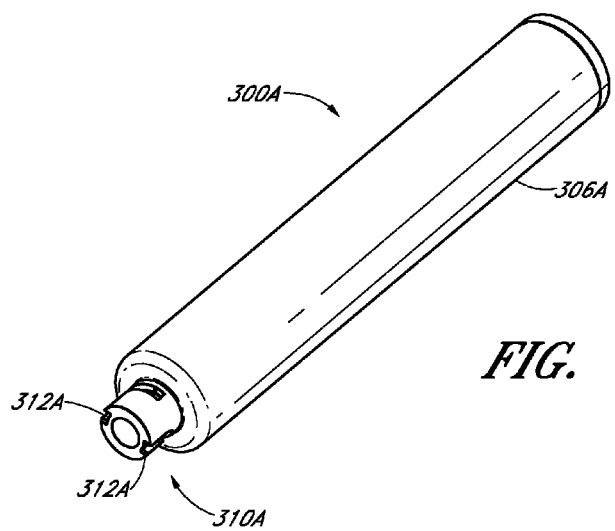
FIG. 6E illustrates a perspective view of one embodiment of a cartridge configured for placement within a handpiece assembly.
Figure 6F:
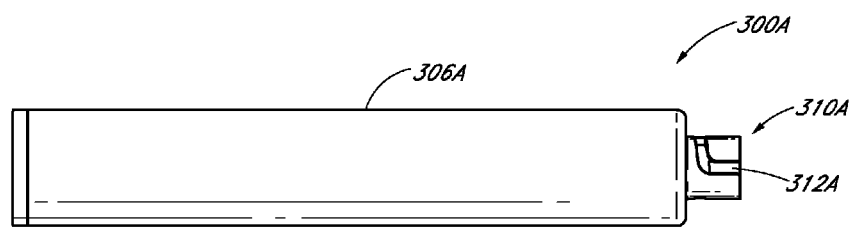
FIG. 6F illustrates a side view of the cartridge of FIG. 6E.
Figure 6G:
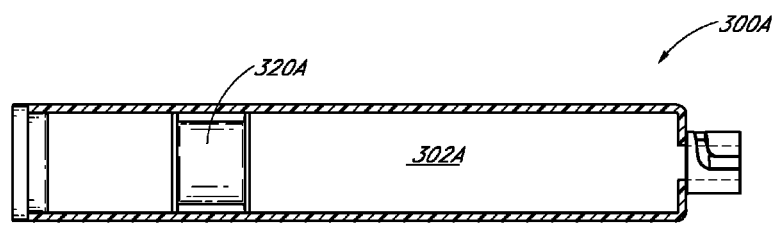
FIG. 6G illustrates a side view of the cartridge of FIG. 6E with the outer housing of the cartridge shown as transparent in order to view the internal contents of the cartridge.

One embodiment of a cartridge 300A having an internal piston 320A or other movable device is illustrated in FIGS. 6E-6G. As shown, the piston 320A can urge the internal contents of the cartridge 300A (e.g., serum, other treatment fluids or materials, etc.) toward the distal end 310A of the cartridge 300A. As noted above, the use of such an airless pump design can eliminate or reduce the likelihood that air or other gases will interfere with the consistent delivery of such fluids and/or other materials to the handpiece assembly.

With continued reference to FIGS. 6E-6G, the handpiece assembly 300A can additionally include a neck portion 310A that is advantageously configured to lockingly engage a corresponding portion of the handpiece assembly. For example, the neck portion 310A of the cartridge 300A can include slots 312 or recesses that are configured to mate and secure to corresponding protrusions within the interior of the handpiece assembly recess. Thus, once the cartridge 300A has been properly secured within the recess of handpiece assembly, the cartridge 300A can be rotated (e.g., quarter revolution, half revolution, etc.) or otherwise moved to lockingly secure the cartridge to the handpiece assembly. Such arrangements can ensure that the cartridge is not accidentally disconnected from the handpiece assembly during use. In order to remove the cartridge from the handpiece assembly, a user can rotate the cartridge in the opposite direction relative to the handpiece assembly to unlock or disengage the cartridge from the handpiece assembly. Any other temporary or permanent locking mechanism or feature can be used, either in lieu of or in addition to the recess or slots illustrated in FIGS. 6E-6G. Such features can be incorporated into any of the embodiments illustrated and discussed herein, or equivalents thereof.

Figure 7:
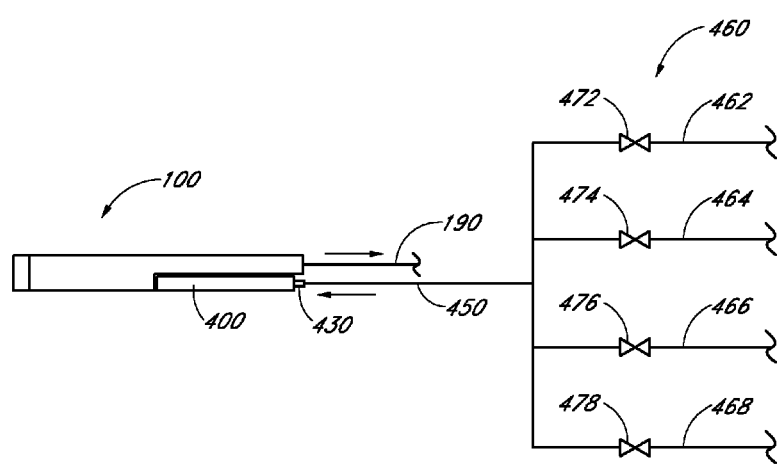
FIG. 7 schematically illustrates the cartridge of FIG. 6B positioned within a handpiece assembly and being in fluid communication with a fluid delivery system according to one embodiment.

According to certain embodiments, as illustrated in FIG. 7, the cartridge 400 is placed in fluid communication with a manifold system 460 that may comprise a plurality of individual fluid lines 462, 464, 466, 468. In turn, one or more of these fluid lines 462, 464, 466, 468 can be in fluid communication with a separate container (not shown). In the illustrated embodiment, all the individual fluid lines 462, 464, 466, 468 feed into the main fluid line 450, which connects to the nozzle 430 of the cartridge 400. One or more of the fluid lines 450, 462, 464, 466, 468 can comprise a valve 472, 474, 476, 478 or other flow control device or feature to selectively regulate the transfer of fluids and/or other materials to the handpiece assembly 100. In the illustrated arrangement, the manifold system 460 comprises a total of four fluid branches 462, 464, 466, 468. However, a system can comprise more or fewer fluid branches, as desired or required by a particular application.

According to certain embodiments, one or more of the fluid lines fluid lines 450, 462, 464, 466, 468 of the system schematically illustrated in FIG. 7 are configured to provide water (e.g., distilled, tap water, filtered, etc.), saline, other dilutants or dissolvents, other fluids and/or the like to the handpiece assembly 100. As discussed in greater detail herein, such fluids can be adapted to contact and dissolve, dilute, liquefy, soften and/or otherwise mix with one or more solids, gels and/or other materials positioned within or on various surfaces or portions of the handpiece assembly 100 (e.g., tip). This can provide a convenient method of providing one or more materials at the skin-tip interface and/or any other location where such materials are desired or required.

FIGS. 8A-8F illustrate different views of one embodiment of a removable tip 560 configured for placement on a handpiece assembly as disclosed herein. As shown, the tip 560 can include a tip body portion 563 and a tip skirt portion 562 extending along the bottom of the tip body portion 563. According to certain embodiments, the skirt portion 562 includes a plurality of gripping members or other features (e.g., recesses, protrusions, etc.) to facilitate the handling of the tip 560.

With reference back to the exploded perspective view of FIG. 3A, a tip 160 can be configured to slidably connect to the distal end of a handpiece assembly 100 (e.g., the end of the adjustable distal portion 130). For example, in some embodiments, the tip 160 is adapted to be press fit onto the handpiece assembly 100. As illustrated in FIG. 3A, one or more O-rings 154 or other sealing members can be used between adjacent surfaces of the tip 160 and the handpiece assembly 100 to prevent or reduce the likelihood of undesirable leaks or pressure (e.g., positive, negative or vacuum, etc.). In other embodiments, a tip 160 is removably secured to a handpiece assembly 100 using any other method or device, such as, for example, a threaded connection, interlocking tabs, flanges, members, other fasteners, other mechanical devices and/or the like. In other arrangements, the tip 160 is permanently or semi-permanently attached to the handpiece assembly 100.

In the embodiment illustrated in FIGS. 8A-8F, the tip 560 comprises one or more surfaces along its distal end 561 that are configured to treat (e.g., exfoliate) skin. Any of the embodiments of a tip disclosed herein, including but not limited to those illustrated in FIGS. 1-21B, tip designs incorporated by reference or any other tip designs, or variations thereof, can include one or more abrasive elements configured to treat skin. In addition, such tips can include one or more treatment elements, either in addition to or in lieu of abrasive elements. As used herein, "abrasive element" is a broad term and includes, without limitation, protruding elements, abrasive materials (e.g., grit, sandpaper-like material, other coarse materials, etc.), roughened surfaces, contoured surfaces, surfaces with openings, recesses or other features, brushes, blades, surfaces impregnated with diamonds or other materials and/or the like. Further, as used herein, "treatment element" is a broad term and includes, without limitation, an abrasive element, massage elements or features, elements or features configured to moisturize or apply one or more treatment agents or fluids, polishing or soothing elements or features and/or the like.

Figure 8A:
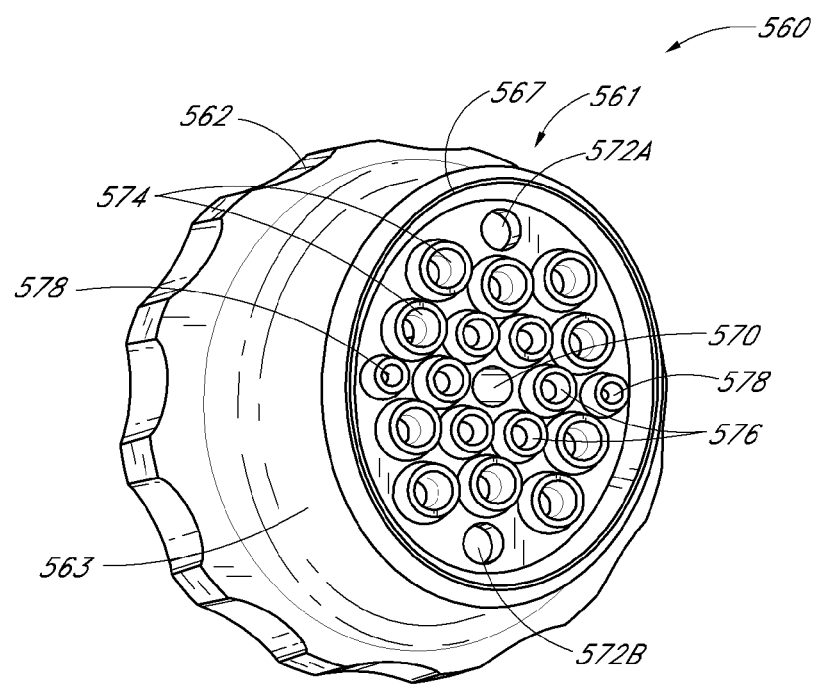
FIG. 8A illustrates a top perspective view of one embodiment of a removable tip configured to be placed along the distal end of a handpiece device.
Figure 8B:
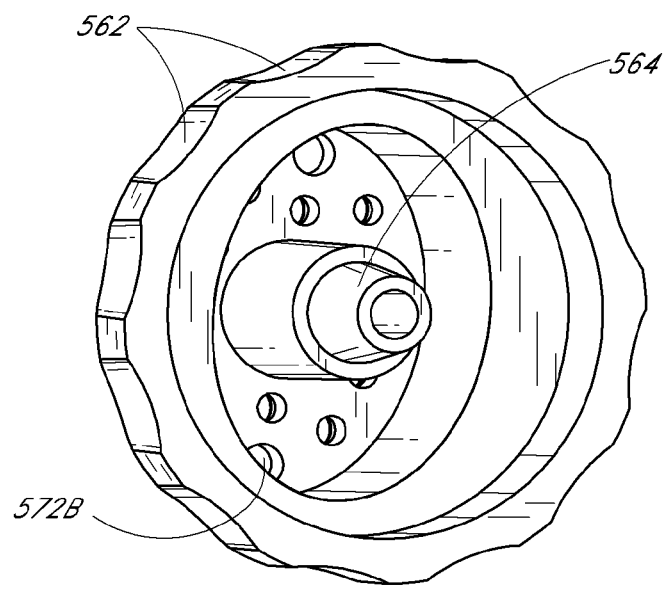
FIG. 8B illustrates a bottom perspective view of the removable tip of FIG. 8A.
Figure 8C:
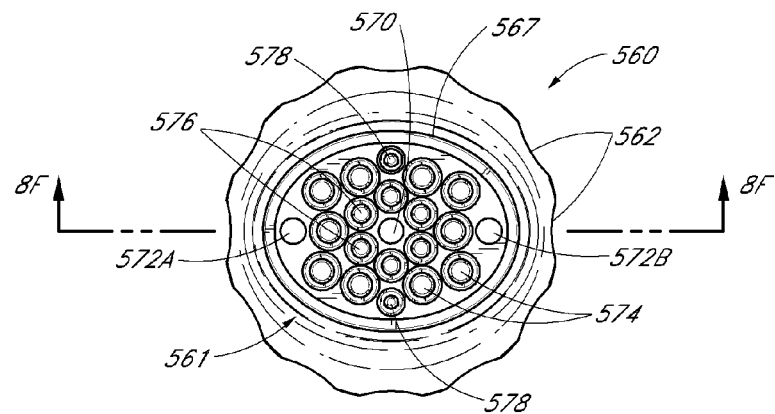
FIG. 8C illustrates a top view of the removable tip of FIG. 8A.
Figure 8D:
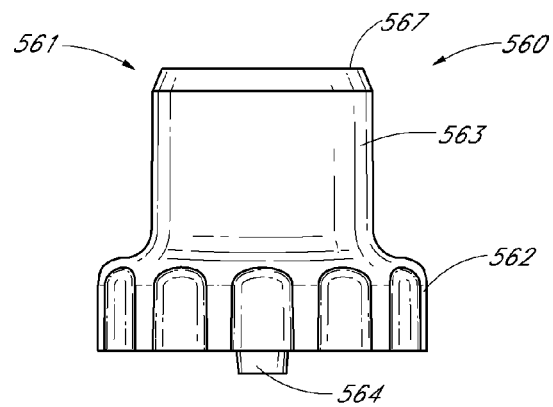
FIG. 8D illustrates a side view of the removable tip of FIG. 8A.
Figure 8E:
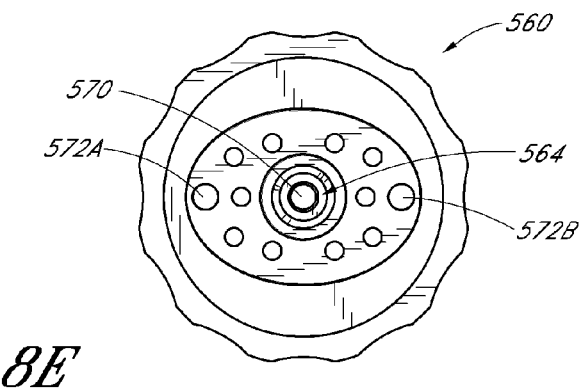
FIG. 8E illustrates a bottom view of the removable tip of FIG. 8A.
Figure 8F:
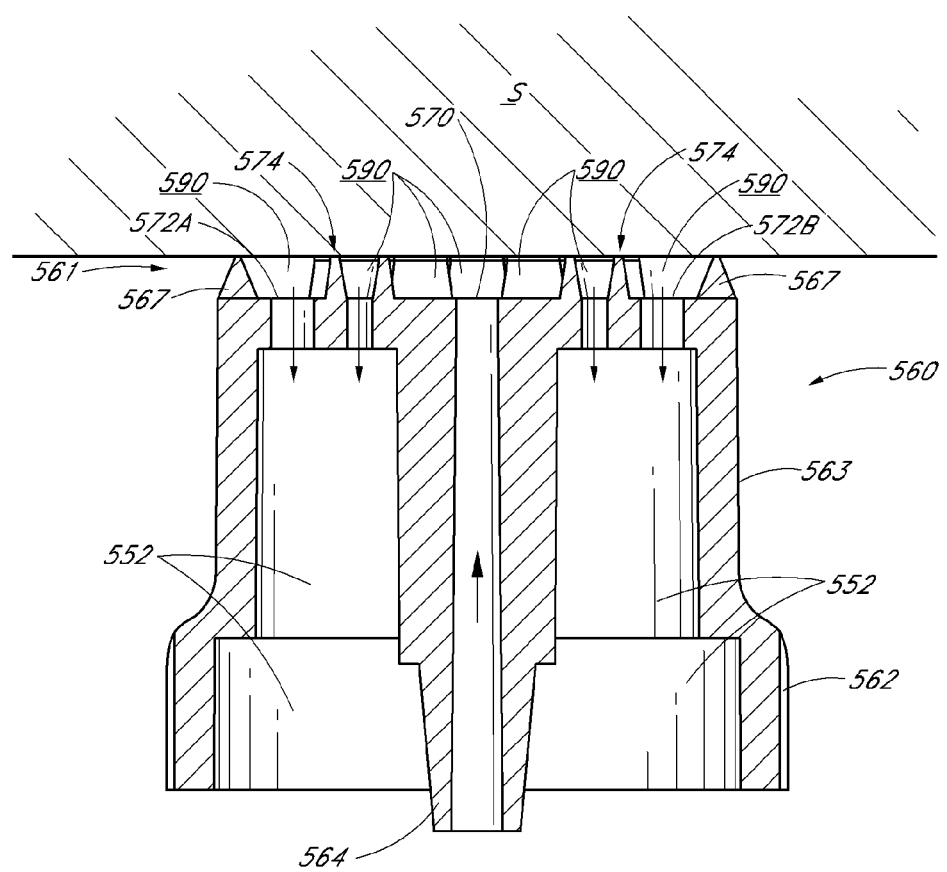
FIG. 8F illustrates a cross-sectional view of the removable tip of FIG. 8A.

As illustrated in FIGS. 8A, 8C and 8D, the tip can include a lip 567 or other ridge member along or near its outer periphery. The lip member 567 can generally define the periphery of the distal end 561 of the tip 560. In some embodiments, when the tip 560 is positioned against the skin S, as depicted in FIG. 8F, the lip member 567 completely, substantially or partially inhibits fluids or other materials from escaping a space 590 (or a plurality of spaces 590) generally defined between the tip 560 and the adjacent skin surface S.

With continued reference to FIGS. 8A-8F, the tip 560 can include a plurality of protruding members 574, 576, 578 positioned along its distal end 561 and within the interior of the lip member 567. The protruding members 574, 576, 578 can be posts or other cylindrically-shaped objects. In some embodiments, the protruding members 574, 576, 578 comprise relatively sharp edges, which can be configured to remove skin. The protruding members 574, 576, 578 can have relatively sharp planing blades. The plurality of protruding members 574, 576, 578 can ablate or roughen areas of the skin being treated.

As illustrated in FIGS. 8A-8F, the outer diameter or other comparable dimension (e.g., length, width, etc.) of the posts 574, 576, 578 or other protruding members can vary. For example, in the depicted embodiment, the tip 560 includes a number of large-sized posts 574, a number of medium-sized posts 576 and a number of small-sized posts 578. In other arrangements, the diameter and/or other dimensions of the protruding members can be similar or substantiality similar. The posts or other protruding members 574, 576, 578 can be located, spaced and otherwise oriented along the distal end 561 of the tip 560 in any desired or required manner.

Moreover, the location, spacing, orientation, layout and/or other characteristics of the posts 574, 576, 578 or other protruding members can be different than illustrated or discussed herein, as desired or required by a particular procedure or application. As discussed, the lip member 567 of the tip 560 can help create an enclosed space 590 (or a plurality of spaces 590) generally defined between the distal end 561 of the tip 560 and the skin surface being treated. Therefore, according to some embodiments, the lip member 567 extends above the top of the protruding members 574, 576, 578 so that the protruding members are within the enclosed space during a treatment procedure. In other embodiments, however, the top surface of the lip 567 is below or generally aligned with the top surface of the protruding members 574, 576, 578.

With continued reference to FIGS. 8A-8E, the tip 560 can include an interior delivery stem 564 that is configured to place the distal end 561 of the tip 560 in fluid communication with the one or more delivery channels or other conduits located within the handpiece assembly. For example, as discussed herein with reference to FIGS. 4, 5A and 5B, the delivery stem 164, 564 of the tip 160, 560 can be sized, shaped and otherwise adapted to receive serums, fluids and/or other materials from a delivery channel 140 of the adjustable distal portion 130 when the tip 160, 560 is properly secured within or to the handpiece assembly 100.

As illustrated in FIGS. 8A and 8C, the distal end 561 of the tip 560 can include an opening 570 through which fluids and/or other materials conveyed by the delivery stem 564 may exit. As shown, the opening 570 is located at or near the center of the distal end 561 of the tip 560. In other arrangements, a tip 560 can include additional stems 564 and/or openings 570. In addition, the size, shape, location and/or other details of the openings 570 can be different than illustrated herein.

Moreover, the distal end 561 of the tip 560 can include one or more outlet openings 572A, 572B through which exfoliated skin, spent serums, other waste liquids, fluids and other materials and/or the like can be removed. In the embodiment illustrated in FIGS. 8A-8F, the tip 560 includes two outlet openings 572A, 572B. However, more or fewer openings can be included, as desired or required. In addition, as shown in the cross-sectional view of FIG. 8F, some or all of the posts or other protruding members 574, 576, 578 can be generally hollow so that they perform a similar function as other outlet openings 572A, 572B of the tip 560. In other embodiments, however, some or all of the protruding members are not hollow or do not include openings therethrough. Regardless of the quantity, shape, size, orientation, spacing, layout and/or other characteristics of the outlet openings 572A, 572B and/or the hollow protruding members 574, 576, 576 included along the distal end 561 of the tip 560, exfoliated skin, spent serums, other fluids and/or any other materials can be removed from the enclosed space 590 to one or more collection areas 552 positioned within an interior portion of the tip 560.

In some embodiments, the outlet openings 572A, 572B and/or the protruding members 574, 576, 578 are in fluid communication with outlet stems (not shown) that extend toward one or more collection areas 552 within an interior portion of the tip 560. Once within an interior cavity or other portion of the tip 560, such waste materials can be drawn into one or more removal or waste channels 120, 150 positioned within the handpiece assembly 100 (FIG. 3B). An adequate vacuum or other suction source can transport such waste fluids and/or materials to a canister, other container and/or any other desired location via tubing 190 or another fluid conduit.

As discussed herein with reference to the schematic of FIG. 4F, in some embodiments, when the distal end 561 of a tip 560 is positioned against the skin being treated, one or more enclosed spaces are created between the skin surface and tip, generally along the interior of a peripheral lip member or other ridge. Therefore, as a vacuum or another suction force is applied to the removal or waste channels of a handpiece assembly, exfoliated skin, spent serum, other fluids and/or other materials can be removed from the enclosed spaces. In FIG. 8F, the enclosed space 590 is at least partially defined between the lip 567 of the tip 560 and the adjacent skin surface S being treated. At the same time, the delivery stem 564 of the tip 560, the delivery channel 140 of the handpiece assembly 100 (FIG. 4) and any other conduit or space that is in fluid communication with the enclosed space 590 of the tip 560 can also be subjected to a vacuum or other suction force. Consequently, serums, other treatment materials and/or the like can be advantageously transported to the distal end 561 of the tip 560 through one or more openings 570. As discussed, tip designs discussed or illustrated herein, or variations thereof, can comprise any combination of treatment elements and/or abrasive elements, as desired or required by a particular application.

For any of the tip embodiments disclosed herein, including those discussed with reference to FIGS. 1-21B, or variations thereof, the tips can comprise one or more rigid, semi-rigid and/or flexible materials, including without limitation, plastic or other polymers, metal (e.g., stainless steel), alloys, rubber, other synthetic or natural materials, combination thereof and/or the like.

Another embodiment of a removable tip 660 is illustrated in FIGS. 9A-9F. As shown, the tip 660 can include a generally oval or oblong shape. However, the tip 660 can have a different overall shape, such as, for example, circular, rectangular, other polygonal and/or the like, as desired or required. In some arrangements, the tip 660 comprises a lip 667, ridge or other feature along its outer periphery. As discussed herein with respect to the tip illustrated in FIGS. 8A-8F, such a lip 667 can help create one or more spaces along the distal end 661 of the tip generally defined by the tip 660 and the skin surface being treated.

Figure 9A:
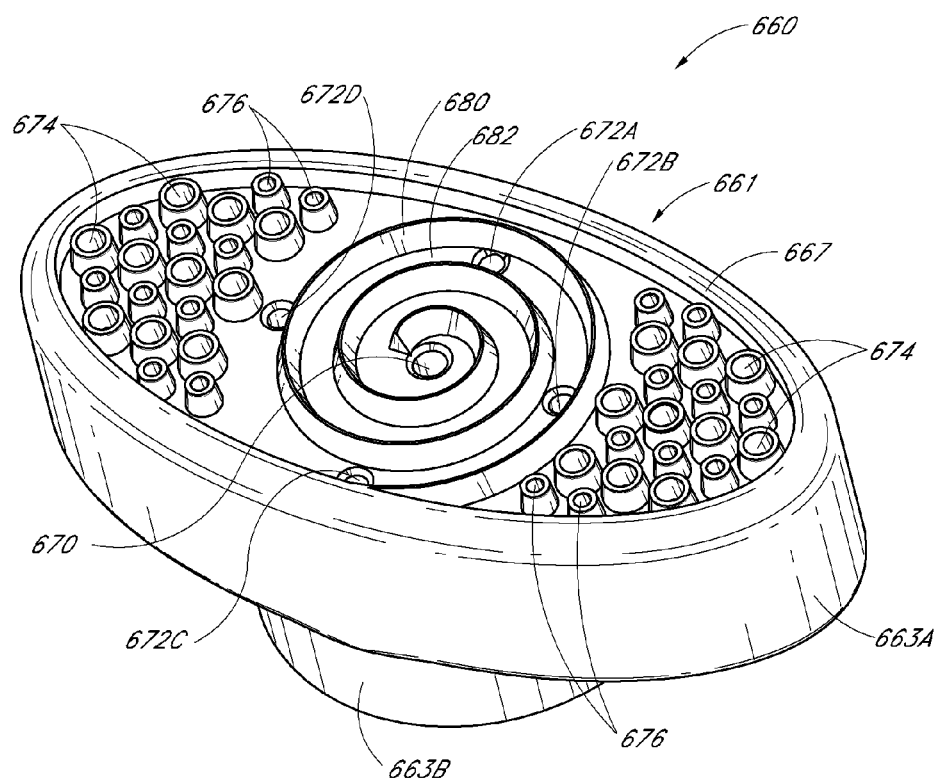
FIG. 9A illustrates a top perspective view of another embodiment of a removable tip configured to be placed along the distal end of a handpiece device.
Figure 9B:
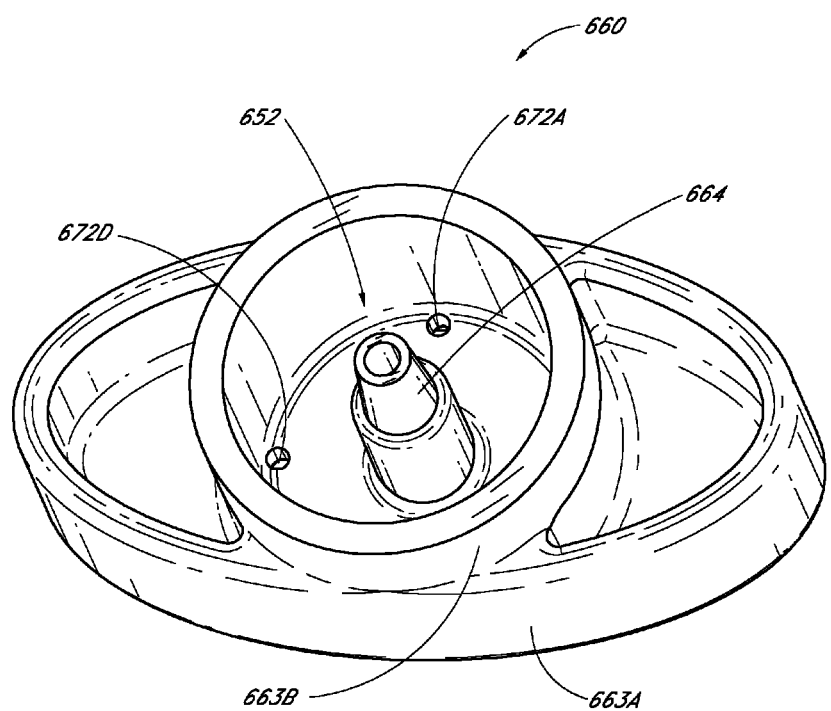
FIG. 9B illustrates a bottom perspective view of the removable tip of FIG. 9A.
Figure 9C:
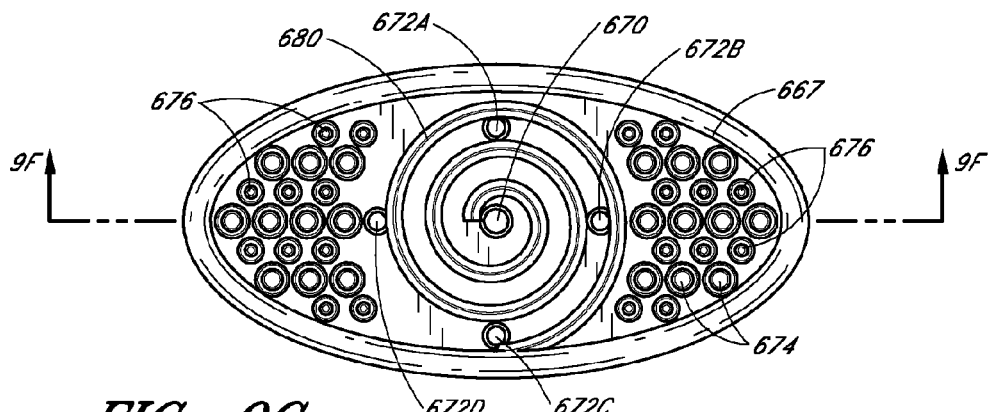
FIG. 9C illustrates a top view of the removable tip of FIG. 9A.
Figure 9D:
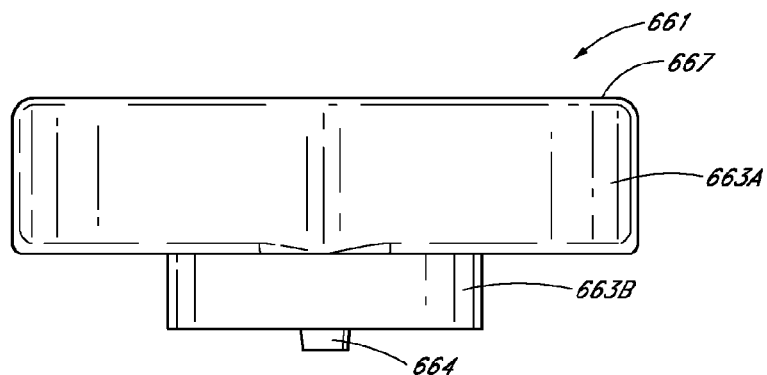
FIG. 9D illustrates a side view of the removable tip of FIG. 9A.
Figure 9E:
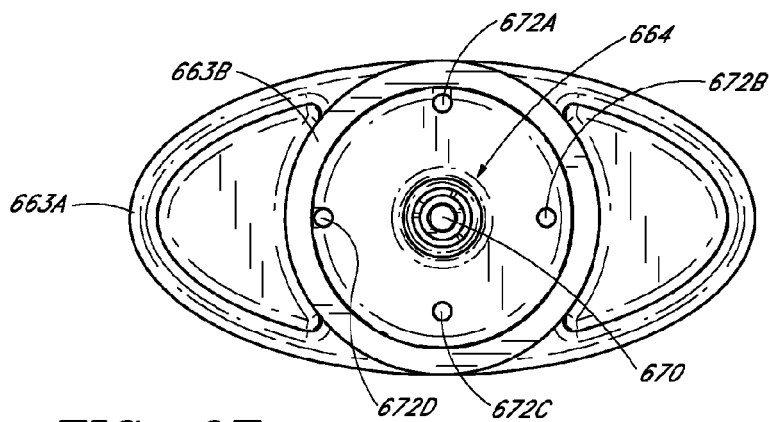
FIG. 9E illustrates a bottom view of the removable tip of FIG. 9A.
Figure 9F:
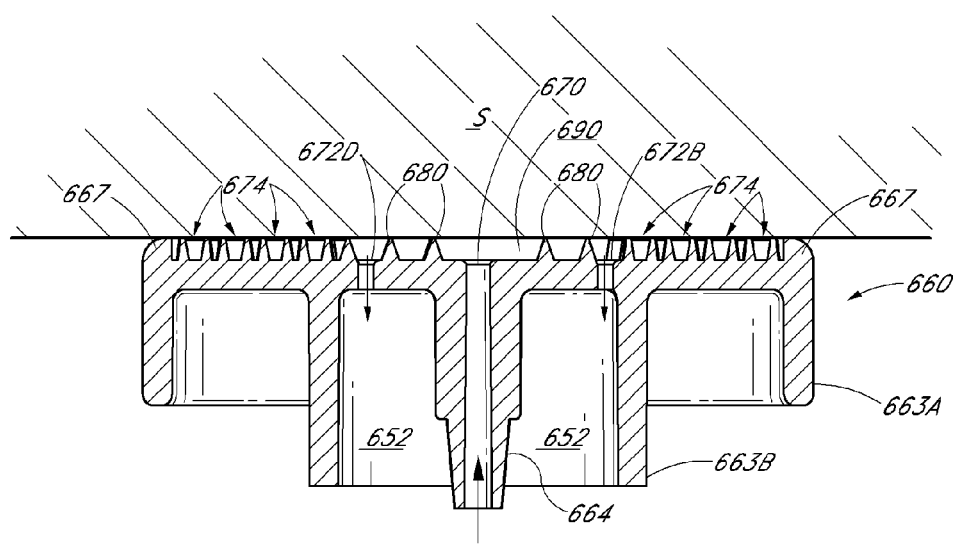
FIG. 9F illustrates a cross-sectional view of the removable tip of FIG. 9A.

With further reference to FIGS. 9A, 9C and 9F, the distal end 661 of the tip 660 can include a spiral-shaped channel 682 generally formed by a ridge 680 or other member. In the illustrated embodiment, the channel 682 extends generally continuously from a central opening 670 through which serums, other fluids and/or other materials conveyed to the tip 660 may exit. As shown, the tip 660 can include one or more outlet openings 672A-672D to permit exfoliated skin, spent serums and other fluids and/or any other waste materials to be removed from the distal end 661 of the tip 660. The outlet openings 672A-672D can be located within or near the channel 682 and/or anywhere else along the distal end 661.

With continued reference to FIGS. 9A and 9C, the tip 660 can include a plurality of protruding members 674, 676 that extend along its distal end 661. As discussed with reference to FIGS. 8A-8F, such protruding members 674, 676 can include relatively sharp edges that are configured to remove skin. In the illustrated arrangement, the protruding members 674, 676 include a generally cylindrical shape and are disposed along the outer portions of the tip 660. In addition, some of the protruding members 676 can have a different diameter (or other comparable dimension), length or other dimension than other protruding members 674. However, the quantity, diameter or other dimensions, size, shape, spacing, location, orientation, density, layout and/or other properties of the protruding members 674, 676 can vary as desired or required by a particular application or use.

In the depicted arrangement, since they are not in fluid communication with a vacuum or other suction force, some or all of the protruding members 674, 676 are not hollow and/or do not include openings therethrough. In other embodiments, however, one, some or all of the protruding members 674, 676 are configured to be in fluid communication with a collection area 652 of the tip 660. As illustrated in FIGS. 9B, 9D and 9F, the tip 660 can include an upper body portion 663A and a lower body portion 663B. In some embodiments, the delivery stem 564 through which serum, water, other liquids and/or other treatment materials are delivered to the distal end 661 and one or more collection areas 652 to which waste materials are directed can be housed within the lower body portion 663B. As discussed, the tip 660 depicted in FIGS. 9A-9F and discussed herein, or variations thereof, can comprise any combination of treatment elements and/or abrasive elements, as desired or required by a particular application.

FIGS. 10A-10F illustrate another embodiment of a removable tip 760 configured to be secured to a handpiece assembly. As with other arrangements disclosed herein, the tip 760 preferably includes one or more features that are adapted to remove skin during a treatment procedure. For example, in the illustrated embodiment, the tip 760 includes one or more pads 780A-780D or other members having a generally abrasive surface. The abrasive surface can include grit, a plurality of members (e.g., members similar to the protrusion members or posts described and illustrated herein) and/or the like. In some embodiments, the pads 780A-780D and/or other abrasive members are selectively removable from the tip 760. This permits users to advantageously change the abrasive portion of a tip 760 without replacing the entire tip 760. A pad 780A-780D or other abrasive member can be secured to the tip 760 using adhesives, snap connections, press-fit connections, hinged connections, tabs, screws, rivets, other fasteners and/or any other method or device. For example, if a pad is attached to a tip using an adhesive layer or substance, the pad can be removed by physically scraping or otherwise separating the pad and adhesives from the adjacent surfaces of the tip. Accordingly, a new pad or other abrasive member can then be glued or otherwise attached to the tip. In other embodiments, as illustrated in FIGS. 19A-20D and discussed in greater detail herein, the tip can be configured to receive a removable pad comprising one or more abrasive surfaces.

Tips comprising removable pads 780A-780D or other abrasive members can help enhance the flexibility of a skin treatment device or system. For instance, such pads can allow a user to make changes to the skin treatment properties of a tip without having to replace the entire tip or changing the tip design. For example, a user can selectively change the roughness and/or abrasiveness of the tip by replacing only the pads 780A-780D along the distal end 761.

Figure 10A:
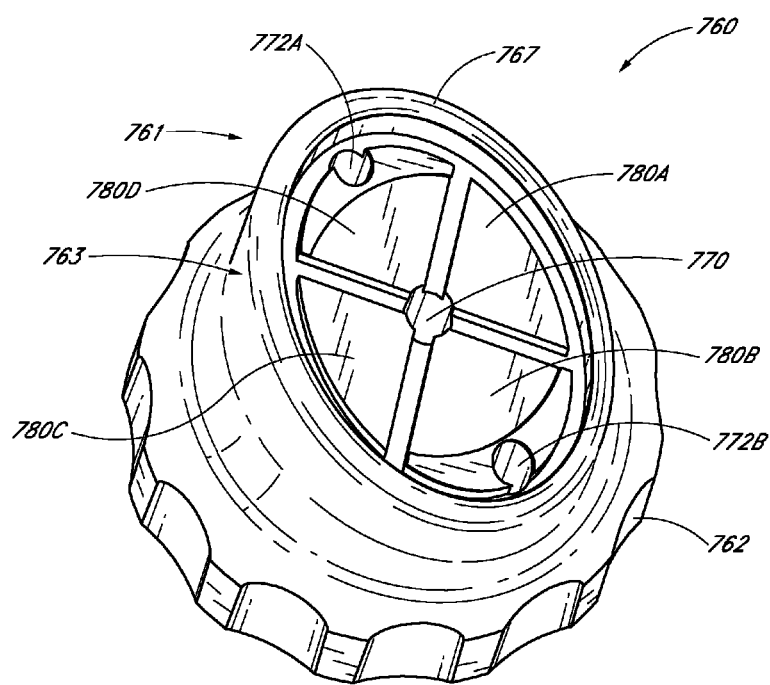
FIG. 10A illustrates a top perspective view of another embodiment of a removable tip configured to be placed along the distal end of a handpiece device.
Figure 10B:
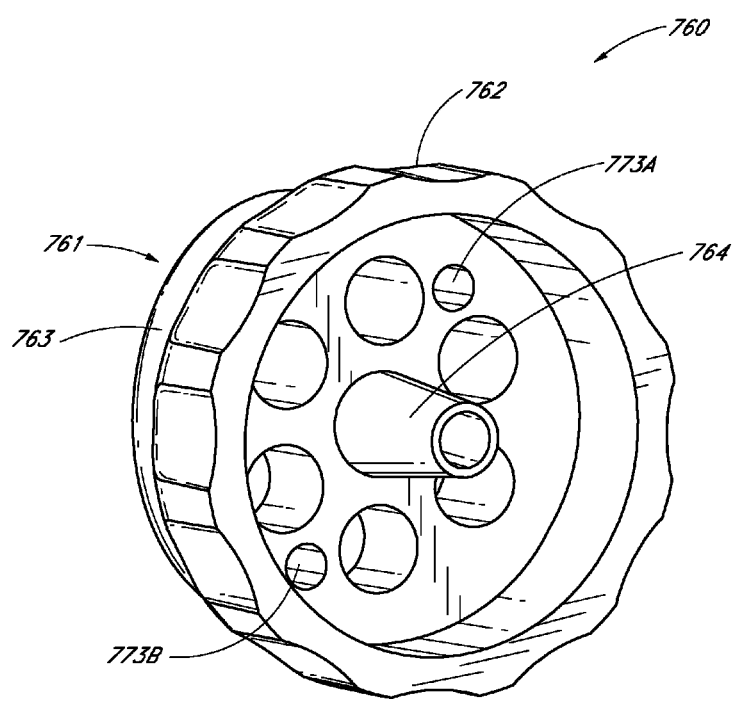
FIG. 10B illustrates a bottom perspective view of the removable tip of FIG. 10A.
Figure 10C:
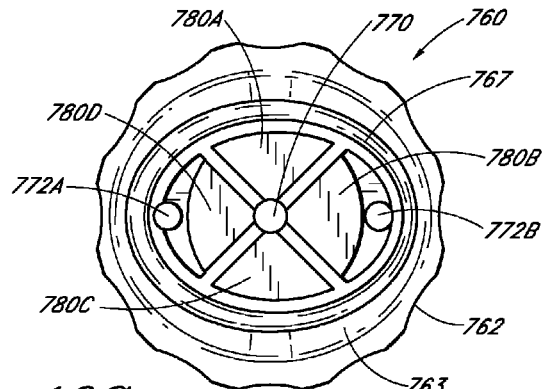
FIG. 10C illustrates a top view of the removable tip of FIG. 10A.
Figure 10D:
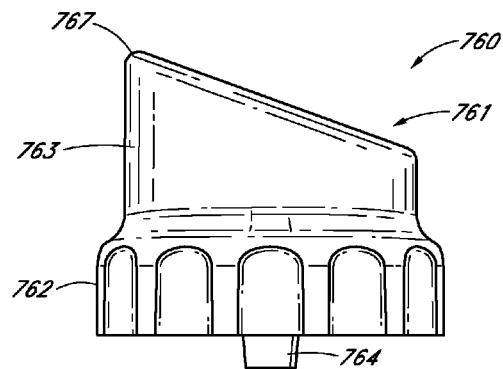
FIG. 10D illustrates a side view of the removable tip of FIG. 10A.
Figure 10E:
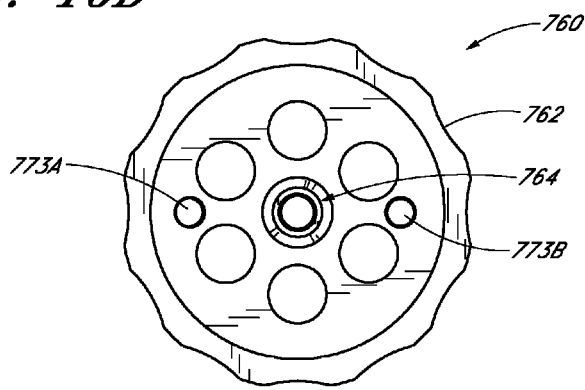
FIG. 10E illustrates a bottom view of the removable tip of FIG. 10A.

With continued reference to FIGS. 10A and 10C, the tip 760 can comprise a plurality of separate pads 780A-780D or other abrasive members. Alternatively, the tip 760 can include more or fewer (e.g., one, two, three, four, five, more than five, etc.) pads 780A-780D, as desired or required by a particular application or use. The pads 780A-780D or other members can be sized, shaped, oriented and/or otherwise configured to cover all, most or some of the distal end 761 of the tip 760.

As with other tip arrangements discussed and/or illustrated herein, the tip 760 depicted in FIGS. 10A-10F comprises an opening 770 along its distal end 761 that is in fluid communication with a delivery stem 764 or other conduit. Thus, serums, water, other fluids and/or any other materials can be delivered to the distal end 761 of the tip 760 through one or more such openings 770. In addition, the tip 760 can include one or more outlet openings 772A, 772B through which exfoliated skin, spent serums, other fluids and/or any other waste materials can be removed from the distal end 761. As illustrated in the cross-sectional view of FIG. 10F, such waste materials can be conveyed to one or more collection areas 752 within an interior portion of the tip 760 through corresponding waste channels 773A, 773B or other conduits. Alternatively, waste fluids and other materials can be directed to a collection area 752 without a dedicated waste channel of conduit 773A, 773B (see FIGS. 8A-8F and 9A-9F).

Figure 10F:
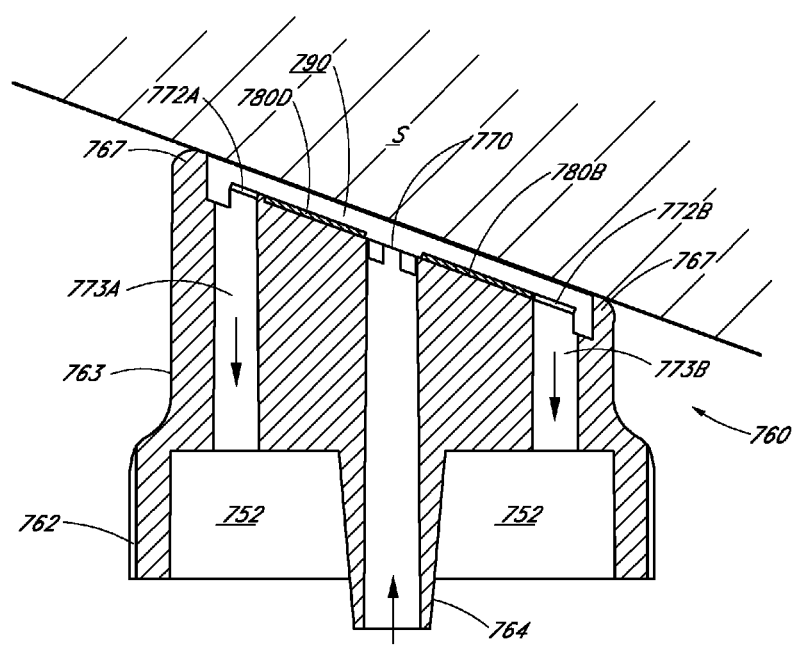
FIG. 10F illustrates a cross-sectional view of the removable tip of FIG. 10A.

With continued reference to FIG. 10F, the tip 760 can include an outer lip 767 or other peripheral member that is configured to create an enclosed space 790 when the tip 760 is generally positioned against skin. As discussed, the application of an adequate vacuum or other suction force to such an enclosed space 790 can help remove spent fluids, exfoliated skin and other waste materials from the distal end 761 of the tip, while simultaneously drawing serums, salicylic acid, other anti-acne acids and materials, microcapsules, capsules, other time-release products and substances, and/or other treatment fluids or materials toward the tip (e.g., from a cartridge via a delivery stem 764).

As discussed, any of the tip embodiments disclosed herein, including but not limited to those illustrated in FIGS. 1-21B, can be configured so that the flow direction of serums, other fluids and/or other materials passing through the various conduits, channels, passages or other hydraulic components of such tips can be selectively reversed, as desired or required. For example, a tip, along with the handpiece assembly to which it is attached, can be configured so that fluids and/or other materials pass through one or more centrally-located passages, conduits or other portions thereof. Alternatively, the tip and handpiece assembly can be configured so that fluids and/or other materials pass through one or more non-centrally located (e.g., peripheral, offset, etc.) passages, conduits or other portions thereof.

Further, the connection and/or other hydraulic details of the tip and adjacent portions of the handpiece assembly can vary, as desired or required. For example, as discussed with reference to the embodiment of FIGS. 5A-5C, the adjustable distal portion of the handpiece assembly can include a nozzle or other protruding member that is configured to be secured within a recess or other corresponding portion of the tip to mechanically connect and place the two members in fluid communication with one another. However, in other arrangements, such as, for example, those illustrated in FIGS. 3A-4B, a nozzle or other protruding portion of the tip is adapted to be secured within a corresponding area of the adjustable distal portion of the handpiece assembly. Thus, the size, shape, general design, other connection and/or hydraulic details and/or other characteristics of any of the embodiments of a tip, handpiece assembly and/or other components of a skin treatment system disclosed herein, or variations thereof, can be modified, as desired or required.

Although only certain embodiments of tips are illustrated and discussed herein, any other tip configurations or designs can be used on a handpiece assembly to perform a skin treatment procedure. As discussed, in some embodiments, the tips are removable, allowing a user to selectively interchange tips either during a procedure or between procedures, as desired or required by a particular application. In other arrangements, tips are more permanently or semi-permanently attached to the handpiece assembly. Additional embodiments of tips are disclosed in U.S. patent application Ser. No. 11/392,348, filed on Mar. 29, 2006 and published on Jul. 5, 2007 as U.S. Publication No. 2007/0156124, and U.S. patent application Ser. No. 09/699,220, filed on Oct. 27, 2000 and issued on Oct. 7, 2003 as U.S. Pat. No. 6,629,983, the entireties of both of which are hereby incorporated by reference herein.

In any of the embodiments disclosed herein, or variations thereof, the tip, the handpiece assembly and/or any other component or device can include rigid and/or semi-rigid materials. For example, a tip can comprise plastic, another polymeric material, rubber, metal and/or the like. Accordingly, the tips and/or other portions of the handpiece assembly can be manufactured using any suitable method, such as, for example, injection or compression molding, thermoforming, other molding methods, casting and/or the like. The tips can be disposable so that they are used once or only for a limited number of times. Alternatively, if properly treated, the tips can be reused. Therefore, in such embodiments, the tips are preferably configured to withstand the required cleaning, sterilizing, disinfecting and/or other treatment procedures to which they may be exposed.

Any of the tips disclosed herein can be used in wet and/or dry systems. In general, wet systems include skin treatment devices, assemblies or systems in which serums, salicylic acid, other anti-acne acids and materials, microcapsules, capsules, other time-release products and substances, water, other fluids and/or other materials are conveyed, either continuously or intermittently, to the tip during a procedure. As discussed in greater detail herein, such fluids and/or other materials can be delivered through the handpiece assembly, tip and/or other components of the skin treatment system in their final, usable form. In other arrangements, such materials and/or substances are positioned on the tip and/or other portions the system (e.g., as solids, gels, concentrated solutions, etc.) and are adapted to be dissolved, diluted, mixed or otherwise combined with water (e.g., distilled, tap water, sterile, filtered, etc.), saline, other dilutants or dissolvents and/or other fluids to prepare them for use. On the other hand, dry systems can include skin treatment devices, assemblies and systems in which fluids and/or other materials are generally not conveyed to the tip during the procedure.

As discussed, one or more fluids and/or other substances can be delivered to the tip of a handpiece assembly during a skin treatment procedure. In some embodiments, such fluids and/or other materials are stored within a cartridge (e.g., vial, ampoule, other container, etc.) that is secured to or within the handpiece assembly. Alternatively, these fluids and/or other materials can be stored in a canister or other container that is separate from the handpiece assembly. In such arrangements, as discussed herein with reference to FIGS. 6B and 7, the handpiece assembly can be placed in fluid communication with one or more containers using conduits or other fluid lines.

In some embodiments, human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance are selectively delivered to the skin during a treatment procedure. Such materials can be delivered individually or as part of a mixture. Such materials or combination of materials can be provided in a cartridge or other container, which, as discussed, can be placed in fluid communication with a handpiece assembly. These treatment fluids and other materials, either alone or in combination, can help reduce the appearance of wrinkles, fine lines, age spots, scarring and/or other skin conditions. In addition, such fluids and/or other materials can help to reduce skin roughness, thereby facilitating rejuvenation of the skin and/or improving skin texture. Further, such fluids or other treatment materials can provide one or more other therapeutic, comfort, anesthetic, aesthetic or other benefits to a user or his or her skin.

In any of the embodiments described and/or illustrated herein, or variations thereof, treatment fluids and/or other materials can be delivered to the tip of a handpiece assembly using one or more devices or methods. For example, in some embodiments, such substances are selectively delivered through a cartridge, supply canister, fluid bottle, combinations thereof and/or the like. Such serums, compositions, other fluids and/or other materials or substances can be pre-mixed so that they are delivered to the tip and the skin unmodified or substantially unmodified.

As discussed in greater detail herein, in some embodiments, human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance are provided to users as a pack or in other forms. For example, such materials and other substances can be provided as a solid (e.g., tablet, capsule, etc.), dry granular materials, viscous gels, concentrated fluids or other solutions and/or the like. Such packs or other solids, semi-solid, gelatinous and/or other substances can be configured to be combined or mixed with water, saline and/or some other fluid by a user to achieve a desired end product or concentration.

In other embodiments, one or more treatment materials can be impregnated, embedded, deposited or otherwise positioned within and/or on the tips and any other portion of a handpiece assembly. Thus, such materials (e.g., powders, tablets, capsules, other solids, granular materials, gels, etc.) can advantageously dissolve, melt, break down or otherwise transform when they are contacted by water, saline, other dilutants, dissolvents and/or other liquids or fluids delivered to the tip (e.g., through the handpiece assembly, by an external fluid source, etc.) In other arrangements, the treatment materials are contained within a capsule, tablet or other enclosure. Such enclosures can be configured to dissolve when placed in water or some other fluid. Therefore, a user may be required to place a capsule, the contents of a pack or some other materials into a cartridge, canister or other container and add or otherwise supply water, saline, other fluids and/or other dissolvent before use.

Figure 11:
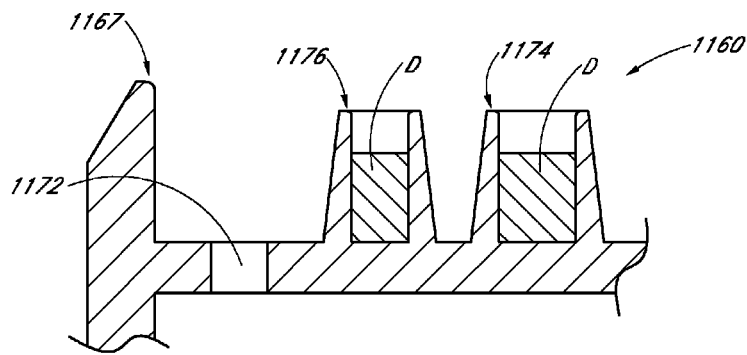
FIG. 11 illustrates a cross-sectional view of a tip comprising posts that have been partially filled with solids, gels and/or other materials configured to be mixed or combined with water, other dilutants or other fluids, according to one embodiment.

FIG. 11 illustrates a partial cross-sectional view of a tip 1160 configured to be secured to the distal end of a handpiece assembly. As shown, the tip 1160 can include one or more fluid inlet openings 1172 through which water, saline, other dilutants or dissolvents, other fluids and/or other materials can be selectively delivered to the tip, in accordance with the various embodiments disclosed herein. Further, the tip 1160 can include one or more outlet openings (not shown) through which exfoliated skin, spent serums or other fluids, debris and/or other waste materials can be removed away from the skin surface being treated.

With continued reference to FIG. 11, the tip 1160 can additionally comprise a plurality of protruding members 1174, 1176 positioned along its distal end and within the interior of the tip's outer lip member 1167. As discussed, such protruding members 1174, 1176 can be posts or other cylindrically-shaped objects. In some embodiments, the protruding members 1174, 1176 comprise relatively sharp edges that are configured to remove skin when the tip is moved relative to a skin surface. The protruding members 1174, 1176 can have relatively sharp planing blades. The plurality of protruding members 1174, 1176 can ablate or roughen areas of the skin being treated.

According to some embodiments, some or all of the posts 1174, 1776 or other protruding members comprise one or more materials or other substances D. For example, the posts can be at least partially filled with dried or granular materials, tablets, capsules, powders, gels, concentrated liquids and/or other substances that are configured to dissolve, melt, soften, dilute, disperse, mix or otherwise be removed from an interior of the protruding members 1174, 1176. Such materials or other substances, which can be provided in one or more different forms or phases (e.g., liquid, solid, gel, etc.), can include, without limitation, human growth factors, cytokines, collagen, antioxidants, matrix proteins, serums, salicylic acid, other anti-acne acids and materials, microcapsules, capsules, other time-release products and substances, vitamins, chemical exfoliation agents, lotions, soothing agents, brightening or lightening agents (e.g., kojic acid), peptides, peeling agents, acids, anesthetics, medicants, other non-active or active compounds, other fluids or materials, combination or mixtures thereof and/or the like.

With continued reference to FIG. 11, as water (e.g., distilled, tap water, filtered, etc.), saline, other dilutants or dissolvents, other fluids and/or the like are selectively delivered through the handpiece assembly and through one or more openings 1172 of the tip 1160, the various materials and/or other substances D situated within the posts 1174, 1176 can be dissolved, diluted and/or otherwise mixed to form a desired solution or mixture. Thus, a tip 1160 can be customized for a particular skin treatment procedure by including one or more desired or required substances within the protruding members and/or other cavities of the tip 1160. Accordingly, the various solutions conveyed, dissolved and/or otherwise generated at or near the tip 1160 can used to achieve a desired result, such as, for example, providing vitamins, growth factors, soothing agents or lotions, healing agents and/or other substances to treated skin, moisturizing the skin, enhancing the comfort of the person being treated and/or the like. Further, such materials impregnated or otherwise disposed on the tip can be customized to target a particular treatment procedure or phase, skin type, skin ailment or condition and/or the like.

Providing the desired materials and/or other substances on the tip can help simplify a microdermabrasion or other skin treatment procedure. For instance, in such embodiments, the user may only need to provide water, saline and/or some other basic fluid to perform the procedure. Thus, the need to deliver separate serums, salicylic acid, other anti-acne acids and materials, microcapsules, capsules, other time-release products and substances, other fluids and/or materials through the handpiece assembly (e.g., using a manifold system, a cartridge, etc.) can be advantageously eliminated or simplified. As a result, the likelihood of a user making mistakes can be reduced or eliminated. In addition, by delivering only water, saline and/or other relatively clean fluids through the various delivery conduits, passages, ports, openings and other hydraulic components of the tip, handpiece assembly and other components of a skin treatment system, the need to periodically clean the various devices and other equipment can be advantageously reduced or eliminated. Thus, the effective life of the skin treatment system can be extended. Relatedly, the likelihood of potentially dangerous or undesirable cross-contamination between the various serums, agents, other fluids and/or other materials can also be reduced or eliminated.

Figure 12A:
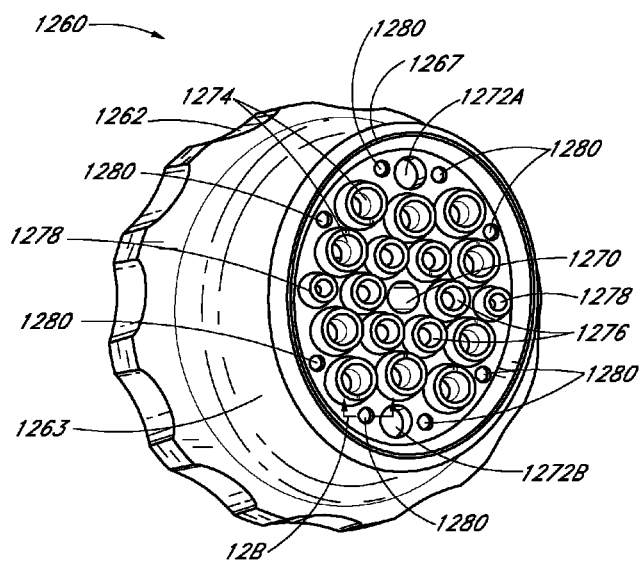
FIG. 12A illustrates a front perspective view of one embodiment of a tip comprising a plurality of recesses that can be selectively filled solids, gels and/or other materials.

FIG. 12A illustrates one embodiment of a tip 1260 comprising a plurality of recesses 1280 or other openings located along its distal surface. As shown, such recesses 1280 or other openings can be positioned along an outer periphery of the tip's distal surface. However, in alternative embodiments, one or more recesses 1280 are located between the posts 1274, 1276, 1278 and/or at any other location, either in lieu of or in addition to the recesses 1280 being positioned along an outer periphery of the tip. Such recesses or other openings can be configured to include one or more solids, gels, concentrated solution, dissolvable materials and/or other substances D therein.

Figure 12B:
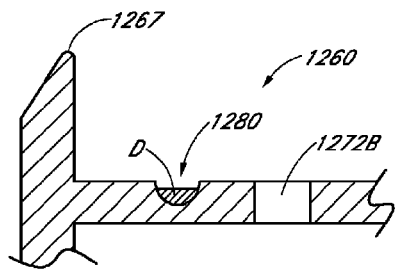
FIG. 12B illustrates a cross-sectional view of the tip of FIG. 12A.

With reference to the cross-sectional view of FIG. 12B, the recesses can include a semi-circular, curvate or other rounded shape. In certain embodiments, the recesses 1280 are at least partially filled with dried or granular materials D, tablets, capsules, powders, gels, concentrated liquids and/or other substances that are configured to at least partially dissolve, melt, soften, dilute, disperse, mix or otherwise be removed from an interior of the recesses or other openings. As discussed herein with reference to other embodiments, such materials or other substances, which can be provided in one or more different forms or phases (e.g., liquid, solid, gel, etc.), can include, without limitation, human growth factors, cytokines, collagen, antioxidants, matrix proteins, serums, salicylic acid, other anti-acne acids and materials, microcapsules, capsules, other time-release products and substances, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or the like.

The quantity, size, depth, shape, capacity, location, spacing and/or other details of the recesses or other openings positioned along one or more tip surfaces can vary, as desired or required. For example, in the tip arrangement of FIG. 12C, the illustrated recess 1280' includes a generally rectangular cross-sectional shape. However, a recess or other opening can include any other cross-sectional shape, such as, for example, triangular, other polygonal, irregular and/or the like.

Figure 13A:
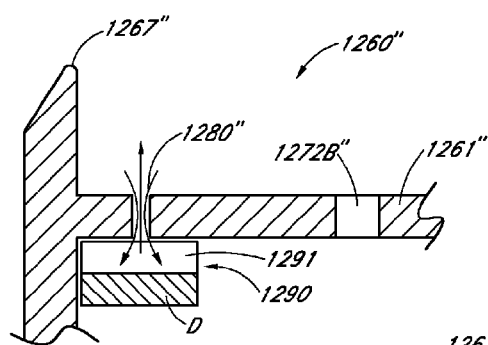
FIG. 13A illustrates a cross-sectional view of a tip having a cartridge or other container comprising solids, gels and/or other materials secured thereto, according to one embodiment.
Figure 13B:
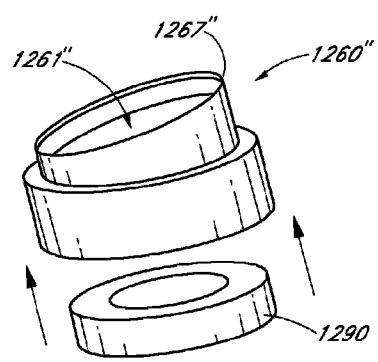
FIG. 13B illustrates an exploded perspective view of the tip and cartridge of FIG. 13A.

In alternative embodiments, the desired solids D, other dry or semi-dry materials, gels, concentrated materials and/or other substances are included within a cartridge or other container. As illustrated in FIGS. 13A and 13B, such a cartridge 1290 or other container can be secured to one or more portions of the tip 1260". In the depicted arrangement, the cartridge 1290 is situated below the top surface 1261" of the tip 1260" and aligned with one or more openings 1280" of the top surface 1261". Accordingly, the solids, gels, fluids and/or other materials or substances stored within an interior of the cartridge 1290 can be configured to exit the cartridge 1290 through one or more openings 1280" of the tip's top surface 1261". In some embodiments, the cartridge or other container 1290 includes one or more slots, perforations, orifices or other openings through which the various materials D can exit. Alternatively, the cartridge 1290 can include one or more porous surfaces that allow the internal contents D to freely exit the cartridge 1290. Thus, the cartridge 1290 can include an outer cage, a perforated or other porous surface and/or the like.

With continued reference to FIG. 13A, water (e.g., distilled, tap water, filtered, etc.), saline, other dilutants or dissolvents and/or other fluids that are delivered to the tip 1260" (e.g., through one or more openings 1272" along the top surface 1261" of the tip 1260") can be configured to enter into an interior 1291 of the cartridge 1290 through one or more openings 1280". Accordingly, the materials and/or other substances D contained within the cartridge 1290 can be at least partially dissolved, melted, diluted, reacted and/or otherwise mixed or combined with the water, saline or other fluids. This can facilitate the controlled removal of these materials D toward the distal working surface of the tip 1260".

As illustrated in FIG. 13B, the cartridge 1290 can have a generally toroidal or donut-shape. In some embodiments, the cartridge 1290 or other container is configured to be positioned within an interior portion of the tip 1260". The cartridge 1290 can be secured to the tip 1260" using a friction fit connection, one or more mechanical features or devices (e.g., threads, clips, screws, tabs, etc.) and/or any other attachment device or method. In addition, the shape, size, orientation relative to the tip 1260" and/or any other characteristics of the cartridge 1290 can be different than illustrated in FIGS. 13A and 13B. For instance, the cartridge 1290 or other container can have a generally rectangular, circular or any other shape. Further, the cartridge 1290 can be configured so that it does not extend around the entire perimeter of the tip 1260". In other embodiments, a cartridge or other container comprising solids, gels and/or other materials is positioned along a different portion of the tip, such as, for example, at or near the center, locations between the center and the periphery and/or the like.

Figure 14A:
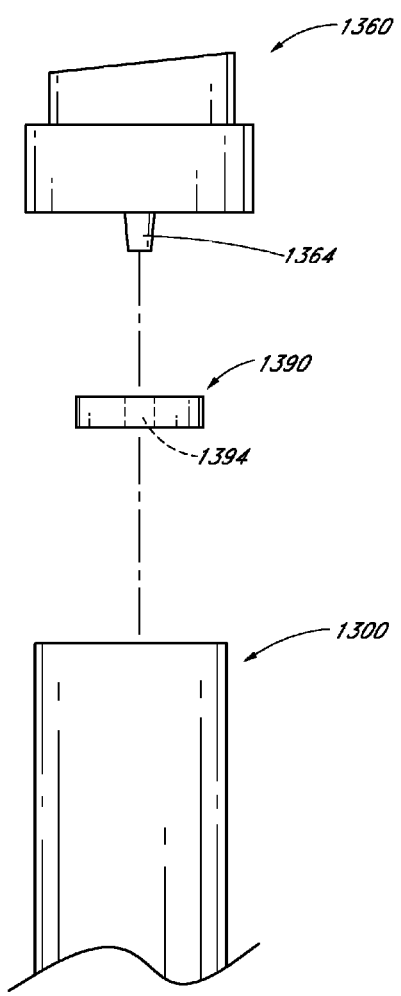
FIG. 14A schematically illustrates an exploded view of a handpiece assembly, a tip and a cartridge or other container according to one embodiment.

FIG. 14A schematically illustrates an embodiment of a disc 1390, capsule or other item comprising one or more solids, other dried or partially dried substances, gels, concentrated solutions and/or the like. These materials can comprise some, most or the entire portion of the disc 1390 or other item. Alternatively, the materials can be embedded, impregnated and/or otherwise situated on or within one or more portions or areas (e.g., surface) of the disc 1390 or other item. In other embodiments, such solids, gels and/or other materials are provided in a cartridge or other container that includes one or more openings through which the substances may exit (e.g., in their original form, after being at least partially dissolved, diluted or otherwise mixed with water or another fluid, etc.).

With continued reference to FIG. 14A, the disc 1390, capsule or other item can be sized, shaped and otherwise configured to be positioned between the tip 1360 and the main body portion 1300 of a handpiece assembly. According to some embodiments, the disc 1390 or other item includes an opening 1394 or other feature that is adapted to engage and secure to one or more regions of the tip 1360, the main body portion 1300 and/or any other area of a handpiece assembly. In certain arrangements, the disc 1390 is maintained in a desired orientation when the tip 1360 is properly connected to the main body portion 1300 of the handpiece assembly. However, a desired or required position of a disc 1390, capsule or any other items comprising one or more solids, gels, concentrated solutions or other fluids and/or other materials can be maintained using any other attachment method or device.

Figure 14B:
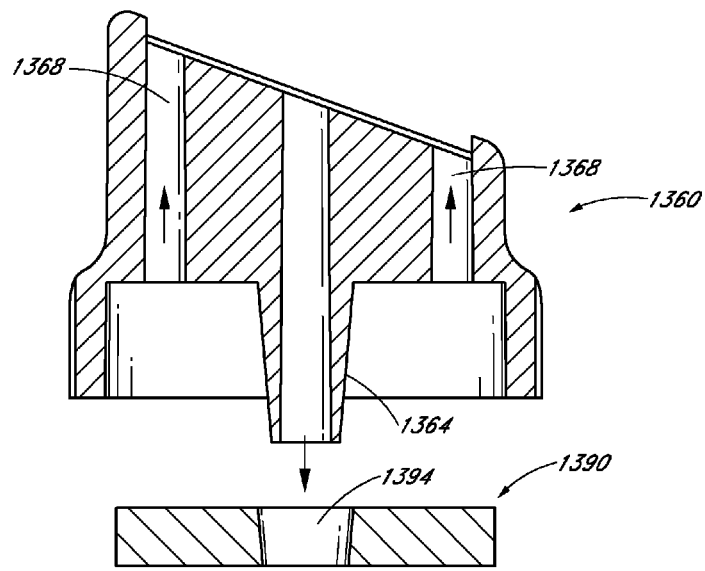
FIG. 14B illustrates an exploded cross-sectional view of one embodiment of a tip and a cartridge or other container comprising solids, gels and/or other materials.
Figure 14C:
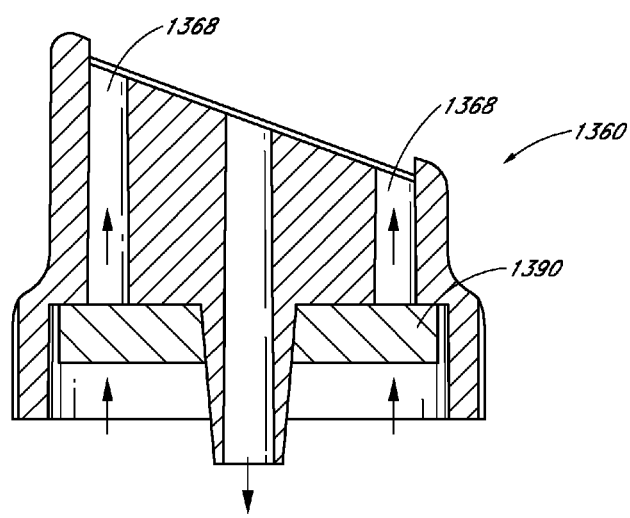
FIG. 14C illustrates a cross-sectional view of the cartridge and tip of FIG. 14B with the cartridge secured within an interior portion of the tip according to one embodiment.

FIGS. 14B and 14C illustrate one embodiment of a disc 1390, capsule or other item comprising one or more human growth factors, cytokines, soluble collagen, antioxidants, matrix proteins, serums, salicylic acid, other anti-acne acids and materials, microcapsules, capsules, other time-release products and substances, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or other substances. For example, as discussed, such materials can be provided on or within the disc 1390 (e.g., along an exterior surface, within an interior portion, etc.).

According to some embodiments, the disc 1390 includes a center opening 1394 to permit the disc 1390 to be positioned over a stem 1364 extending within an interior of the tip 1360. In the illustrated arrangement, the stem 1364 comprises an outlet conduit or channel that is configured to remove exfoliated skin, spent treatment materials and other debris away from the distal end of the tip 1360. However, as discussed herein with reference to the tip of FIGS. 15A and 15B, the stem 1364 can include one or more conduits or channels that are configured to deliver water, saline, other dissolvents, dissolvents, dissolving agents and/or other fluids toward the skin surface being treated.

With continued reference to FIGS. 14B and 14C, the disc 1390, capsule, cartridge or container or other item comprising the desired materials can be configured to be removably fixed to the stem 1364 of the tip 1360 using a press-fit or other friction connection. For example, in some embodiments, the disc 1390 can be positioned far enough into an interior of the tip 1360 so that the exterior surface of the tip's stem 1364 frictionally engages the inner surface of the disc's opening 1394. However, as discussed, one or more other attachment methods or devices can be used in addition to or in lieu of such a friction or press fit connection in order to secure the disc 1390 to the tip 1360.

Once the disc 1390, capsule or other member has been properly secured to the tip 1360, as depicted in FIG. 14C, the tip 1360 can be attached to the distal end of the handpiece assembly (e.g., adjustable distal portion). Thus, water (e.g., distilled, tap water, filtered, etc.), saline, other dilutants or dissolvents or other fluids being delivered to the tip 1360 can be configured to contact the various substances (e.g., tablets, capsules, other solids, granulated materials, gels, concentrated solutions or other materials, etc.) situated on or within the disc 1390. Such materials and other substances can be advantageously dissolved, diluted, melted, softened and/or otherwise conditioned so that they are delivered to the distal end of the tip 1360 through one or more conduits 1368 of the tip 1360. As a result, human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance can be advantageously delivered to the skin being treated, as desired or required.

According to some embodiments, water, saline or other fluids are configured to flow past the exterior surfaces of the disc 1390, capsule or other item. Thus, solids, gels, fluids and/or other materials impregnated on such surfaces, positioned within recesses or other openings in fluid communication with such surfaces and/or the like can be transferred to the skin surface being treated. In alternative embodiments, the solids, gels, fluids and/or other materials are positioned within an interior cavity of the disc 1390 or other item. For example, the disc 1390 or capsule can comprise a cage or other porous structure that is configured to house one or more dissolvable or dilutable solids or gels. Therefore, water, saline and/or other fluids can be adapted to travel through one or more openings of the disc 1390 or other member in order to contact the various materials contained therein. Accordingly, the disc 1390 can be configured to lose mass over time as water or other fluids dissolve, dilute or otherwise combine with the materials positioned on or within the disc 1390. In alternative embodiments, the disc 1390 (e.g., cage, container having one or more openings, etc.) or other item secured within the tip 1360 is adapted to maintain its shape over time if such a disc is used to merely contain the solids, gels, fluids and/or other materials that will be selectively transported toward the distal end of the tip 1360.

Such discs 1390, capsules, containers or other items can be used in conjunction with any of the tip designs illustrated or discussed herein, or variations thereof. Further, the size, shape, general configuration, location relative to the tip or other adjacent portions of the handpiece assembly and/or any other characteristics of the disc 1390 can vary, as desired or required. For instance, the disc 1390 can include a non-circular shape (e.g., rectangular, triangular, other polygonal, elliptical, etc.). Further, the disc 1390 can include a curved or fluted surface. In other arrangements, a disc 1390 does not extend completely around a stem 1464 or other central portion of the tip interior. Thus, the disc 1390 can be asymmetrically positioned relative to the stem 1464 or tip centerline. In another embodiment, the disc 1390 is positioned on only one side of the stem 1464.

Figure 15A:
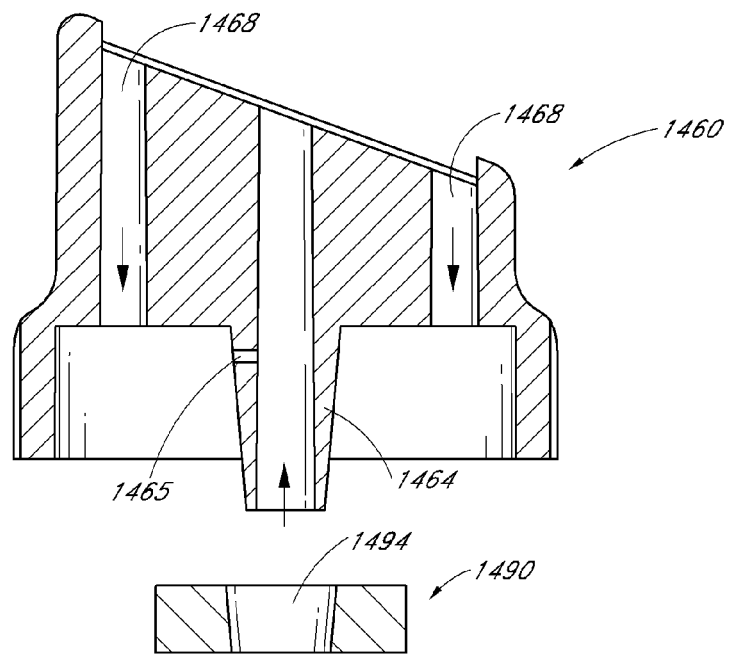
FIG. 15A illustrates an exploded cross-sectional view of another embodiment of a tip and a cartridge or other container comprising solids, gels and/or other materials.
Figure 15B:
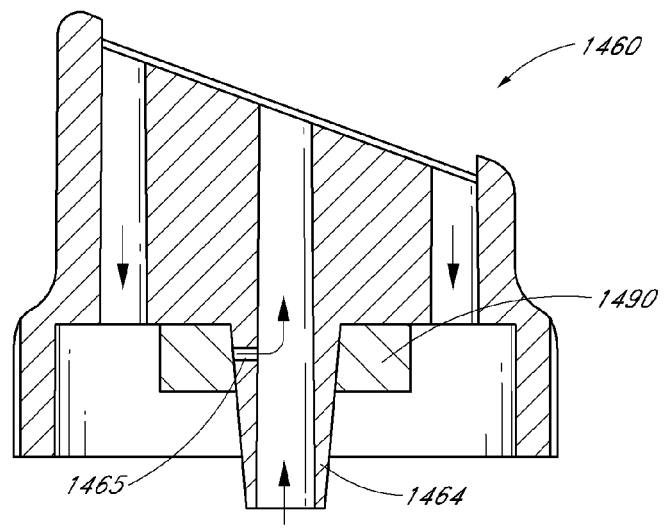
FIG. 15B illustrates a cross-sectional view of the cartridge and tip of FIG. 15A with the cartridge secured within an interior portion of the tip according to one embodiment.

Another embodiment of a disc 1490 that is configured to be secured to a tip 1460 of a handpiece assembly is illustrated in FIGS. 15A and 15B. As shown, the flow through the stem 1464 and the various conduits 1468 of the tip 1460 is generally reversed from the configuration of FIGS. 14A-14C. However, similar to the arrangement of FIGS. 14A-14C, the depicted disc 1490, capsule or other item is configured to secure to an exterior portion of the stem 1464.

With continued reference to FIGS. 15A and 15B, the solids, gels, concentrated fluids and/or other materials contained within an interior of the disc 1490 can be configured to come into contact with water, saline, other dilutants or dissolvents and/or other fluids being conveyed through the internal passage of the stem 1464. Accordingly, such materials can be dissolved, diluted, softened, mixed and/or otherwise combined with such fluids before being carried to the distal end of the tip 1460.

The final products being delivered to the skin can include, without limitation, human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance. Alternatively, such solids, gels and/or other materials can be impregnated or otherwise positioned along one or more exterior surfaces of the disc 1490 (e.g., along the inner diameter of the opening 1494). As discussed with reference to other embodiments disclosed herein, the disc 1490 can be partially or completely formed from such dissolvable or removable materials, so that it loses mass over time (e.g., as water or other liquids come in contact with it). In other embodiments, the disc 1490 comprises a porous container (e.g., cage) that is configured to house one or more solids, gels and/or other materials therein. In such arrangements, the disc 1490 can be removed, refilled, replaced and/or reused, as desired or required.

In FIGS. 15A and 15B, the stem 1464 of the tip comprises one or more side openings 1465 through which the materials and other substances contained on and/or within the disc 1490 may exit. Further, such openings 1465 can permit water, saline and/or other fluids being conveyed through the stem to enter an interior of the disc 1490 in order to advantageously dissolve, dilute and/or otherwise mix with the various materials contained therein. In some embodiments, the disc 1490 includes one or more openings that generally correspond to and align with the side openings 1465 of the stem 1460. Alternatively, the disc 1490, capsule or other item can comprise a cage or other porous structure to permit the various solids, gels, concentrated fluids and/or other materials contained therein to pass toward the opening 1465 of the stem 1464. Such materials and substances can be dissolved, diluted or otherwise mixed with water, saline and/or other fluids either within an interior cavity of the disc 1490, along an exterior portion of the disc, within the passage of the stem 1464 and/or at any other location or portion of the tip 1460.

Figure 16A:
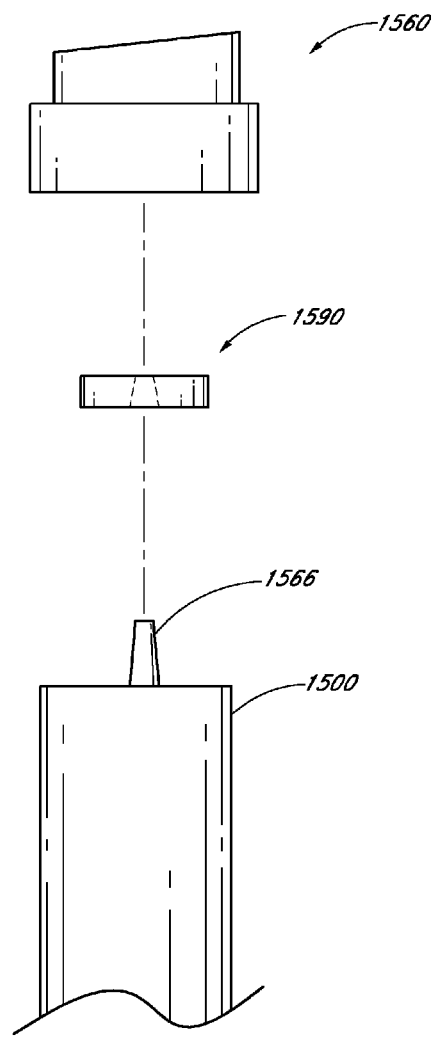
FIG. 16A schematically illustrates an exploded view of a handpiece assembly, a tip and a cartridge or other container according to another embodiment.
Figure 16B:
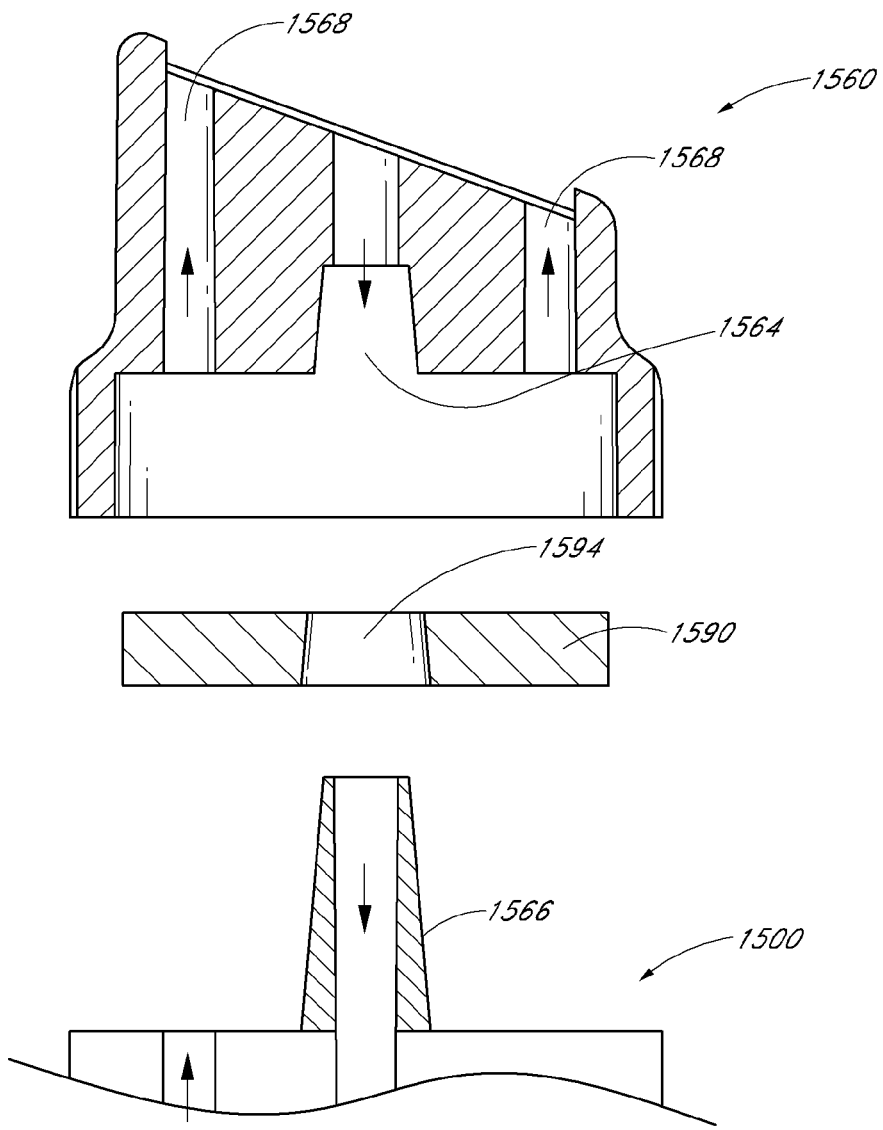
FIG. 16B illustrates an exploded cross-sectional view of another embodiment of a handpiece assembly, a tip and a cartridge or other container comprising solids, gels and/or other materials.

With reference to the schematic of FIG. 16A, a disc 1590, capsule or other item can be secured to a distal end of the main body portion 1500 of the handpiece assembly. For example, as illustrated in FIG. 16B, a central opening 1566 of the disc 1590 can be positioned over a nozzle 1566 or other protruding member of the handpiece assembly. As discussed with reference to other embodiments herein, including the discs of FIGS. 14A-14C, 15A and 15B, exterior and/or interior portions of the disc 1590 can include one or more solids, granulated materials, semi-solids, gels, concentrated fluids and/or other substances that are configured to be contacted by water, saline, other dilutants or dissolvents and/or other fluids. The resulting materials that are selectively delivered to the distal end of the tip 1560 (e.g., through one or more delivery passages or conduits 1568) can include, without limitation, growth factors, cytokines, soluble collagen, antioxidants, matrix proteins, serums, salicylic acid, other anti-acne acids and materials, microcapsules, capsules, other time-release products and substances, brightening or lightening agents, peptides, acid, water (e.g., distilled, tap water, filtered, etc.), saline, other dilutants or dissolvents, vitamins, chemical exfoliation agents, lotions, soothing agents, anesthetics, medicants, other non-active or active compounds, other fluids or materials, combination or mixtures thereof and/or any other substance.

Figure 17:
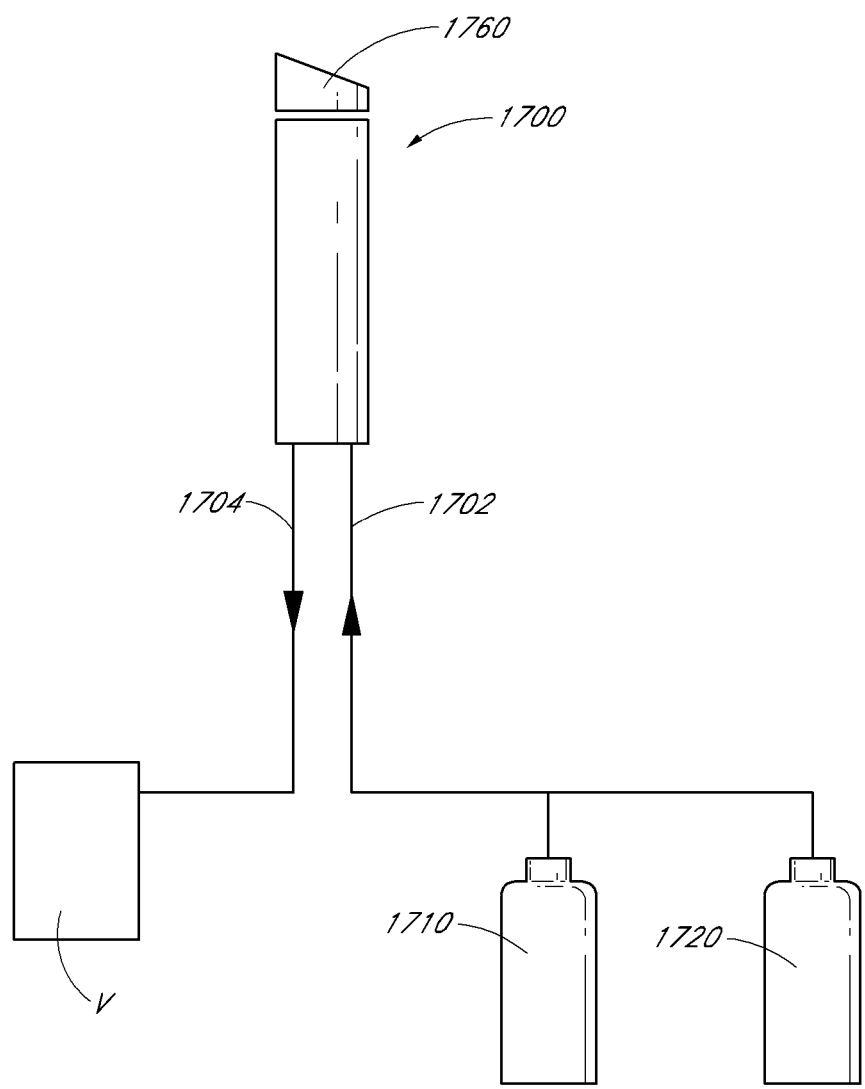
FIG. 17 schematically illustrates a handpiece assembly in fluid communication with a vacuum source and two supply containers according to one embodiment.

FIG. 17 schematically illustrates one embodiment of a handpiece assembly 1700 which is in fluid communication with a vacuum V or other suction force via a vacuum line 1704. In addition, the depicted assembly is in fluid communication with one or more containers 1710, 1720 via a delivery line 1702. As discussed herein, the delivery line 1702 can be placed in fluid communication with one or more different treatment materials, such as, for example, growth factors, cytokines, soluble collagen, antioxidants, matrix proteins, serums, salicylic acid, other anti-acne acids and materials, microcapsules, capsules, other time-release products and substances, water, saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance. Such materials can be selectively transferred from their respective containers, through the delivery line and to the handpiece assembly 1700 in their usable, ready-to-use form (e.g., with the concentration and other manner in which they will be delivered to the skin surface being treated).

Alternatively, water (e.g., tap, filtered, sterile, distilled, etc.), saline, other dilutants or dissolvents and/or other fluids can be stored within one or more of the containers 1710, 1720 located upstream of the handpiece assembly 1700. As discussed, such liquids and other fluids can be selectively delivered to the handpiece assembly 1700 in order to dissolve, dilute and/or mix with solids, gels, concentrated fluids, other materials and/or the like that are impregnated, deposited, stored or otherwise situated on or near the tip 1760.

In other embodiments, one or more of the upstream containers (e.g., container 1710 in FIG. 17) can be configured to store a cleaning solution. Accordingly, such solutions or other cleaning agents can be selectively conveyed through the delivery conduits 1702 and other interior portions of the handpiece assembly 1700, the tip 1760 and/or any other component or portion of a skin treatment system as part of a cleaning protocol. For example, the cleaning solutions and other agents can be used between skin treatment procedures, during a skin treatment procedure, in accordance with some predetermined cleaning schedule (e.g., once a day, once every two or three days, once a week, etc.), in accordance with some other desired or required protocol (e.g., to satisfy regulatory requirements, quality control standards, etc.) and/or the like. In some embodiments, the cleaning agents include biocides, antimicrobial solutions, disinfectants, other sterilizing agents and/or the like. Such a configuration that includes a handpiece assembly in fluid communication with one or more cleaning solutions or agents can be incorporated into any of the embodiments disclosed herein, or variations thereof.

Figure 18A:
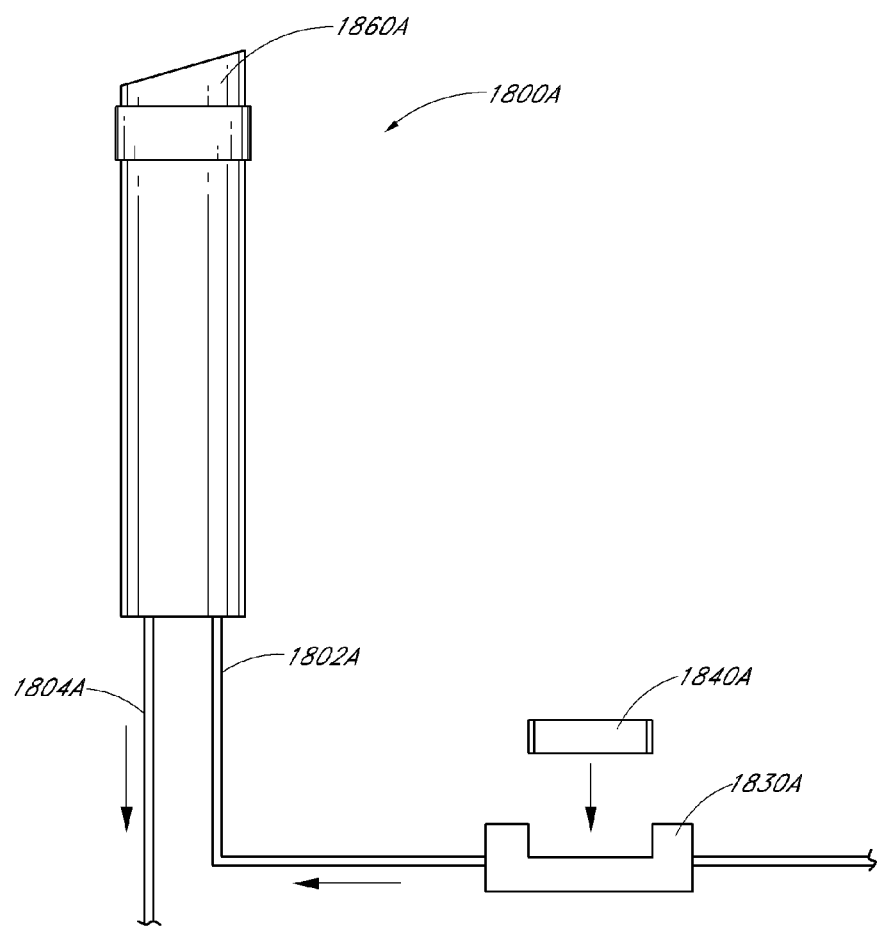
FIG. 18A schematically illustrates a handpiece assembly in fluid communication with a waste conduit and a supply conduit that comprises a cartridge holder adapted to receive a cartridge or other container according to one embodiment.

The schematic of FIG. 18A illustrates one embodiment of a skin treatment system that includes a handpiece assembly 1800A, a suction line 1804A in fluid communication with a vacuum or other suction source and a delivery line 1802A in fluid communication with one or more fluids, materials or other substances. As shown, the delivery line 1802A can include a cartridge holder 1830A or other device configured to accept a container 1840A. In some arrangements, the cartridge holder 1830A is sized, shaped and otherwise adapted to securely receive a standard or non-standard vial, ampoule and/or any other container 1840A. In certain configurations, such containers comprise one or more treatment fluids or other materials that can be selectively transferred to the tip 1860A during a procedure. As discussed, these substances can include, without limitation, growth factors, cytokines, soluble collagen, antioxidants, matrix proteins, brightening or lightening agents, peptides, peeling agents, acids, serums, salicylic acid, other anti-acne acids and materials, microcapsules, capsules, other time-release products and substances, water, saline, other dilutants or dissolvents, vitamins, chemical exfoliation agents, lotions, soothing agents, anesthetics, medicants, other non-active or active compounds, other fluids or materials, combination or mixtures thereof and/or the like.

According to certain embodiments, the fluids and/or other materials included in the cartridge 1840A are in their final, ready-to-use state. Thus, the contents of a cartridge 1840A can be directly delivered to the tip 1860A (e.g., as a result of a suction force imparted on the delivery line 1802A) without being diluted, dissolved or mixed with any other fluid or substance. Alternatively, a cartridge 1840A can comprise solids, granulated materials, gels, concentrated solutions and/or the like that are adapted to be combined with one or more fluids, other dissolvents or dilutants and/or other fluids (e.g., water, saline, etc.). For instance, such fluids can be conveyed from the upstream delivery line and combined with the internal contents of a cartridge 1840A or other container when such a cartridge 1840 is properly positioned within a holder 1830A.

The embodiment illustrated in FIG. 18A can provide a convenient way of selectively loading and unloading treatment fluids and/or other materials prior to, during or following a procedure. In some embodiments, fluids and/or other materials (e.g., water, other treatment fluids or substances, etc.) are configured to be conveyed through the cartridge holder 1830A from an upstream source even if a cartridge 1840A or other container is not positioned within the cartridge holder 1830A.

Figure 18B:
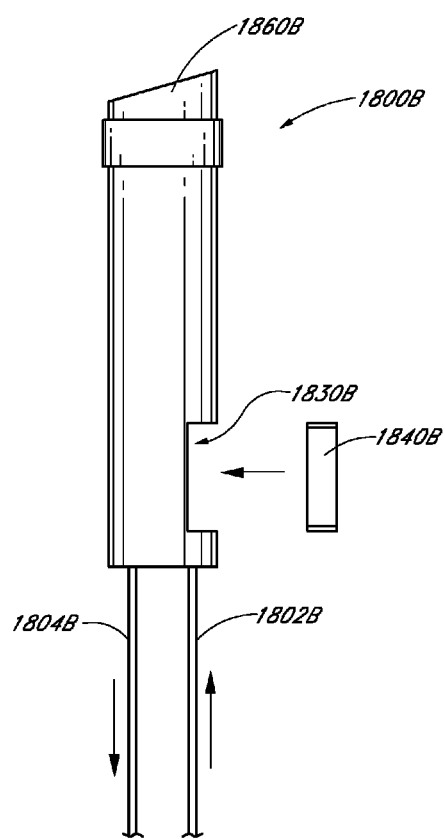
FIG. 18B schematically illustrates a handpiece assembly configured to receive a cartridge or other container according to one embodiment.

FIG. 18B illustrates a variation of the embodiment depicted in FIG. 18A. As shown, a standard or non-standard cartridge 1840B or other container can be configured to be selectively positioned within a corresponding slot or other receiving area 1830 of the handpiece assembly 1800B. As discussed with reference to FIG. 18A, the cartridge 1840A can comprise one or more treatment agents, fluids, materials and/or other substances. Such substances can be provided in their final, ready-to-use state. Alternatively, such materials can be provided as solids, granulated materials, gels, concentrated solutions and/or other forms that require contact and/or mixing with water, saline or the like before they are ready for use (e.g., prior to being delivered to the tip 1860 of the handpiece assembly, prior to contacting the skin, etc.). The embodiments illustrated in FIGS. 18A and 18B can be incorporated into any of the embodiments of a skin treatment system disclosed herein, or variations thereof.

Figure 19A:
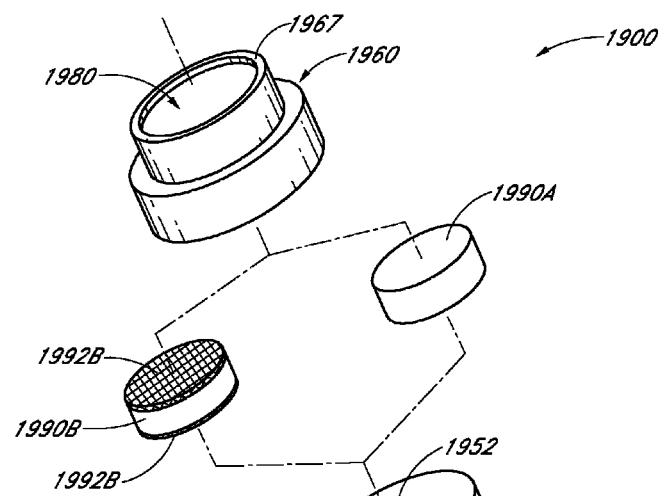
FIG. 19A illustrates an exploded perspective view of a handpiece assembly, a tip and pads configured to be secured therebetween according to one embodiment.

FIG. 19A illustrates another embodiment of a handpiece assembly 1900 adapted for use in a microdermabrasion or other skin treatment system. As shown, the handpiece assembly 1900 can include a main body portion 1910 and a tip 1960 configured to removably attach to the distal end of the main body portion 1910. The main body portion 1910 can include one or more conduits passing therethrough. In the depicted arrangement, the main body portion 1910 includes a single removal conduit 1950 which is positioned at or near the longitudinal centerline of the handpiece assembly and which daylights at an opening 1952 at the distal end of the main body portion 1910. The removal conduit 1950 can be placed in fluid communication with a vacuum or other suction source using a waste conduit 1954 to selectively transfer exfoliated skin, spent treatment fluids, debris and other waste materials away from the tip 1960.

Figure 19B:
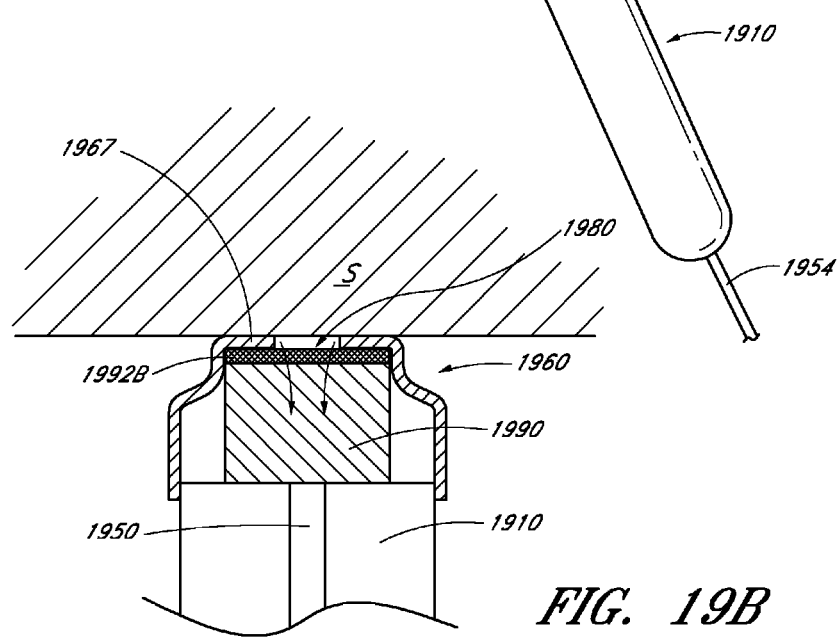
FIG. 19B illustrates a cross-sectional view of the tip, a pads and the handpiece assembly of FIG. 19A.
Figure 20A:
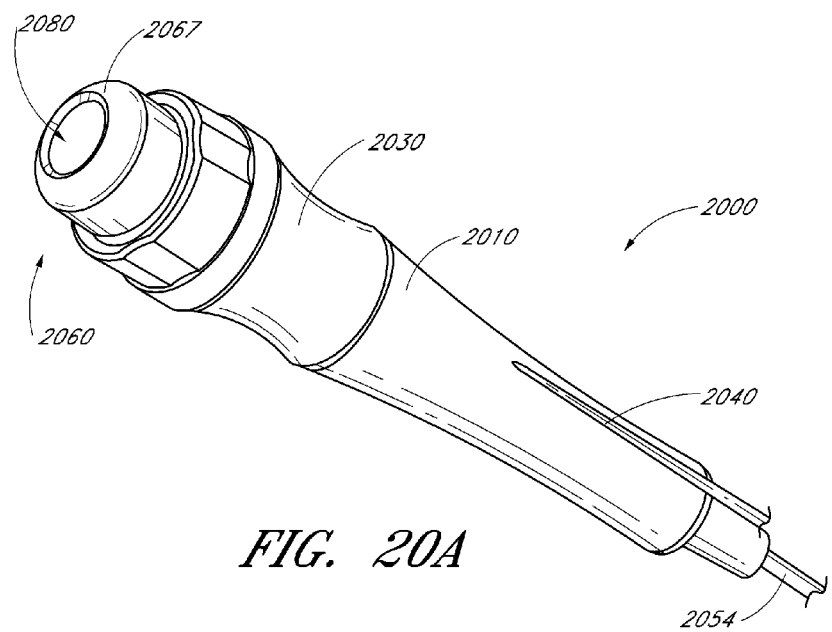
FIG. 20A illustrates an perspective view of a handpiece assembly configured to receive a pad according to another embodiment.
Figure 20D:
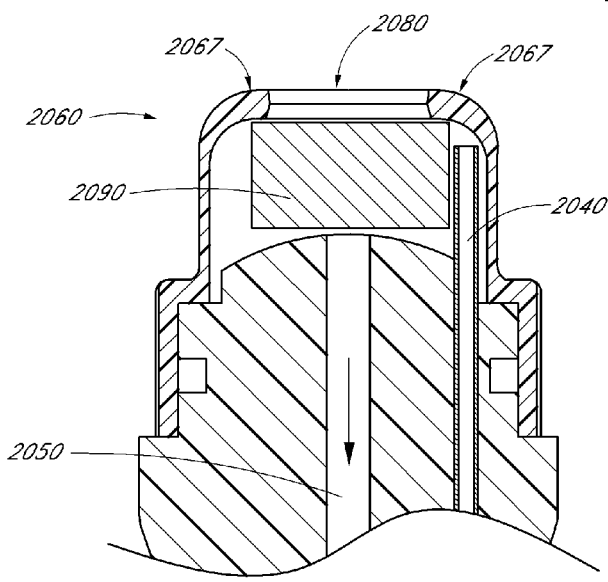
FIG. 20D illustrates a detailed cross-sectional view of the handpiece assembly of FIG. 20A comprising a pad secured within an interior portion of its tip according to one embodiment.
Figures 20B, 20C:
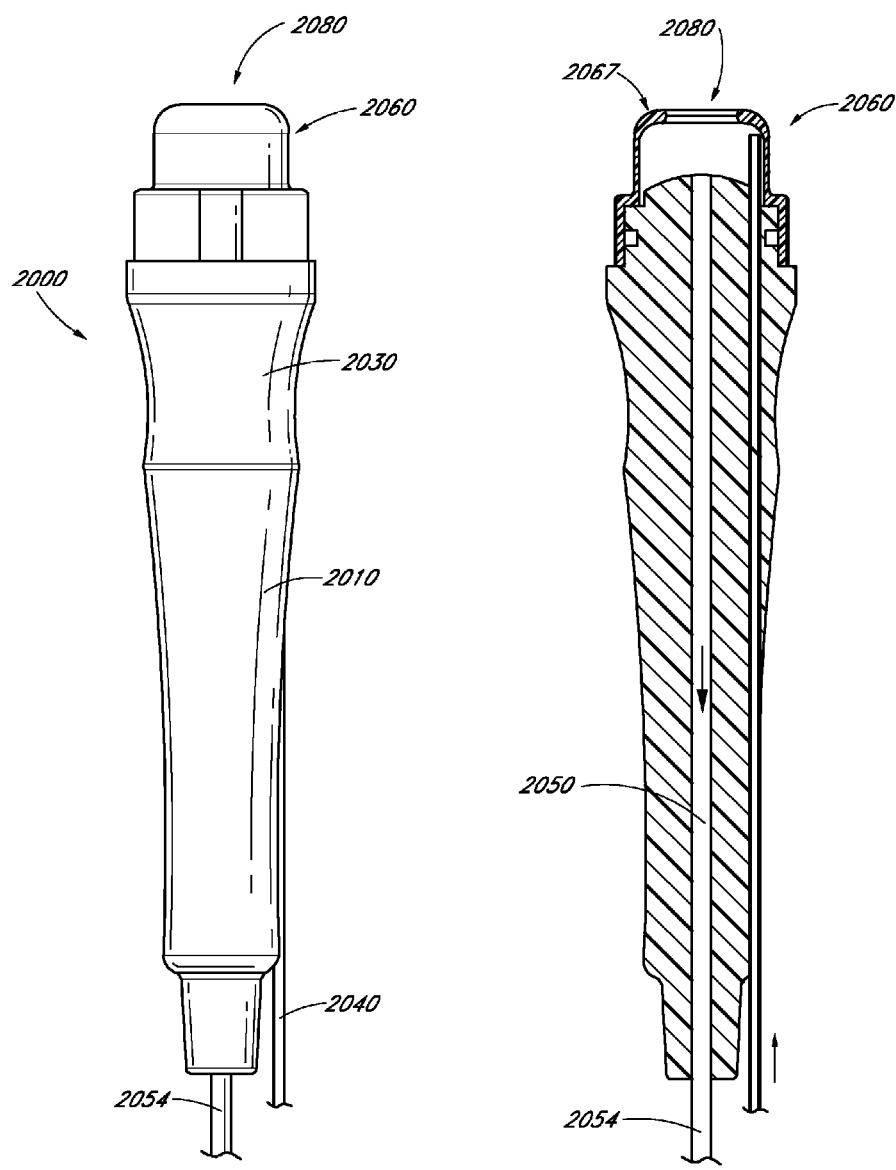
FIG. 20B illustrates a side view of the handpiece assembly of FIG. 20A.
FIG. 20C illustrates a cross-sectional view of the handpiece assembly of FIG. 20A.

With continued reference to FIG. 19A, the distal end of the tip 1960 can include one or more openings 1980 defined within a peripheral lip 1967. According to certain arrangements, the handpiece assembly 1900 is sized, shaped and otherwise configured to receive a removable pad 1990A, 1990B or other member within an interior of the tip 1960. Thus, as illustrated in FIGS. 19A and 19B, such a pad 1990A, 1990B or other member can be generally positioned between the tip 1960 and the main body portion 1910 when the tip 1960 is properly secured to the handpiece assembly 1900. The pads can have a diameter (or other cross-sectional dimension) that is greater than the opening 1980 along the distal end of the tip 1960. Accordingly, the pad 1990A, 1990B or other member can be securely retained below the opening 1980 and within the tip 1960 during use.

As illustrated in the cross-sectional view of FIG. 19B, an upper surface of the pad 1990 can be configured to contact a skin surface S through the tip opening 1980 during use. Thus, in some embodiments, the upper surface of a pad is configured to exfoliate skin when it is translated or otherwise moved relative to a skin surface. The pad 1990 can comprise foam and/or any other materials. In one arrangement, the pad 1990 comprises one or more polymeric materials. However, the pads or other device can include one or more other natural or synthetic materials, either in lieu of or in addition to plastics and other polymers, as required to achieve a desired texture, coarseness, roughness and/or other exfoliation characteristics.

In some embodiments, as illustrated in FIG. 19A, the upper and/or lower surfaces 1992B of the pad 1990B include a texture that is coarser than other portions of the pad 1990B. For example, the pad 1990B can include grit, a sandpaper-like finish, an uneven finish, harder or more rigid materials and/or the like along its upper and/or lower surfaces 1992B. Such a configuration can further enhance the skin exfoliating properties of the pad. In arrangements where it includes both upper and lower textured surfaces 1992B, the pad 1990B can be flipped to selectively place the desired surface 1992B along the distal end of the tip 1960. For example, after the first surface 1992B has been used for a particular time period or after the effectiveness of the first surface 1992B has generally diminished or deteriorated, a user can remove the tip 1960 and turn the pad 1990B around to expose the second surface 1992B to the skin surface S being treated. This can effectively extend the useful life of a pad. In other embodiments, however, a pad 1990A can include one or no textured surfaces. For instance, a pad 1990A without any roughened surfaces can be used as a final, polishing skin surfacing step. According to certain embodiments, a user can be provided with an assortment of pads 1990 each of which having varying skin surfacing characteristics. Thus, a user can customize his or her treatment procedure, as desired or required.

According to some embodiments, as shown in FIG. 19A, the pads are cylindrical is shape with generally flat upper and lower surfaces. However, the shape, size and/or other characteristics of the pads 1990 can vary. The pad 1990 can serve an additional function by being configured to filter some or all of the debris and other waste item being transferred from the distal end of the tip 1960 to the waste opening 1952 and removal conduit 1950 of the main body portion 1910. For example, the pad 1990 can comprise foam or another porous structure that effectively functions as a filter to help trap exfoliated skin and other waste materials. Thus, by preventing or reducing the amount of debris passing to the removal conduit 1950, the pad 1990 can advantageously extend the life of the handpiece assembly 1900 and the downstream components of the skin treatment system (e.g., the waste container, the waste line 1954, downstream filters, the vacuum or other suction source, etc.).

In some embodiments, a procedure may be enhanced by providing one or more treatment fluids, serums salicylic acid, other anti-acne acids and materials, microcapsules, capsules, other time-release products and substances and/or other materials to the skin surface being treated. For example, as discussed in greater detail herein, it may desirable to selectively provide human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, anesthetics, medicants, other non-active or active compounds, other fluids or materials, combination or mixtures thereof and/or any other substance to the tip 1960 of the handpiece assembly 1900. As discussed, such fluids and/or other materials can be delivered to the tip 1960 using one or more delivery conduits, passages and other hydraulic components of the handpiece assembly 1900.

However, in embodiments which do not include such passages, such as the one illustrated in FIGS. 19A and 19B, the desired fluids and/or other materials can be included within the pad 1990 or other device situated between the tip 1960 and the main body portion 1910 of the assembly 1900-. Therefore, solids, gels, fluids and/or other materials included within the pads 1990 can be advantageously excreted or discharged onto the skin surface S during a treatment procedure. Such materials can be positioned within the pad body (e.g., foam or other absorbent structure), on the surface of the pad and/or at any location or region of the pad, as desired or required.

In order to adequately maintain the desired treatment fluids and/or other materials within the pads 1990, the pads 1990 can be included in an enclosed pouch or other sealed container. This will help ensure that the desired materials remain within and/or on the pad 1990 until such pads 1990 are inserted into a handpiece assembly 1900. In other embodiments, the pads include one or more solids, granular materials, gels, concentrated fluids and/or other substances that are configured to be contacted with water, saline, other dilutants or dissolvents and/or other fluids in order to convert them into a usable treatment material or mixture. Thus, an external fluid source can be used with the handpiece assembly 1900 of FIG. 19A. Alternatively, as discussed herein with reference to the embodiment of FIGS. 20A-20D and FIGS. 21A-21B, a handpiece assembly can comprise one or more fluid delivery conduits of its own. Additional information regarding tips configured to receive a pad or other device is provided in U.S. patent application Ser. No. 09/699,220, filed on Oct. 27, 2000 and issued on Oct. 7, 2003 as U.S. Pat. No. 6,629,983, the entireties of which is hereby incorporated by reference herein.

The handpiece assembly 2000 illustrated in FIGS. 20A-20D is similar to the embodiment of FIGS. 19A and 19B. However, the depicted embodiment additionally comprises a fluid delivery conduit 2040 that is configured to deliver one or more fluids, treatment materials and/or the like toward the skin surface being treated. As discussed in greater detail herein with reference to other arrangements, human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance can be delivered through the delivery conduit 2040. In other embodiments, the delivery conduit 2040 is adapted to convey water, saline, other dilutants or dissolvents and/or other fluids to the tip 2060 where they can be selectively mixed, combined or contacted with solids, semi-solids, gels, granulated materials, concentrated fluids or materials and/or the like in order to produce the desired treatment materials. As discussed with reference to other embodiments herein, such solids and/or other materials can be embedded, impregnated and/or otherwise disposed on, within or along the tip 2060, the pad 2090 (e.g., foam), a cartridge and/or any other component or portion which is in fluid communication with the handpiece assembly 2000.

Figures 21A, 21B:
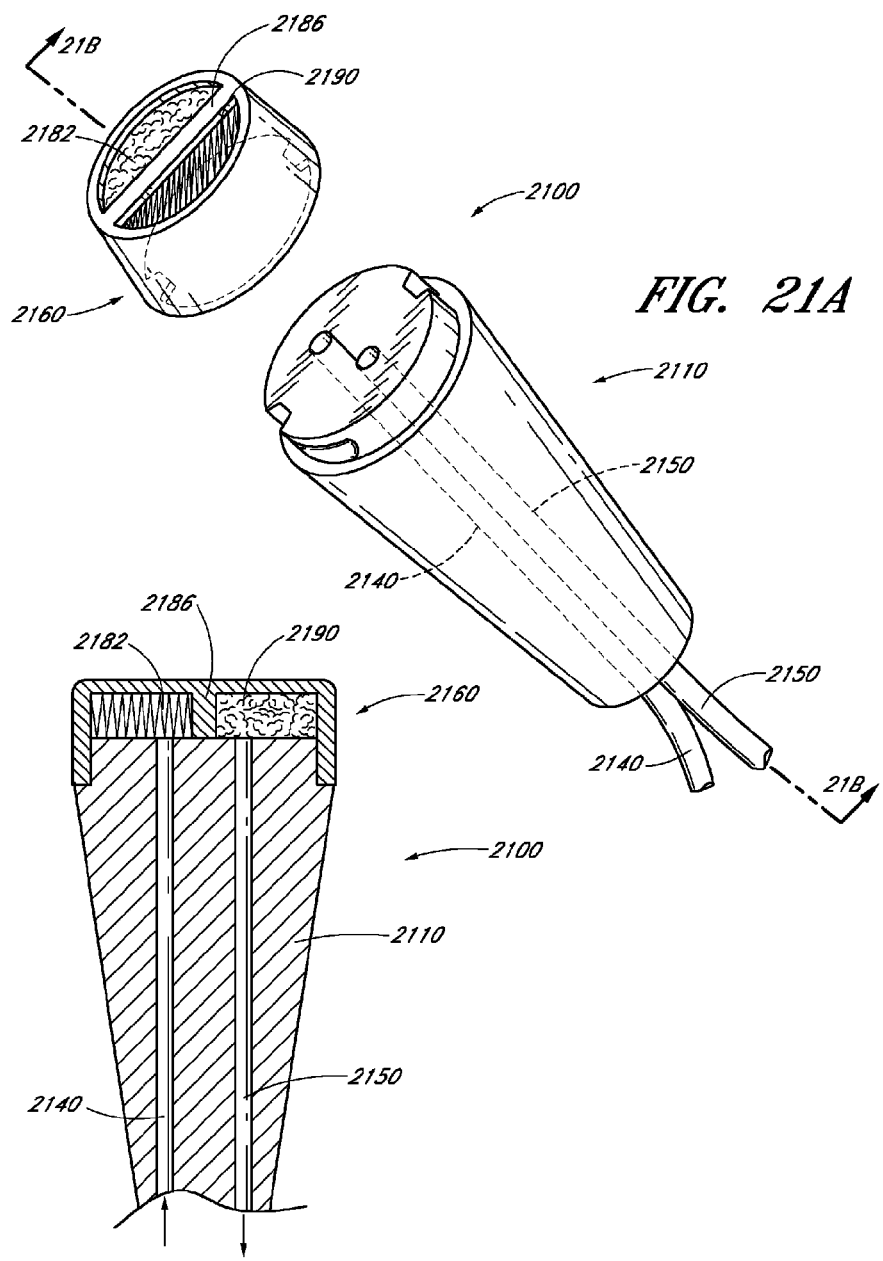
FIG. 21A illustrates an exploded perspective view of a handpiece assembly that is adapted to be in fluid communication with a vacuum source and a fluid delivery source according to one embodiment.
FIG. 21B illustrates a cross-sectional view of the handpiece assembly of FIG. 20A.

Another embodiment of a handpiece assembly 2100 is illustrated in FIGS. 21A and 21B. The main body portion 2110 of the assembly 2100 can include a delivery conduit 2140 and a waste conduit 2150. According to some embodiments, these conduits 2140, 2150 are routed along an interior of the main body portion 2110. However, one or both of these conduits can be positioned along the outside of the handpiece assembly 2100, as desired or required. Further, a removable tip 2160 can be configured to be secured along the distal end of the main body portion 2110.

With continued reference to FIGS. 21A and 21B, the tip 2160 can include a delivery zone 2182 or region and a waste zone 2190 or region. As shown, these zones 2182, 2190 can be separated by a septum 2186 or other member or feature. According to some embodiments, treatment fluids and/or other materials, such as, for example, human growth factors, cytokines, soluble collagen, antioxidants, matrix proteins, serums, salicylic acid, other anti-acne acids and materials, microcapsules, capsules, other time-release products and substances, water (e.g., distilled, tap water, filtered, etc.), saline, other dilutants or dissolvents, vitamins, chemical exfoliation agents, lotions, soothing agents, brightening or lightening agents (e.g., kojic acid), peptides, peeling agents, acids, anesthetics, medicants, other non-active or active compounds, other fluids or materials, combination or mixtures thereof and/or any other substances, are selectively transferred to the delivery zone 2182 via the delivery conduit 2140. Such fluids and/or other materials can originate from a cartridge (e.g., located within the handpiece assembly 2100, positioned upstream of the handpiece assembly 2100, etc.), a bottle or other container included as a part of a manifold system and/or any other source.

Alternatively, the delivery conduit 2140 can be configured to transfer only water, saline, other dilutants or dissolvents and/or other relatively clean fluids (e.g., fluids that have no solids or a low concentration of solids). In such configurations, as discussed in greater detail herein with reference to other arrangements, solids, semi-solids, granular materials, gels, concentrated solutions and/or other materials configured to be combined with the water, saline or other fluids being conveyed through the delivery conduits 2140 can be positioned within or near the delivery zone 2182. Thus, once water, saline and/or other fluids contact such materials, the desired or required treatment materials can be produced in the delivery zone 2182 and brought to the skin surface being exfoliated.

With further reference to FIGS. 21A and 21B, exfoliated skin, spent fluids and other treatment materials, debris and other waste materials can be removed from the tip 2160 to the waste conduit 22150 through the waste zone 2190. According to some embodiments, one or both of the zones 2182, 2190 include a pad or other member. For example, the delivery zone 2182 can include a pad or other member to help distribute the treatment fluids more evenly to the adjacent skin surface. In other arrangements, the pad or other member positioned within the delivery zone 2182 is saturated with or otherwise provided with solids, gels and/or other materials that can be selectively released to the skin once water or other fluids are conveyed to the delivery zone 2182. Likewise, the waste zone 2190 can include a pad or other member to help exfoliate skin and/or serve as a primary filter for the waste materials being carried away from the tip 2190.

Figure 22:
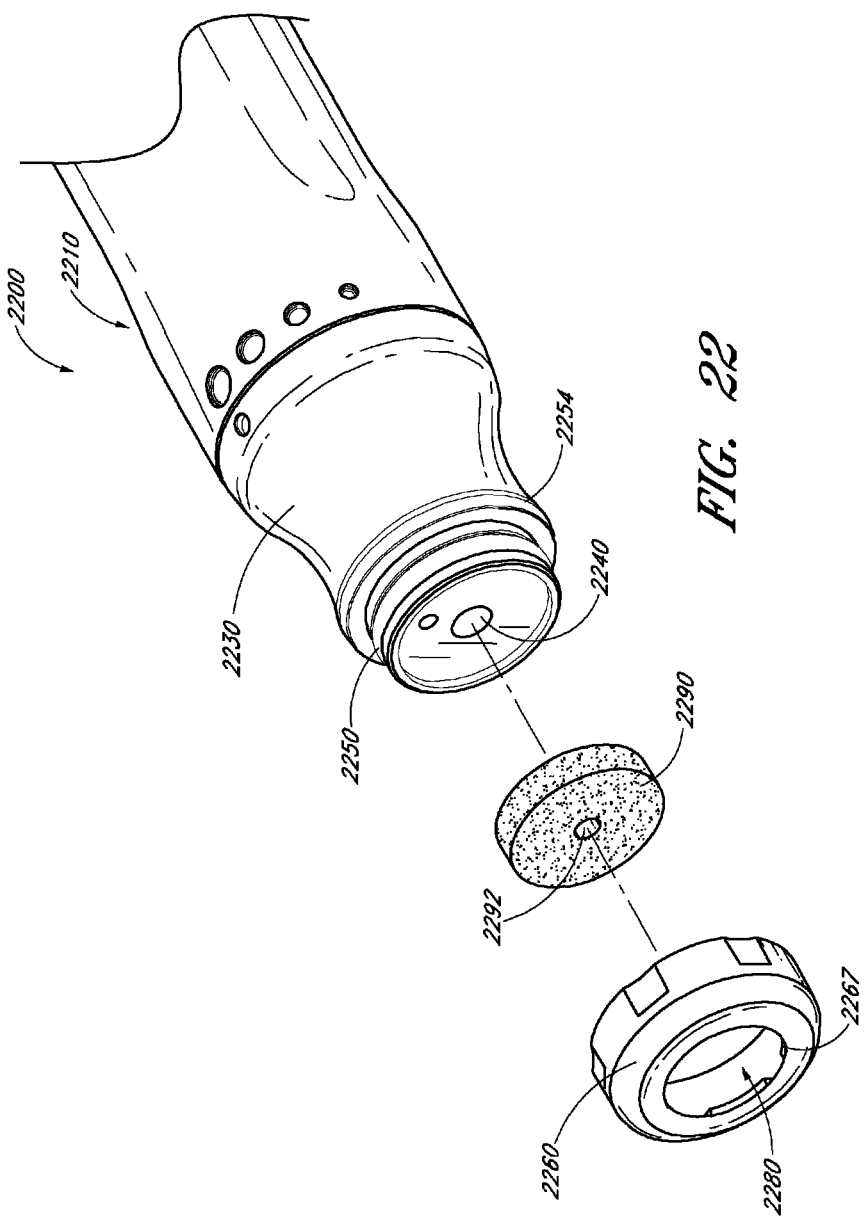
FIG. 22 illustrates a perspective view of a handpiece assembly configured to receive an abrasive disc according to one embodiment.

FIGS. 22, 23A and 23B illustrate an embodiment of a handpiece assembly 2200 configured to releasably receive a disc 2290, plate or any other member having an abrasive element along one or more of its surfaces. As shown, the disc 2290 can be sized, shaped and otherwise configured to be securely positioned within an interior of the tip 2260, generally between the tip's main opening 2280 and the front of the adjustable distal portion 2230 of the handpiece assembly 2200. According to certain arrangements, the disc 2290 or plate is adapted to be positioned within a recessed area (e.g., ring) located along an end surface of the handpiece assembly (e.g., the adjustable distal portion 2230) and/or the proximal interior portion of the tip 2260 (e.g., generally below the peripheral lip 2267). In embodiments where the handpiece assembly does not include an adjustable distal portion, the disc 2290 can be located within a corresponding recess of the main body portion 2210 or any other component of the handpiece assembly 2200.

As depicted in the cross-sectional view of FIG. 23A, the diameter or other cross-sectional dimension of the disc 2290, plate or similar member can be larger than the opening 2280 of the tip 2260. Thus, such a design helps ensure that the disc 2290 will remain securely positioned within an interior region of the tip 2260 during use. The abrasive elements positioned on the surface of the disc 2290 can be exposed through one or more openings 2280 of the tip 2260. Accordingly, as discussed in greater detail herein with reference to other embodiments, such abrasive elements can be used to selectively abrade skin during a treatment procedure.

In some arrangements, the disc 2290, plate or other member includes a plurality of diamonds or other materials, posts, sharp edges (e.g., the spiral or other protruding portions as illustrated in FIGS. 5A, 8A-8E, 9A-9F, 10A-10F and/or the like), other abrasive designs or features and/or any other abrasive element. As noted above, the term "abrasive element," as used herein, is a broad term and includes, without limitation, protruding elements, abrasive materials (e.g., grit, sandpaper-like material, other coarse materials, etc.), roughened surfaces, contoured surfaces, surfaces with openings, recesses or other features, brushes, blades, surfaces impregnated with diamonds or other materials and/or the like.

The disc 2290 can include diamonds and/or other abrasive elements on one or both of its surfaces. In arrangements where both sides of the disc 2290 include abrasive elements, the disc 2290 can be advantageously turned around to provide additional and/or different skin treatment options. For example, one side of the disc 2290 can comprise a texture or design configured to be used during an initial treatment step, while the opposite side of the disc 2290 can comprise a texture or design configured to be used during a follow-up or polishing step. Relatedly, the discs 2290, plates or other members can be provided with varying abrasive properties, allowing a user to quickly and conveniently customize the handpiece assembly 2200, as desired or required for a particular treatment procedure. For example, the grit size, density, spacing, location and/or other characteristics of the diamonds or other abrasive elements can vary from disc to disc.

As discussed herein with reference to other embodiments, the illustrated handpiece assembly 2200 can include one or more delivery channels 2240 and/or one or more removal channels 2250. Accordingly, the abrasive disc 2290, plate or other member adapted to be positioned between the tip 2260 and the distal end of the handpiece assembly 2200 can include one or more openings 2292 to facilitate fluids (e.g., water, serums, etc.) and/or other materials to be delivered to the skin interface and waste materials (e.g., abraded skin, spent treatment fluids, etc.) to be removed from the skin interface. In the illustrated embodiment, the disc 2290 includes only a single, centrally-located, circular opening 2292. However, in other arrangements, a disc 2290, plate or other abrasive member can include one or more additional openings. The quantity, size, shape, location, spacing and/or other details of such openings 2292 can be different than illustrated herein.

According to certain embodiments, the disc 2290, plate or other device having an abrasive element can be selectively removed (e.g., by removing the tip 2260 from the proximal portions of the handpiece assembly 2200). Thus, the disc or other member can be conveniently cleaned, serviced or replaced, as desired or required. This can help improve the effectiveness of a skin treatment procedure. In addition, such embodiments provide a convenient way of cleaning and/or otherwise maintaining a skin treatment system. Further, such designs can help improve the general efficiency of skin treatment procedures, as a system can be quickly cleaned and customized both between treatment procedures (e.g., different patients) and during the execution of a single treatment procedure (e.g., changing the grit size for a patient). A removable disc 2290, plate or other member, as illustrated in FIGS. 22, 23A and 23B and discussed above, or equivalents thereof, can be incorporated into of the embodiments disclosed herein or equivalents thereof.

As noted above, one or more materials can be strategically embedded, impregnated, placed, stored and/or otherwise disposed on one or more surfaces or areas of the disc 2290 and/or any other portion or component of the handpiece assembly 2200. Such materials can comprise solids, semi-solids, other dried substances, gels, concentrated solutions and/or the like. For example, such materials can be provided in loose form (e.g., positioned on or within the disc 2290, a recess of the disc 2290, other portion of the tip 2260, within a cartridge or other container, adhered to one or more surfaces, etc.), as a tablet, capsule, pill, disc or other dissolvable solid, saturated within a foam pad or other sponge-like material and/or the like. Thus, in certain arrangements, water (e.g., distilled, tap water, filtered, etc.), saline, other dilutants and/or other fluids which are delivered through the disc 2290, plate or other abrasive member to the tip can selectively dissolve, liquefy, melt, soften, dilute or otherwise prepare the materials embedded, impregnated and/or otherwise positioned on the tip, within a cartridge or other container and/or on or within another portion or component of a skin treatment system (e.g., handpiece assembly, fluid line upstream of the handpiece assembly, etc.). Accordingly, the desired human growth factors, cytokines, soluble collagen, antioxidants, matrix proteins, serums, salicylic acid, other anti-acne acids and materials, microcapsules, capsules, other time-release products and substances, water, saline, other dilutants or dissolvents, vitamins, chemical exfoliation agents, lotions, soothing agents, brightening or lightening agents, peptides, acids, anesthetics, medicants, other non-active or active compounds, other fluids or materials, combination or mixtures thereof and/or any other substance can be advantageously provided to the skin surface being treated, as desired or required.

FIG. 24 illustrates one embodiment of a handpiece assembly 3010 configured for use in a skin treatment system which may be used to perform one or more treatments on a person's skin. In the depicted embodiment, the handpiece assembly 3010 comprises an outer housing 3014 that can be grasped or otherwise manipulated by a user. As shown, the housing 3014 can include a curved shape. In other embodiments, the shape, size and/or other details regarding the housing 3014 can vary as desired.

With continued reference to FIG. 24, the handpiece assembly 3010 can include a tip 3020 that is configured to contact or substantially contact the skin or other surface being treated. According to some embodiments, as illustrated in FIG. 24, the tip 3020 can be removable. Thus, the tip 3020 can be easily changed for cleaning, hygienic or other purposes. For example, depending on the type of skin treatment procedure being performed, a user can select a tip 3020 having a specific pattern or features along the distal end. Non-limiting examples of the various types of tips 3020 that may be attached to the handpiece assembly 3010 are disclosed in U.S. patent application Ser. No. 11/392,348, filed Mar. 29, 2006 and published as U.S. Patent Publication No. 2007/0156124, and U.S. patent application Ser. No. 12/362,353, filed Jan. 29, 2009 and published as U.S. Patent Publication No. 2009/0192442, the entireties of both of which are hereby incorporated by reference herein.

In arrangements where a removable tip 3020 is used, the handpiece assembly 3010 can include an interface portion 3030 along its distal end that is configured to securely receive the tip 3020. In FIG. 24, the interface portion 3030 comprises an O-ring 3040 or other sealing member to help prevent or reduce the likelihood of leaks. In other embodiments, one or more other types of gaskets or similar devices can be used, either in lieu of or in addition to an O-ring 40.

With continued reference to FIG. 24, the interface portion 3030 can include one or more openings 3044, 3046 or ports. In some embodiments, these openings 3044, 3046 are configured to transfer fluids and/or other materials to and/or from the tip 3020. For example, in the depicted embodiment, the interface portion 3030 comprises two fluid delivery openings 3044 positioned along the periphery and one fluid suction opening 3046 positioned along the center of the handpiece assembly 3010. In other embodiments, however, the number, location, spacing, shape, size and/or other details of the openings 3044, 3046 can vary as desired or required.

One or more conduits 3050 can be placed in fluid communication with the openings 3044, 3046, and thus, at least a portion of the tip 3020 of the handpiece assembly 3010. The conduits 3050 can be configured to transfer (e.g., deliver, withdraw, etc.) fluids or other materials to and/or from the distal end of the handpiece assembly 3010. As shown in FIG. 24, the conduit 3050 can be positioned at least partially within an interior portion of a handpiece assembly 3010. In the depicted embodiment, the conduit 3050 extends out of the proximal end of the handpiece assembly 3010.

FIG. 25A illustrates one embodiment of a conduit 3050 that is configured for use in a handpiece assembly 3010. As shown, the conduit 3050 can include a delivery passage 3054 and a suction passage 3056. In other embodiments, the conduit 3050 can comprise more or fewer passages, as desired or required by a particular application or use. In addition, the size, shape and other details of the passages 3054, 3056 can be different than illustrated in FIGS. 25A and 25B. The conduit 3050 can comprise tubing, pipe and/or the like. Further, the conduit 3050 can include one or more rigid, semi-rigid and/or flexible materials, such as, for example, rubber, plastic, other polymeric materials, other synthetic materials, metal or the like.

With continued reference to FIG. 25A, the various passages 3054, 3056 of the conduit 3050 can be co-molded or otherwise produced as a unitary structure. In FIG. 25A, the passages 3054, 3056 are attached to each other along a portion of the conduit 3050 and separated from each other along another portion of the conduit 3050. According to some embodiments, the conduit 3050 can be manufactured using extrusion or other production method. In other arrangements, individual passages that connect to the handpiece assembly 3010 are separate members that may or may not be attached to one another. For example, in one embodiment, the passages 3054, 3056 can comprise separate rubber tubing portions that are joined to each other using adhesives, clips, tape, fasteners and/or one or more other attachment methods or devices. The shape, size and/or other details of the passages 3054, 3056 can be different than illustrated herein.

Figure 26:
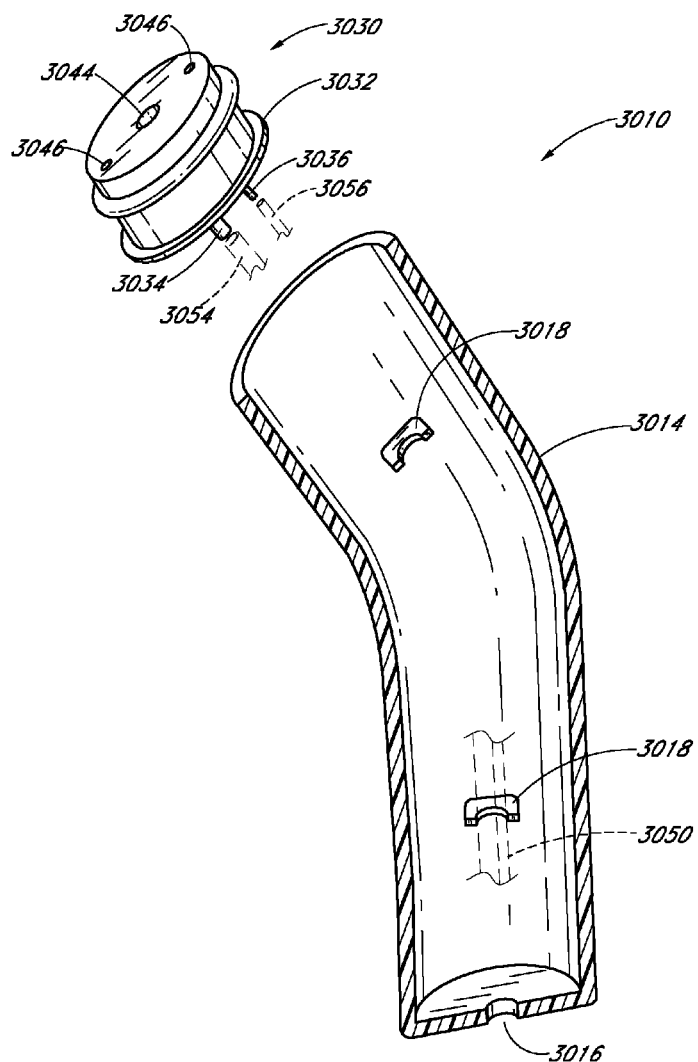
FIG. 26 illustrates a perspective view of a handpiece assembly with a portion of the exterior surface removed to reveal an interior portion of the assembly according to one embodiment.

FIG. 26 illustrates an exploded perspective view of the handpiece assembly 3010 of FIG. 24 with a portion of the outer housing 3014 removed to reveal an interior area. As shown, an interior of the handpiece assembly 3010 can comprise one or more tabs 3018, guides, other fasteners and/or other members that are shaped, sized and otherwise configured to receive and secure one or more conduits 3050 extending within the assembly 3010. By way of example, in FIG. 26, a small portion of a conduit 3050 is shown (in phantom) within one of the tabs 3018. In the illustrated embodiment, the handpiece assembly 3010 includes a total of two tabs 3018. However, the quantity, type, shape, size and/or other details of the tabs 3018 or other members can vary. Further, the proximal end of the handpiece assembly 3010 can comprise an opening 3016 or other slot through which a conduit 3050 and/or other items can extend.

With continued reference to FIG. 26, the interface portion 3030 of the handpiece assembly 3010 can include one or more ports 3034, 3036 that are configured to attach to passages 3054, 3056 of a conduit 3050. For example, in FIG. 26, the delivery passage 3054 is shown (in phantom) as being associated with a first port 3034 and the suction passage 3056 is shown (in phantom) as being associated with a second port 3036. In other embodiments, a handpiece assembly 3010 comprises more or fewer ports, as desired or required. In addition, the size, shape, type and/or other details of the ports can vary. In some embodiments, once the tubing 3050 is properly secured to the ports 3034, 3036 of the handpiece assembly, the delivery passage 3054 can be placed in fluid communication with the one or more delivery openings 3044. Likewise, the suction passage 3056 can be placed in fluid communication with the one or more suction openings 3046. Consequently, one or more fluids or other materials can be selectively transferred (e.g., delivered to and/or removed from) the tip 3020 of the handpiece assembly 3010.

As illustrated in FIG. 26, the assembly 3010 can be configured such that a single port 3036 can be in fluid communication with two or more openings 3046 located along a distal surface of the interface portion 3030. In other embodiments, a single opening along the distal surface of the interface portion 3030 can be in fluid communication with two or more ports. Thus, the interface portion 3030 can include one or more internal channels, flow splitting devices, flow control valves and/or any other devices or features that can selectively affect the flow of fluids therethrough. This can apply to delivery and/or suction ports and openings, as desired or required by a particular application.

The use of a conduit 3050 that extends within an interior cavity of the handpiece assembly 3010 can provide one or more advantages or benefits. For example, such designs can permit a user to easily remove, attach or replace a conduit 3050 between or during a treatment or procedure. In addition, contamination of an interior of the handpiece assembly 3010 can be reduced or eliminated because fluids or other substances transmitted through the handpiece assembly 3010 are fully contained within the passages 3054, 3056 of the conduit 3050.

Figure 27:
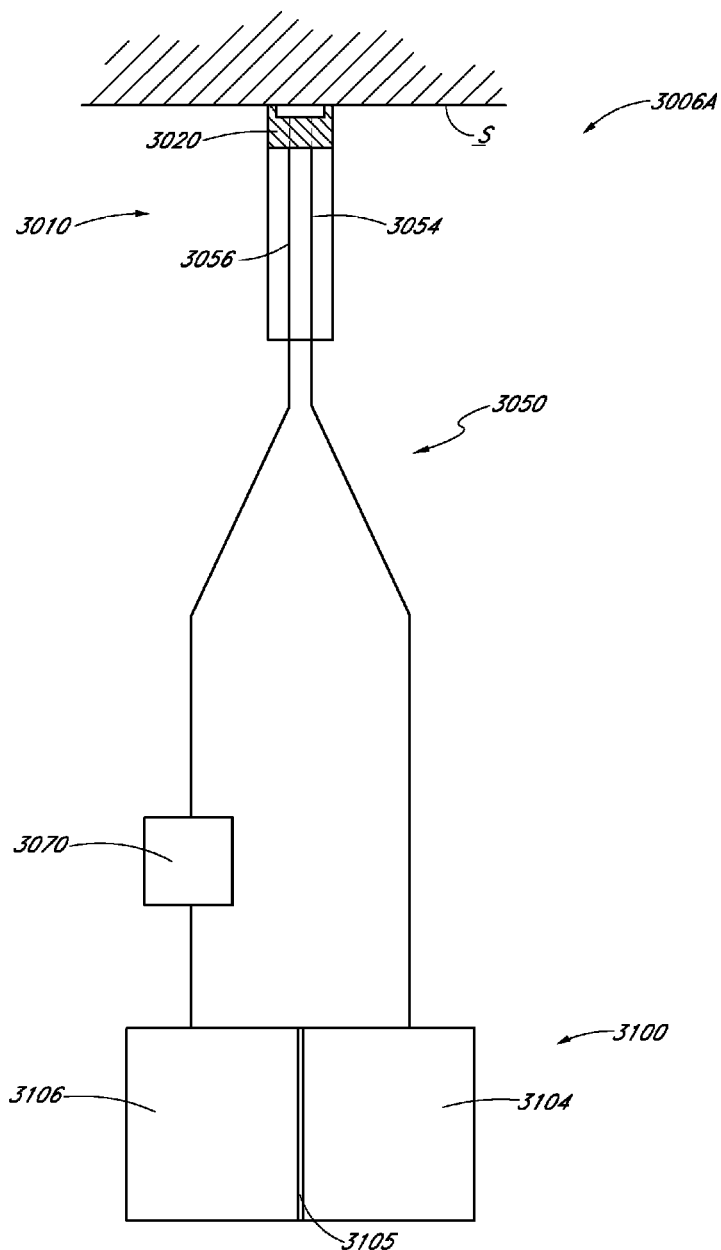
FIG. 27 schematically illustrates one embodiment of a skin treatment system according to one embodiment.

FIG. 27 schematically illustrates one embodiment of a skin treatment system 3006A. The depicted treatment system 3006A comprises a handpiece assembly 3010, a conduit 3050, a fluid transfer device 3070 (e.g., pump) in fluid communication with the conduit 3050 and a canister 3100 or other container. As shown, the handpiece assembly 3010 can include a tip 3020 that is adapted to contact and treat the skin S. A conduit 3050 having a delivery passage 3054 and a suction (e.g., removal) passage 3056 can be attached to the handpiece assembly 3010 and placed in fluid communication with the tip 3020. In addition, a pump 3070 or other fluid transfer device can be placed in fluid communication with the conduit 3050 (e.g., the suction passage 3056) to assist in transferring fluids or other materials to and/or from the tip 3020.

With continued reference to FIG. 27, the canister 3100 or other container can comprise a storage compartment 3104 and a waste compartment 3106. In other arrangements, the canister 3100 can include more or fewer compartments, as desired or required. For example, the canister 3100 can include two or more storage compartments, each of which is configured to store a different fluid and/or other treatment media. In some embodiments, the canister 3100 comprises a unitary structure having one or more baffles 3105 or other dividing members to create two or more separate compartments 3104, 3106. However, in other embodiments, the system 3006A comprises two or more separate canisters that are not part of a unitary structure or that are not attached to each other.

In FIG. 27, when the tip 3020 is placed against the surface of the skin S to be treated, a pump 3070 or other fluid transfer device can be used to draw a treatment media (e.g., water, saline, other fluids, other materials, etc.) from the storage compartment 3104 and through the delivery passage 3054. At the same time, the pump 3070 can remove waste materials from the treatment surface to the waste compartment 3106 via the suction passage 3056. In other embodiments, one or more other methods and/or devices for delivering and/or withdrawing fluid or other materials to and/or from the distal end of the handpiece assembly 3010 can be used.

Figure 28:
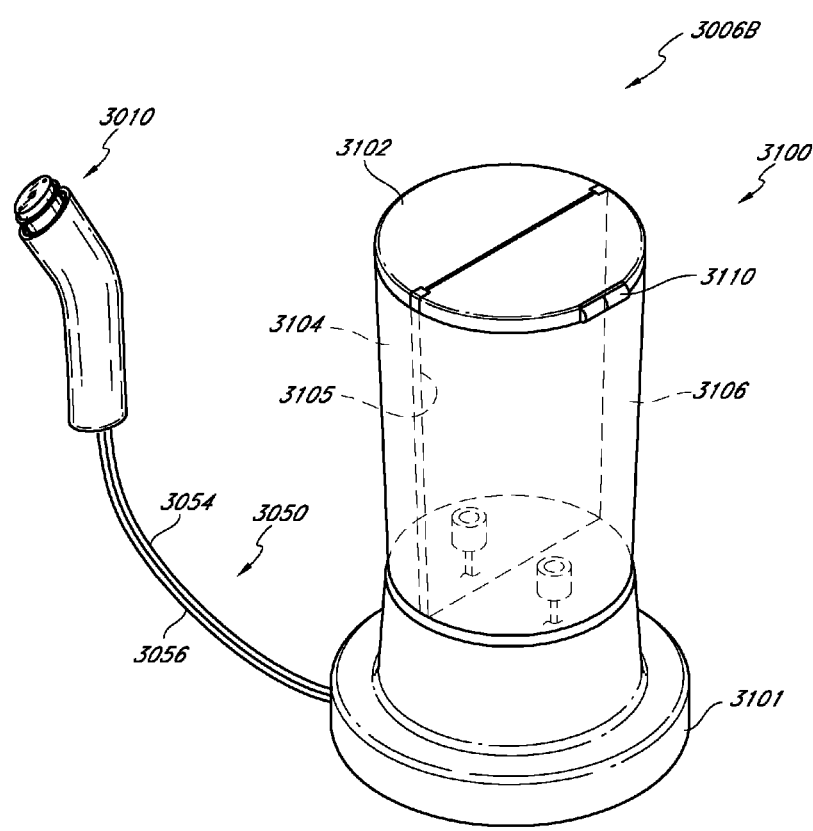
FIG. 28 illustrates a perspective view of a skin treatment system comprising a handpiece assembly and a canister according to one embodiment.

As illustrated in FIG. 28, a handpiece assembly 3010 and a conduit 3050 of a treatment system 3006B can be placed in fluid communication with a canister 3100. The illustrated canister 3100 comprises a base 3101 and one or more compartments 3104, 3106. As discussed, the canister 3100 can include one or more storage compartments 3104 and/or waste compartments 3106 that are separated by a baffle 3105 or other separation member. The various compartments 3104, 3106 can be placed in fluid communication with one or more passages 3054, 3056 of the conduit 3050 to selectively transfer fluids and/or other materials to and/or from a handpiece assembly 3010. In addition, the system 3006B can include a pump or other fluid transfer device (not shown). For example, in one embodiment, a pump is placed within or near the base 3101. In other arrangements, the pump is positioned in one or more other locations (e.g., external to the base 3101).

With continued reference to FIG. 28, the canister 3100 can include a lid 3102 or other cover member that permits a user to selectively access the interior of the compartments 3104, 3106 for filling, emptying, cleaning and/or any other task. In some embodiments, the lid 3102 comprises a hinge 3110 or other device that facilitates accessing the interior of the various compartments 3104, 3106.

Figure 29A:
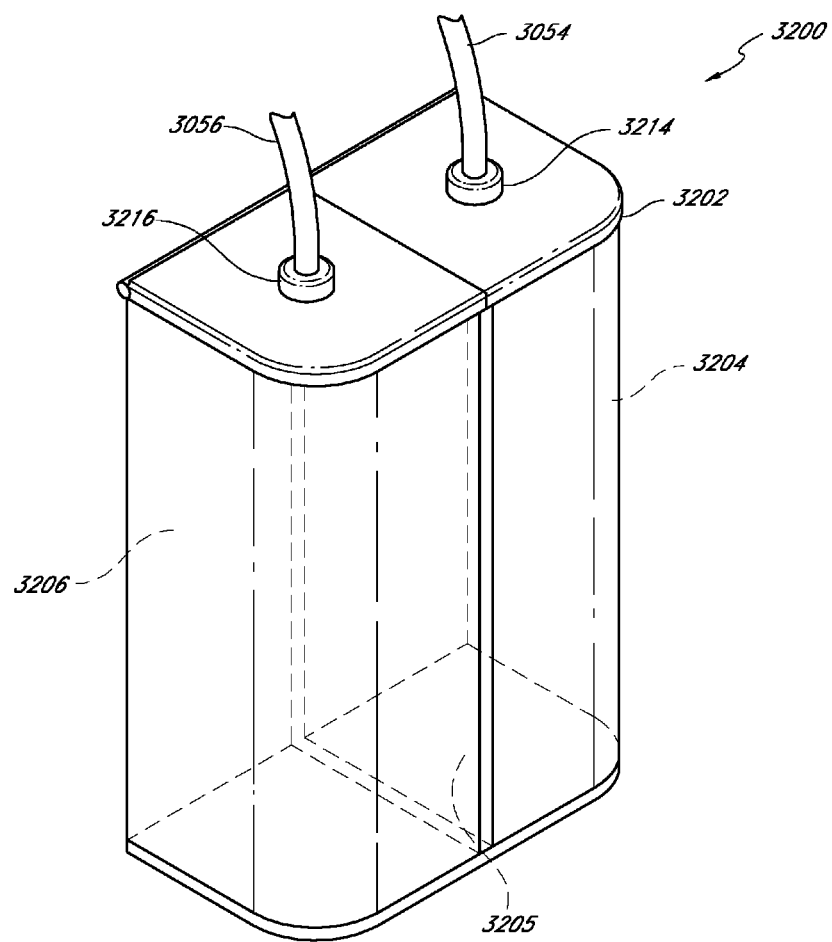
FIG. 29A illustrates a perspective view of a combination storage and waste canister in accordance with another embodiment.

Another embodiment of a canister 3200 is illustrated in FIG. 29A. In the depicted arrangement, the canister 3200 comprises a storage compartment 3204 and a waste compartment 3206. As discussed, however, in other embodiments, the canister 3200 can comprise more or fewer compartments, as desired or required. The compartments 3204, 3206 can be separated by a baffle 3205 or another separation member. In addition, the canister can include a removable lid 3202 that permits a user to access the interior of the compartments 3204, 3206. In FIG. 29A, each compartment 3204, 3206 comprises a fitting 3214, 3216 or similar member to which conduits or passages 3054, 3056 of a conduit (e.g., tubing, pipe, etc.) can attach. Thus, the conduit can be placed in fluid communication with the various compartments 3204, 3206 of the canister 3200. In other embodiments, the fittings 3214, 3216 or ports can be located in one or more other locations of the canister 3200 (e.g., the bottom, side, etc.).

Figure 29B:
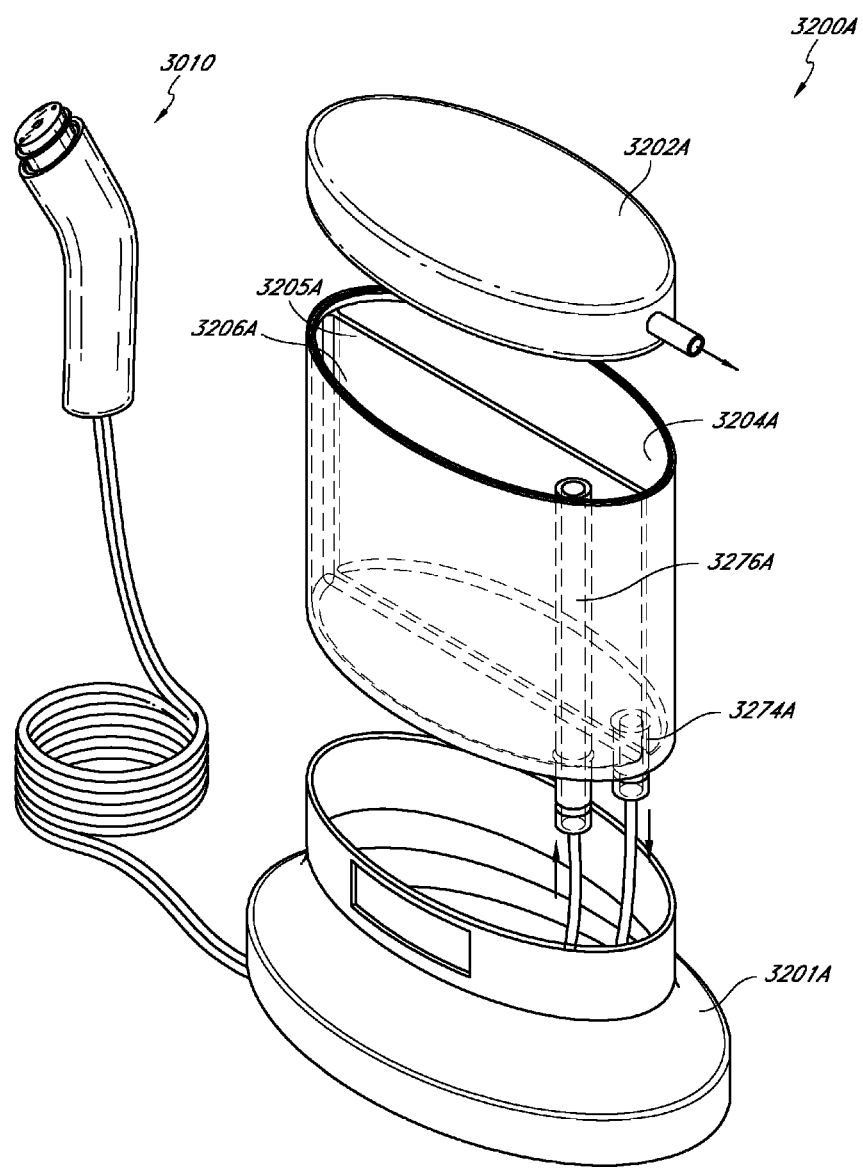
FIG. 29B illustrates a perspective view of a combination storage and waste canister in accordance with yet another embodiment.

A different embodiment of a canister 3200A is illustrated in FIG. 29B. As with other embodiments, the illustrated canister 3200A comprises a supply compartment 3204A and a waste compartment 3206A that are separated by a baffle 3205A or other member. As shown, the canister 3200A can comprise a base 3201A and a lid 3202A or other cover member. In addition, the compartments 3204A, 3206A can comprise one or more internal channels or conduits 3274A, 3276A that facilitate in the transfer of fluids or other materials into and/or out of the canister 3200A. In some embodiments, the canister 3200A is configured to move fluids to and from a handpiece assembly 3010 in a manner similar to what is schematically described in FIG. 27.

FIG. 3030 illustrates a handpiece assembly 3310 according to another embodiment. In the depicted arrangement, the handpiece assembly 3310 comprises a main body portion 3314 and a tip 3320 that is configured to contact and treat the skin. In addition, in the illustrated embodiment, the proximal end 3311 of the assembly 3310 includes a canister 3400. Thus, unlike other arrangements disclosed herein, the depicted canister 3400 is physically attached to and incorporated into the handpiece assembly 3310. In one embodiment, the canister 3400 can be separated and/or attached to the main body portion 3314 of the handpiece assembly 3310 by manipulating a release tab 3401, button or other feature. One or more gaskets, O-rings or other members (not shown) can be positioned between the main body portion 3314 and the canister 3400 in order to reduce the likelihood of leaks.

Accordingly, a user can easily and conveniently handle and manipulate the handpiece assembly 3310 illustrated in FIG. 3030 (or variations thereof) because the canister 3400 and the main body portion 3314 of the assembly 3310 are self contained within a single structure. In some embodiments, the handpiece assembly 3310 includes an internal pump or other fluid transfer device within its main body portion 3314. Alternatively, a fluid transfer device and/or any other component can be positioned outside of the handpiece assembly 3310 and/or at any other location. Such components can be attached to or separate from the handpiece assembly, as desired or required.

Figure 30:
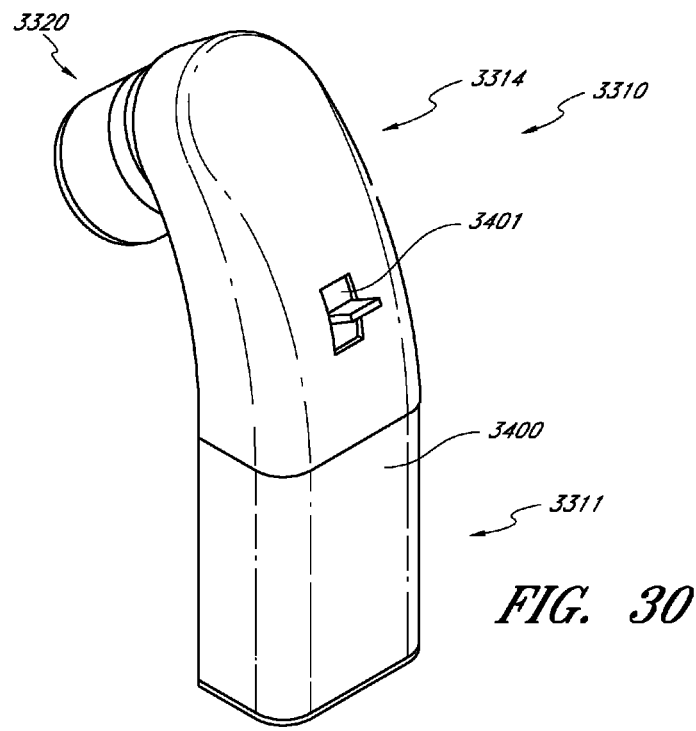
FIG. 30 illustrates a perspective view of another embodiment of a handpiece assembly.
Figure 31:
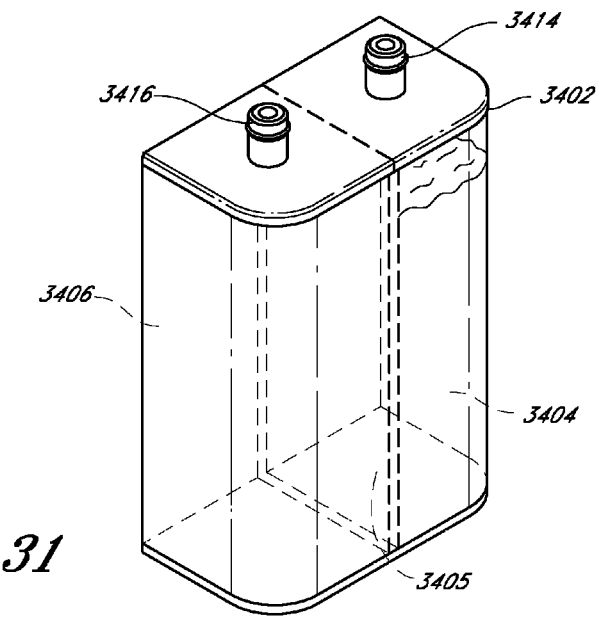
FIG. 31 illustrates a perspective view of an embodiment of a combination storage and waste canister configured to be used with the handpiece assembly of FIG. 30.

FIG. 31 illustrates one embodiment of a canister 3400 configured for use with a self-contained handpiece assembly 3310 such as the one as illustrated in FIG. 30. As shown, the canister 3400 can comprise a delivery compartment 3404 in which one or more treatment fluids or other materials can be placed. In addition, the canister 3400 can comprise a waste compartment 3406 to which fluids, exfoliated skin and/or other substances withdrawn from the treatment surface can be directed. As with other embodiments disclosed herein, the canister 3400 can comprise a baffle 3405 or other separation member. In other embodiments, completely separate canisters can be attached to the proximal end of the handpiece assembly 3310 (e.g., one or more delivery canisters, a waste canister, etc.).

With continued reference to FIG. 31, the canister 3400 can comprise one or more ports 3414, 3416 or other fittings through which fluids or other substances can be transferred (e.g., between the tip 3320 and the canister 3400). According to some embodiments, the canister 3400 is configured to lock to the main body portion 3314 using one or more devices or methods, such as, for example, locking tabs, clasps, magnetic connectors, other fasteners and/or the like.

Any of the embodiments of a handpiece assembly disclosed herein can comprise a tip that swivels, rotates and/or otherwise moves relative to a main body portion. Such a feature can facilitate moving and manipulating a handpiece assembly along a person's skin surface during a treatment procedure. This can be particularly significant when the treatment surface is highly contoured.

Figure 32:
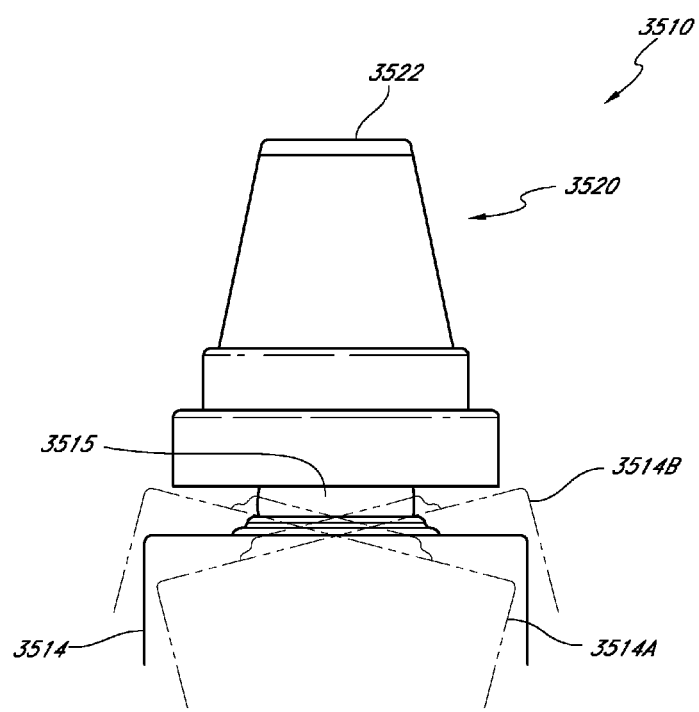
FIG. 32 schematically illustrates one embodiment of the distal end of a handpiece assembly having a tip that is configured to tilt or pivot.

In the embodiment illustrated in FIG. 32, a handpiece assembly 3510 comprises a joint 3515, hinge or other movement mechanism (e.g., ball joint or mechanism, swivel joint or mechanism, etc.). In the illustrated arrangement, the joint 3515 is generally located between the tip 3520 and the main body portion 3514 of the handpiece assembly 3510. As illustrated in phantom, such a joint 3515 or other mechanism can advantageously permit a tip 3520 to be moved relative to the adjacent body portion 3514. For example, in some embodiments, the body portion 3514 can be moved relative to the tip 3520 between a first position 3514A and a second position 3514B. In some embodiments, the passages of a conduit (not shown) are configured to pass through the joint 3514 (e.g., for passages to be in fluid communication from the main body portion 3514 to the tip 3520 through the joint 3515) to permit fluids or other materials to be transferred to and/or from the working surface 3522 of the tip 3520 during the operation of the handpiece assembly 3510.

With respect to any of the embodiments discussed and/or illustrated herein, the handpiece assembly, pump or other fluid transfer device and/or any other component of the skin treatment system can be powered using one or more power sources. For example, in some embodiments, a battery (e.g., disposable, rechargeable, etc.), an AC power source (e.g., with or without a transformer) or any other power device or source can be connected, attached or otherwise supplied to the desired component or subcomponent of the treatment system. In addition, the various components or subcomponents can include one or more controllers, electrical and/or instrumentation connections, ports and/or the like, as desired or required for the proper operation of the treatment system.

According to one embodiment, the self-contained handpiece assembly 3310 illustrated in FIG. 30 is configured to include a rechargeable battery. The handpiece assembly 3310 can be sized, shaped and otherwise configured to be placed in a docking station when not in use. The docking station can be configured to recharge the battery of the assembly 3310. In other embodiments, however, a handpiece assembly can be powered by AC or DC power (e.g., connected to a power cable or the like).

Figure 33:
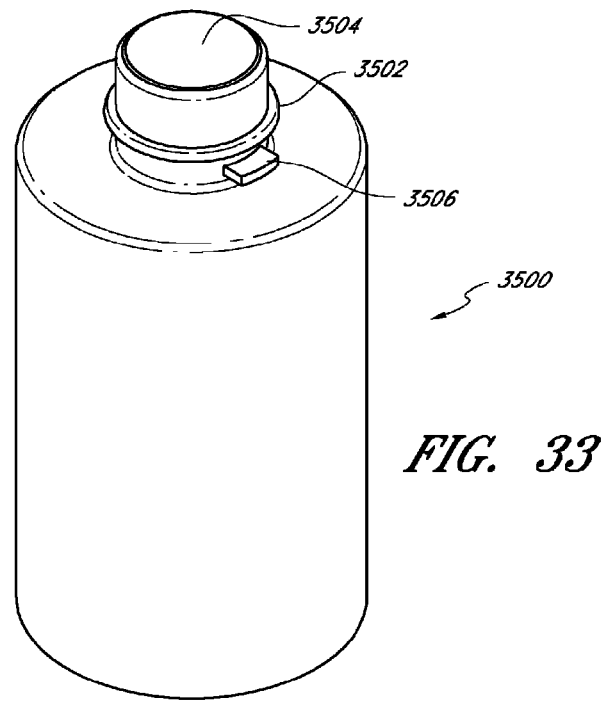
FIG. 33 illustrates a perspective view of a cartridge or other container comprising a treatment fluid or other material according to one embodiment.

FIG. 33 illustrates one embodiment of a cartridge 3500 containing a serum and/or another fluid or material used during a skin treatment procedure. As shown, the cartridge 3500 can comprise a membrane 3504 or other member to seal or substantially seal the internal contents of the cartridge 3500. In addition, the cartridge 3500 can include a locking ear 3506 or other feature or member that is configured to mate with a corresponding portion of the handpiece assembly. In some embodiments, such a locking ear 3506 is sized, shaped and otherwise configured to align with a slot or other opening in a docking area of the handpiece assembly. Once the locking ear 3506 or other feature is properly aligned with and pushed into a corresponding recess or other portion of the handpiece assembly, the cartridge 3500 can be rotated or otherwise moved to secure it to the handpiece assembly. In other arrangements, a cartridge includes two or more locking ears 3506 or other features that are configured to mate with corresponding areas or portions of the handpiece assembly.

With further reference to FIG. 33, the cartridge 3500 can include an O-ring 3502 or other sealing member to help prevent fluids and/or other substances from leaking once the cartridge 3500 is properly inserted within the handpiece assembly. In the illustrated embodiment, the cartridge 3500 comprises a generally cylindrical body with a relatively narrow neck portion. However, it will be appreciated that the shape, size and/or any other details or characteristics of the cartridge 3500 can be different than illustrated and discussed herein to suit a particular application or use.

Figure 34:
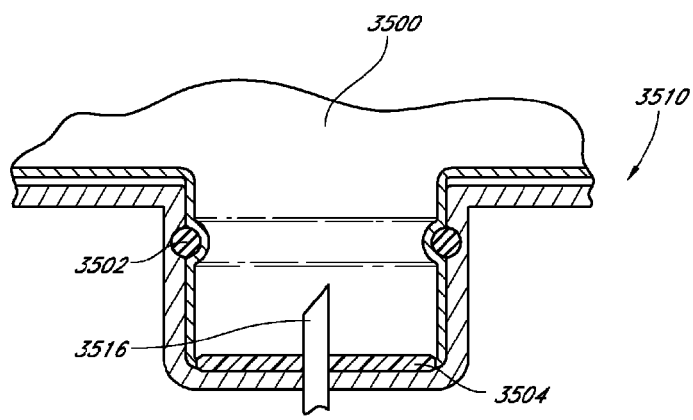
FIG. 34 illustrates a cross-sectional view of a handpiece assembly or other portion of the treatment system configured to receive the cartridge or container of FIG. 33.

FIG. 34 illustrates a cross-sectional view of a docking portion or area 3510 of a handpiece assembly with a cartridge 3500 being secured therein. As illustrated, the docking area 3510 of the handpiece assembly can include a hollow tube 3516 or other puncturing member that is configured to penetrate the membrane 3504 when the cartridge 3500 is securely positioned within the docking area 3510. As discussed, in order to prevent or reduce the likelihood of leaks, the nozzle of the cartridge and/or the docking area 3510 can comprise an O-ring 3502 and/or another sealing member.

According to some embodiments, once the membrane 3504 is punctured, the internal contents of the cartridge 3500 can be in fluid communication with the tip (not shown) of a handpiece assembly. Thus, the hollow tube 3516 or other penetrating member can access the internal contents of the cartridge 3500 so they can be transferred through the body of the handpiece assembly to a working surface (e.g., tip). The fluids and/or other substances can be conveyed to a tip or other working surface of the handpiece assembly by gravity flow, using a pump or other fluid transfer device and/or the like. In some arrangements, as illustrated in FIG. 33, the cartridge 3500 includes a locking member 3506 (e.g., tab) that is configured to mate with a corresponding portion of the docking area 3510 when properly inserted therein.

The membrane 3504 of the cartridge 3500 can include any flexible, semi-rigid or rigid materials that is adapted to be punctured by a hollow tube 3516 or other member when the cartridge 3500 is secured to a handpiece assembly. In some embodiments, the membrane comprises rubber, plastic and/or the like. In addition, the membrane 3504 can be configured to be re-sealable once the cartridge 3500 is removed from the handpiece assembly.

Figure 35:
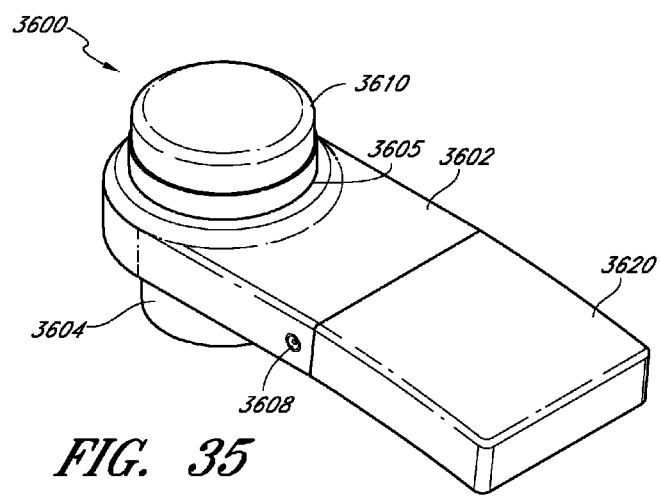
FIG. 35 illustrates a perspective view of a handpiece assembly according to another embodiment.
Figure 36:
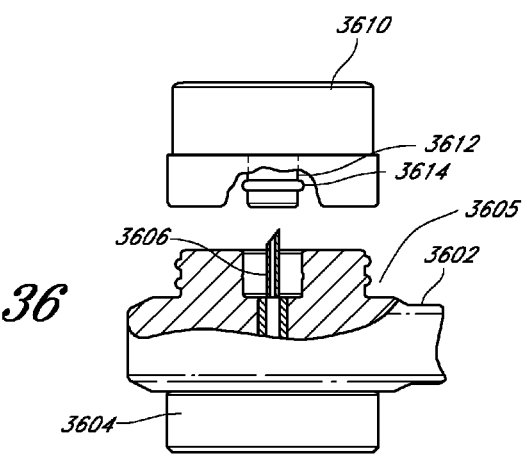
FIG. 36 illustrates a cross-sectional view of a portion of a handpiece assembly configured to receive a cartridge or other container according to one embodiment.
Figure 37:
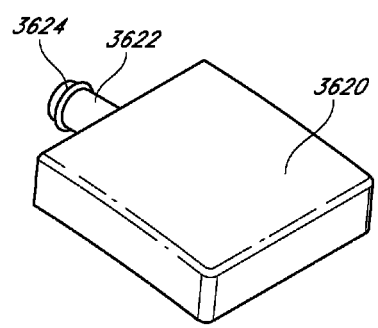
FIG. 37 illustrates a perspective view of waste cartridge or container configured for use with a skin treatment system according to one embodiment.

FIGS. 35-37 illustrate another embodiment of a handpiece assembly 3600 adapted to treat the skin. The depicted assembly 3600 comprises a main body portion 3602, a working tip 3604 and a docking area or port 3605 in which a cartridge 3610 and a waste canister 3620 can be inserted. Such a handpiece assembly 3600, as with other embodiments disclosed herein, can be an all-inclusive assembly that eliminates or reduces the need for other separate components. For example, the main body portion 3602 can comprise a vacuum pump or other fluid transfer device (not shown) to help deliver fluids and other treatment materials to the working tip 3604 and remove waste fluids, exfoliated skin and/or other materials to the waste canister 3620.

With reference to FIG. 36, the handpiece assembly 3600 can include a docking port or area 3605 that is configured to receive a cartridge 3610. The cartridge can include one or more treatment fluids, substances or the like. In some embodiments, as discussed herein with respect to the embodiment illustrated in FIG. 33, the cartridge 3610 comprises a membrane (not shown in FIG. 36) that is configured to substantially seal the internal contents of the cartridge 3610. The docking area 3605 can include a puncturing member 3606 (e.g., hollow tube, syringe, needle, etc.) that is sized, shaped, positioned and otherwise configured to break the membrane or seal so that the contents of the cartridge 3610 can be placed in fluid communication with the main body portion 3602 and the tip 3604 of the handpiece assembly 3600. The cartridge 3610 and docking area 3605 can include one or more mating features (e.g., threads, locking tabs, snap connections, other mechanical fasteners, etc.) to ensure that the cartridge 3610 is secured to the handpiece assembly 3600 during use.

As illustrated in the cutaway cross-sectional view of FIG. 36, the docking area 3605 can be shaped, sized and otherwise configured to receive a nozzle 3612 or other protruding member of the cartridge 3610. Accordingly, the hollow tube 3606 or other puncturing member of the main body portion 3602 can penetrate a membrane or other sealing member disposed along the end of the nozzle 3612 once the cartridge 3610 is secured within the docking area 3605. In order to prevent or reduce the likelihood of leaks of fluids and/or other substances contained within the cartridge 3610, the nozzle 3612 can comprise one or more O-rings 3614 or other sealing members.

The handpiece assembly 3600 illustrated in FIGS. 35-37 includes a generally rectangular shape. However, in other embodiments, the shape, size and/or other characteristics or properties of the handpiece assembly 3600 can vary, as desired or required by a particular application or use.

FIG. 37 illustrates one embodiment of a waste canister 3620 that is configured to attach to a proximal end of the handpiece assembly 3600. The waste canister 3620 can be configured to collect exfoliated skin, used serums and other fluids and/or the like that are drawn away from a person's skin during treatment. As shown, the waste canister 3620 can comprise a port 3622 that is adapted to engage and secure to one or more receiving areas of the main body portion 3602 of the handpiece assembly 3600. As with the cartridge 3610, the waste canister 3620 can include one or more mating features with the adjacent portion of the handpiece assembly 3600. Further, one or more O-rings 3622 or other sealing members can be used to prevent or reduce the likelihood of leaks between the waste canister 3620 and the main body portion 3602 of the handpiece assembly 3600.

With continued reference to FIG. 35, the handpiece assembly can include a port 3608 or other connection for a power source or other electrical connection. In some embodiments, the port 3608 is configured to receive an AC adapter or transformer (e.g., 12 volt charger). In other embodiments, the handpiece assembly 3600 comprises a rechargeable battery or other power source (not shown) which may be recharged via the port 3608.

Figure 38:
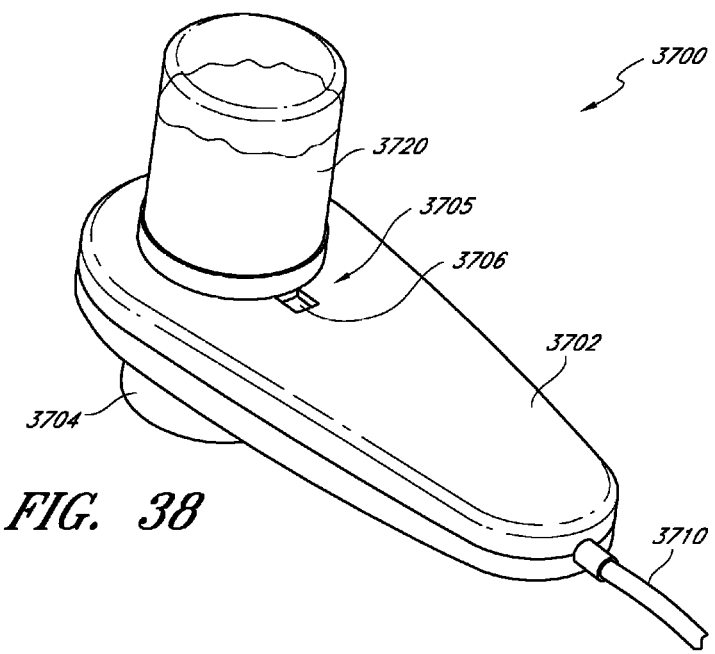
FIG. 38 illustrates a perspective view of a handpiece assembly according to one embodiment.
Figure 39:
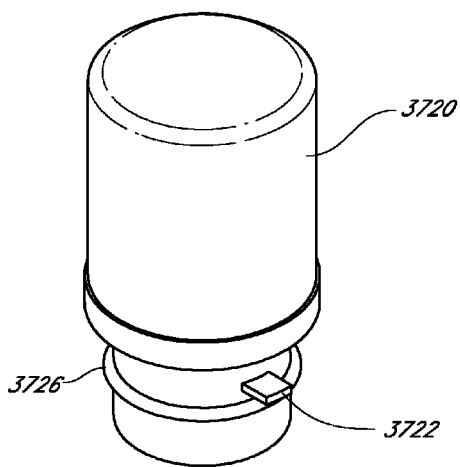
FIG. 39 illustrates a cartridge or other container configured for placement within a corresponding area of the handpiece assembly of FIG. 38.
Figure 40:
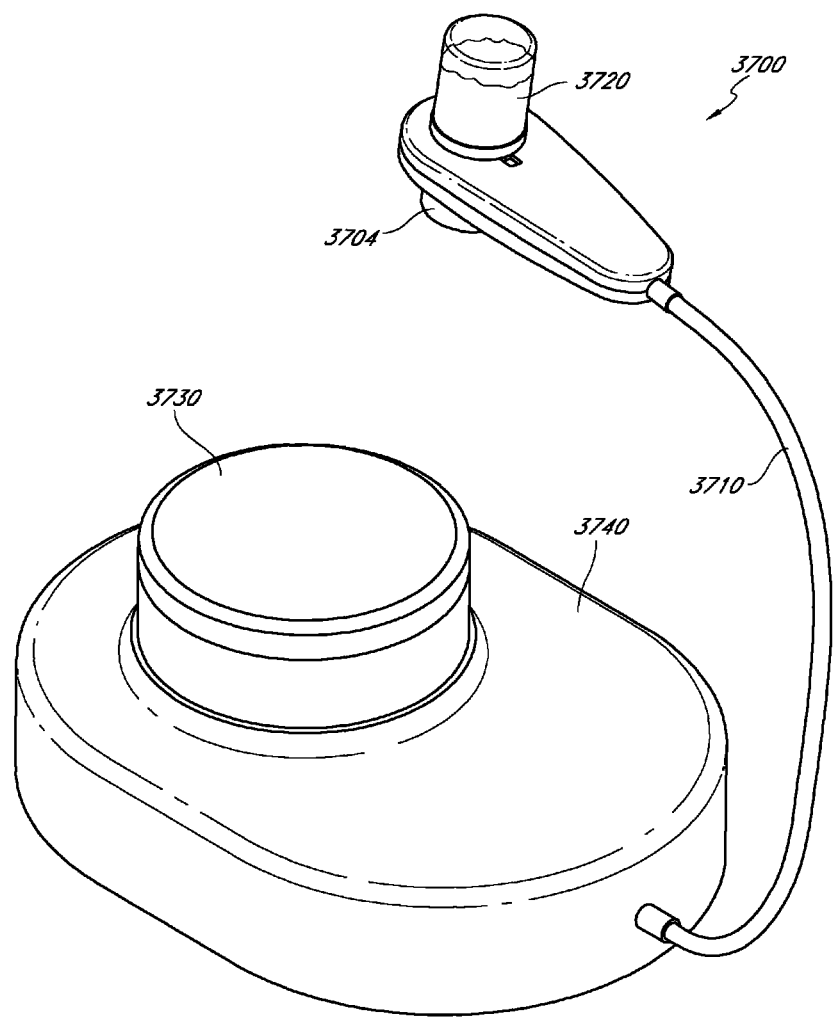
FIG. 40 illustrates a handpiece assembly in fluid communication with a fluid transfer system and a waste canister according to one embodiment.

FIGS. 38-40 illustrate another embodiment of a handpiece assembly 3700 that comprises, among other things, a main body portion 3702, a working tip 3704 and a docking area 3705 for receiving a cartridge 3720. As shown in FIG. 39, the cartridge 3720 can comprise a locking ear 3722 or other protruding member that is sized, shaped and otherwise configured to help mate and secure the cartridge 3720 to the docking area 3705. For example, the docking area 3705 can include a recess 3706 (e.g., turn lock feature) that is adapted to receive the locking ear 3722 or other member of the cartridge 3720. Once the cartridge 3720 is aligned with and inserted into the recess 3706, it can be rotated or otherwise moved to temporarily secure the cartridge 3720 to the main body portion 3702 of the assembly 3700.

When the contents of the cartridge 3720 have been emptied and/or when a user wishes to use fluids and/or materials contained with a different cartridge 3720, the process by which the cartridge 3720 was secured within the docking area 3705 can be reversed. For example, the cartridge 3720 can be rotated so that the locking ear 3722 or other protruding member generally aligns with the recess 3706 to permit the cartridge 3720 to be removed. As with other embodiments, the illustrated cartridge 3720 can include an O-ring 3726 or other sealing member to prevent or reduce the likelihood of leaks.

With continued reference to FIGS. 38-40, for aesthetic, ease of handling and/or any other reason, the handpiece assembly 3700 can include a tapered shape. As with any other embodiments disclosed herein, or variations thereof, the handpiece assembly 3700 can be designed with finger grips or other features that facilitate a user to grip and manipulate the handpiece assembly 3700 during use. In addition, the outer surface of any of the embodiments of the handpiece assemblies discussed and/or illustrated herein (or variations thereof) can comprise one or more durable materials that are configured to withstand the elements to which they may be exposed. In some embodiments, the exposed surfaces of a handpiece assembly comprise plastics, metals (e.g., stainless steel) and/or the like.

With continued reference to FIG. 40, the handpiece assembly 3700 can be placed in fluid communication with a housing 3740 and a waste canister 3730 via one or more conduits 3710. As shown, the housing 3740 can receive a removable waste canister 3730 along its upper surface. Alternatively, the housing 3740 can be adapted to receive one or more waste canisters 3730 at any other portion or location. In some embodiments, the canister 3730 can be advantageously removed from the housing 3740 for emptying, cleaning and/or any other purpose. As with other embodiments disclosed herein, the housing 3740 can comprise an internal and/or external pump or other fluid transfer device. Such a fluid transfer device can be used to remove waste fluids and/or other materials away from the tip 3704 of the handpiece assembly 3700 (e.g., via a waste conduit 3710), and in some arrangements, simultaneously draw treatment serums and other fluids from the canister 3720 toward the tip 3704 of the handpiece assembly 3700.

The pump, other fluid transfer device and/or any other electric component or features of the system can be operated by one or more power sources (e.g., AC, DC, rechargeable or disposable batteries, etc.). In addition, the handpiece assembly 3700 and/or the housing 3740 can include buttons, dials and/or other members that permit a user to selectively control the operation during a treatment procedure.

Figure 41A:
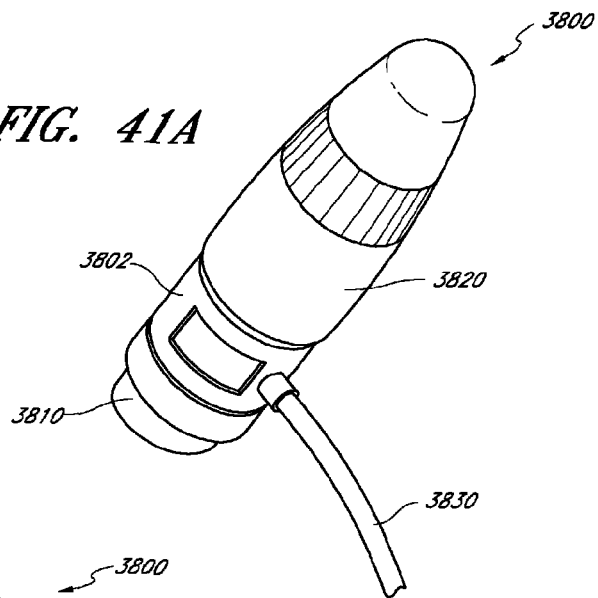
FIGS. 41A and 41B illustrate an embodiment of a handpiece assembly.
Figure 41B:
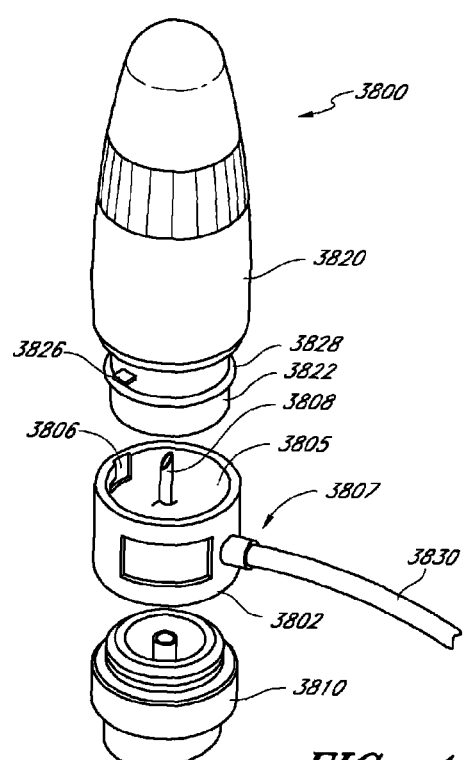

FIGS. 41A and 41B illustrate another embodiment of a handpiece assembly 3800 configured for use in a skin treatment system. Like in other embodiments disclosed herein, the depicted handpiece assembly 3800 comprises a main body portion 3802, a removable tip 3810 and a receiving or docking area 3805 for securely receiving a cartridge 3820. As shown, the main body portion 3802 of the handpiece assembly 3800 can comprise a port 3807 to which a conduit 3830 or other channeling member may connect. According to some embodiments, the conduit 3830 is placed in fluid communication with a vacuum pump or other fluid transfer device (not shown) for removing waste materials away from the treatment surface (e.g., tip 3810).

Figure 42:
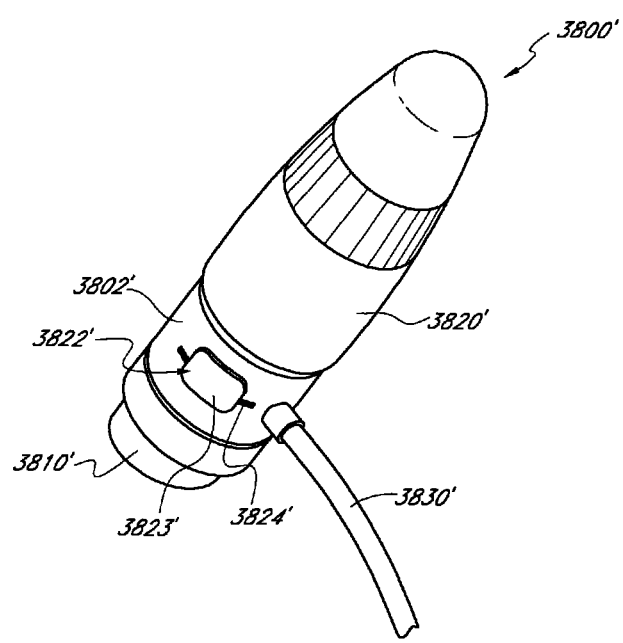
FIG. 42 illustrates another embodiment of a handpiece assembly.

As noted above, a handpiece assembly can comprise one or more valves 3822 or other flow control members or features to regulate the delivery of fluids and/or other materials toward the tip. One embodiment of a handpiece assembly 3800' having such a valve 3822' is illustrated in FIG. 42. The inclusion of such a valve or other flow control device or feature can permit a user to adjust the delivery of serums and/or other fluids or materials toward the tip 3810' by operating a handle or tab 3823' of the valve. As shown in FIG. 42, the handle or tab 3823' can be configured to rotate or otherwise move within a corresponding slot 3824' of the handpiece housing. In some embodiments, the handle or tab 3823' is resiliently biased (e.g., in the fully open position, in the fully closed position, an intermediate position, etc.), as desired or required. According to some arrangements, the valve comprises a needle valve or other valve assembly that is positioned within the main body portion 3802'. Such a needle valve with an external handle or controller can be incorporated into any of the embodiments disclosed herein. The delivery of fluids and/or other materials from the cartridge 3820' to the tip 3810' can be controlled using one or more other types of valves or features. For example, in one embodiment, the flow of fluids and/or materials toward the tip can be regulated by rotating the cartridge 3820' relative to the main body portion 3802'. Thus, in such arrangements, flow control can be established in a similar way as described herein with reference to, inter alia, the embodiment illustrated in FIGS. 1-4B.

As discussed herein in reference to other arrangements, the cartridge 3820 can include a nozzle portion with a locking ear 3826 or other protruding member that is configured to engage and mate with a corresponding slot 3806, recess and/or other feature of the docking area 3805. Further, the nozzle of the cartridge 3820 can include an O-ring 3828 or other sealing member to prevent or reduce the likelihood of leaks when fluids and/or other substances are being transferred from the cartridge 3820 to the tip 3810. In some embodiments, the end of the nozzle portion of the cartridge comprises a membrane or other member (not shown) that can be punctured or otherwise compromised by a hollow tube 3808, spike or other member when the cartridge 3820 is secured within the docking area 3805.

Figure 43A:
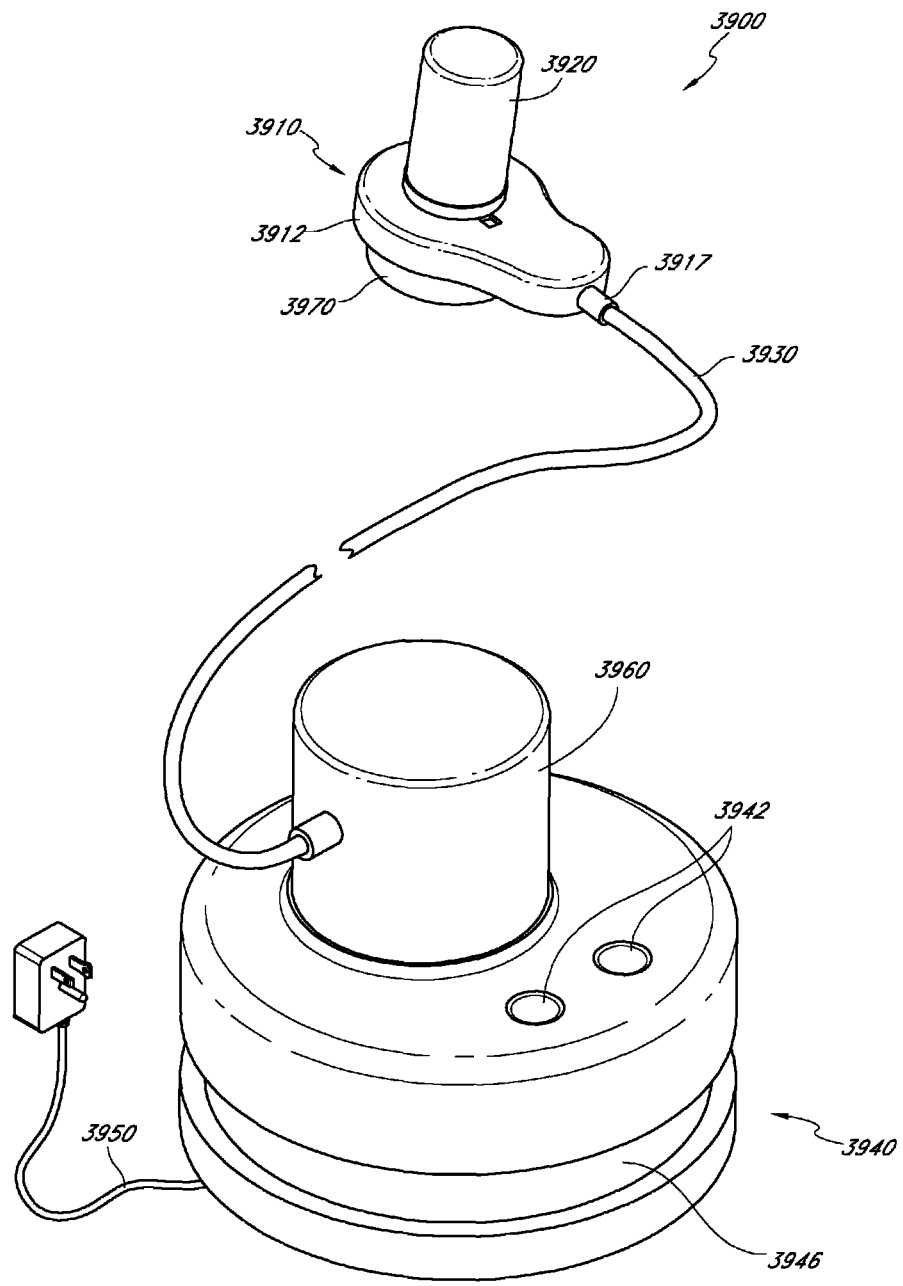
FIG. 43A illustrates a perspective view of a handpiece assembly in fluid communication with a waste canister in accordance with one embodiment.

Another embodiment of a skin treatment system 3900 comprising a handpiece assembly 3910, a replaceable cartridge 3920 and a separate base member 3940 is illustrated in FIG. 43A. As shown, the handpiece assembly 3910 can comprise a main body portion 3912 to which a cartridge 3920 and a removable tip 3970 can be secured. In addition, the handpiece assembly 3910 can include a port 3917 that is used to place the handpiece assembly 3910 in fluid communication with the base member 3940 via one or more conduits 3930. As with other embodiments disclosed herein, the cartridge 3920 can be selectively secured to and/or removed from the main body portion 3912 of the handpiece assembly. Thus, the cartridge 3920 can include one or more locking ears, O-rings and/or the like.

In addition, the base member 3940 can include a waste canister or container 3960 that is adapted to receive waste fluids and other substances. As with the cartridge 3920, the waste canister 3960 can be configured to be selectively secured to and/or removed from the base member 3940 for emptying, cleaning, replacement and/or any other purpose.

Further, in some embodiments, the base member 3940 comprises one or more controls (e.g., ON-OFF switches, other switches, knobs and/or the like) for regulating the operation of the system. As shown, a power supply or other electrical connection 3950 can be used to power the base member 3940, a vacuum pump or other fluid transfer device contained within the base member 3940 (or any other portion of the system) and/or any other electrical component or subcomponent of the system. Further, the base member 3940 can comprise a recessed area 3946 along its lower portion which is configured to receive one or more conduits 3930, power cables and/or the like.

Figure 43B:
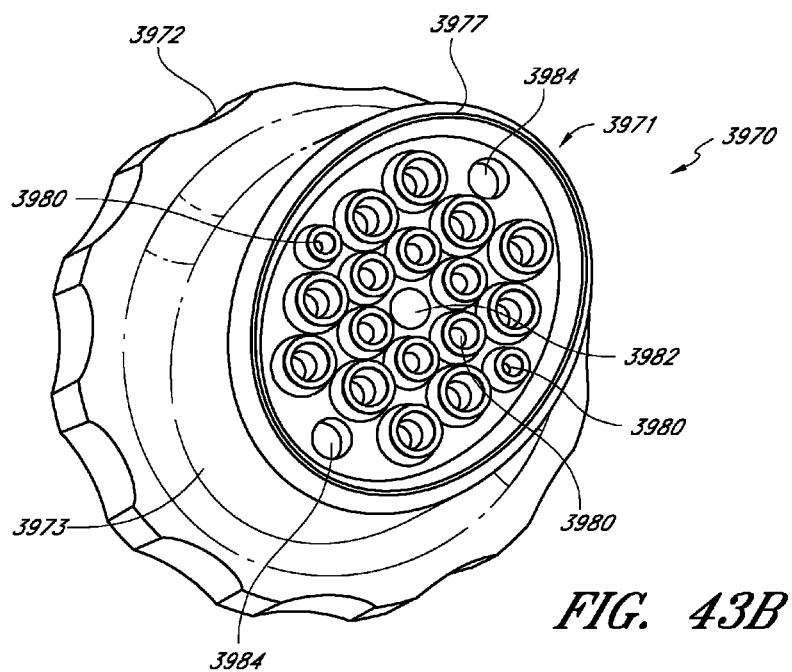
FIG. 43B illustrates a top perspective view of one embodiment of a removable tip adapted for placement on a handpiece assembly.
Figure 43C:
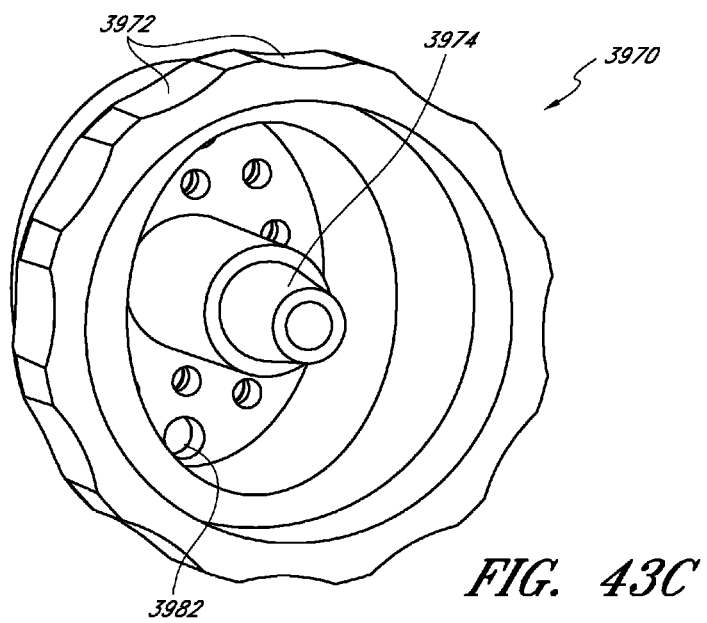
FIG. 43C illustrates a bottom perspective view of the removable tip of FIG. 43B.

FIGS. 43B and 43C illustrate different views of one embodiment of a removable tip 3970 configured for placement on a handpiece assembly as disclosed herein. As shown, the tip 3970 can include a tip body portion 3973 and a tip skirt portion 3972 extending along the bottom of the tip body portion 3973. The skirt portion 3972 can include a plurality of gripping members or other features (e.g., recesses, protrusions, etc.) to facilitate the handling of the tip 3970.

A tip can be configured to slidably connect to the distal end and/or any other portion of a handpiece assembly. For example, in some embodiments, the tip can be press fit onto the handpiece assembly. One or more O-rings or other sealing members can be used between adjacent surfaces of the tip and the handpiece assembly to prevent or reduce the likelihood of undesirable leaks. In other embodiments, a tip can be secured to a handpiece assembly using any other method or device, such as, for example, a threaded connection, interlocking tabs, flanges or other members, other fasteners and/or the like. In still other arrangements, the tip can be permanently or semi-permanently attached to the handpiece assembly.

In the embodiment illustrated in FIGS. 43B and 43C, the tip 3970 comprises one or more surfaces, elements and/or features along its distal end 3971 that are configured to treat (e.g., exfoliate) skin. Such tips can include one or more treatment elements, either in addition to or in lieu of abrasive elements. As used herein, "abrasive element" is a broad term and includes, without limitation, protruding elements, abrasive materials (e.g., grit, sandpaper-like material, other coarse materials, etc.), roughened surfaces, contoured surfaces, surfaces with openings, recesses or other features, brushes, blades, surfaces impregnated with diamonds or other materials and/or the like. Further, as used herein, "treatment element" is a broad term and includes, without limitation, an abrasive element, massage elements or features, elements or features configured to moisturize or apply one or more treatment agents or fluids, polishing or soothing elements or features and/or the like. As discussed, any embodiments of a tip for a handpiece assembly can comprise one or more treatment elements and/or abrasive elements, as desired or required by a particular application.

As illustrated in FIGS. 43A and 43B, the tip 3970 can include a lip 3977 or other ridge member along its outer periphery. The lip member 3977 can generally define the periphery of the distal end 3971 of the tip 3970. In some embodiments, when the tip 3970 is positioned against the skin, the lip member 3977 inhibits or substantially inhibits fluids or other materials from escaping a space generally defined between the tip 3970 and the adjacent skin surface.

With continued reference to FIGS. 43B and 43C, the tip 3970 can include a plurality of protruding members 3980 positioned along its distal end 3971 and within the interior of the lip member 3977. The protruding members 3980 can be posts or other cylindrically-shaped objects. In some embodiments, the protruding members 3980 comprise relatively sharp edges, which can be configured to remove skin. The protruding members 3980 can have relatively sharp planing blades. The plurality of protruding members 3980 can ablate or roughen a plurality of smaller sections of the skin being treated.

As illustrated, the outer diameter or other comparable dimension (e.g., length, width, etc.) of the posts or other protruding members 3980 can vary. In other arrangements, the diameter and/or other dimensions of the protruding members can be similar or substantiality similar. The posts or other protruding members 3980 can be located, spaced and otherwise oriented along the distal end 3971 of the tip 3970 in any desired or required manner.

It will be appreciated that the size, shape, spacing, orientation, location and/or other properties of the protruding members 3980 can be different than illustrated and disclosed herein, as desired or required by a particular procedure or application. As discussed herein, the lip member 3977 of the tip 3970 can help create an enclosed space generally defined between the distal end 3971 of the tip 3970 and the skin surface being treated. Therefore, according to some embodiments, the lip member 3977 extends above the top of the protruding members 3980 so that the protruding members are within the enclosed space during a treatment procedure.

In other embodiments, the top surface of the lip 3977 is generally aligned with the top surface of or below the protruding members 3980.

With reference to FIGS. 43B and 43C, the tip 3970 can include an interior delivery stem 3974 that is configured to place the distal end 3971 of the tip 3970 in fluid communication with the one or more delivery channels or other conduits located within the handpiece assembly. For example, the delivery stem 3974 can be sized, shaped and otherwise adapted to receive fluids and/or other materials from an internal delivery channel of the handpiece assembly.

As illustrated in FIGS. 43B and 43C, the distal end 3971 of the tip 3970 can include an opening 3982 through which fluids and/or other materials conveyed by the delivery stem 3974 may exit. As shown, the opening 3982 can be located at or near the center of the distal end 3971 of the tip 3970. In other arrangements, a tip 3970 can include additional stems 3974 and/or openings 3982. In addition, the size, shape, location and/or other details of the openings 3982 can be different than illustrated herein.

Moreover, the distal end 3971 of the tip 3970 can include one or more outlet openings 3984 through which exfoliated skin, spent serums, other waste liquids, fluids and other materials and/or the like can be removed. In the embodiment illustrated in FIGS. 43B and 43C, the tip 3970 includes two outlet openings 3984. However, more or fewer openings can be included, as desired or required. In addition, some or all of the posts or other protruding members 3980 can be generally hollow so that they perform a similar function as other outlet openings 3984 of the tip 3970. In other embodiments, however, some or all of the protruding members 3980 are not hollow or do not include openings therethrough.

In some embodiments, once the distal end 3971 of a tip 3970 is positioned against the skin being treated, an enclosed space can be created between the skin surface and tip, generally along the interior of a peripheral lip member or other ridge. Therefore, as a vacuum or another suction source is generated in the handpiece assembly, exfoliated skin, spent serum, other fluids and/or other materials can be removed away from the tip 3970. At the same time, the delivery stem 3974 of the tip 3970 and any other conduit or space that is in fluid communication with it may also be subjected to a suction force. Consequently, serums, other fluids and/or other treatment materials can be advantageously transported to the distal end 3971 of the tip 3970 through one or more openings 3982. As discussed, the tip 3970 or variations thereof can comprise any combination of treatment elements and/or abrasive elements, as desired or required by a particular application.

Additional details regarding tips for any embodiments of a handpiece assembly disclosed herein can be found in U.S. patent application Ser. No. 11/392,348 (filed on Mar. 29, 2006 and published as U.S. Publication No. 32007/0156124) and U.S. Provisional Patent Application No. 61/024,504 (filed on Jan. 29, 2008), the entireties of both of which are hereby incorporated by reference herein.

Figure 44:
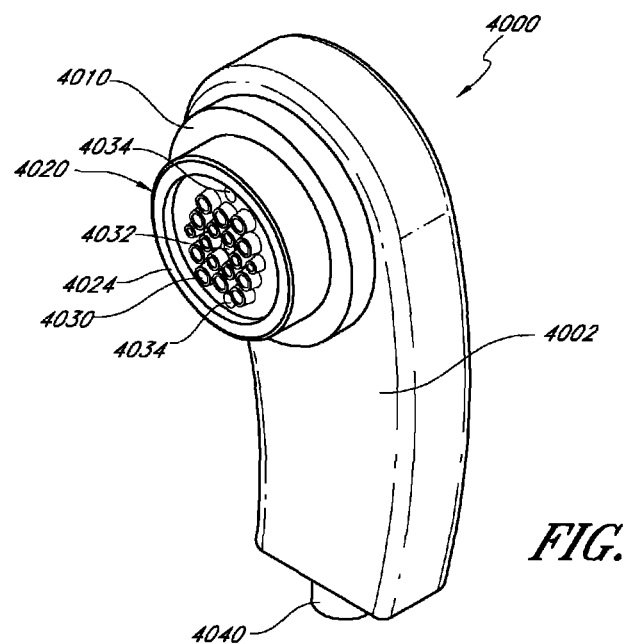
FIG. 44 illustrates a perspective view of another embodiment of a handpiece assembly.

FIG. 44 illustrates another embodiment of a handpiece assembly 4000. In some arrangements, the illustrated assembly 4000 may be particularly well-suited to be used as a shower model. For example, the tip 4020 of the handpiece assembly 4000 can include a dried serum or other material that is configured to dissolve when coming in contact with water and/or other fluids. Thus, once in contact with water, the tip 4020 can be operated to remove skin. For instance, water from a shower head can be used to dissolve the media situated on the tip 4020 of the handpiece assembly 4000. In some embodiments, the handpiece assembly 4000 comprises an internal vacuum pump or other fluid transfer device (not shown) that is used to draw waste liquid and/or materials away from the tip 4010 toward one or more drains 4040. Such drains 4040 may or may not be connected to a separate conduit or other collection device, as required or desired by a particular application.

With continued reference to FIG. 44, the handpiece assembly 4000 can comprise a main body portion 4002 that a user can grasp and manipulate during use. In addition, the tip 4020 can be adapted to be removably positioned onto a raised mounting portion 4010 of the handpiece assembly. In other embodiments, however, the tip 4020 attached directly to the main body portion 4002 of the assembly 4000.

As discussed herein with reference to FIGS. 43B and 43C, the tip 4020 can comprise an outer lip 4024 or other ridge member along its outer periphery. The lip member 4024 can generally define the periphery of the distal end of the tip 4020. In some embodiments, when the tip 4020 is positioned against skin, the lip member 4024 inhibits or substantially inhibits fluids or other materials from escaping a space generally defined between the tip 4020 and the adjacent skin surface. Further, the tip 4020 can include a plurality of protruding members 4030 positioned along its distal end and within the interior of the lip member 4024. As discussed, the protruding members 4030 can be posts or other cylindrically-shaped objects. In some embodiments, the protruding members 4030 comprise relatively sharp edges, which can be configured to remove skin. The protruding members 4030 can have relatively sharp planing blades. Further, the tip 4020 can include one or more openings 4032, 4034 through which treatment fluids, exfoliated skin, other waste materials and/or other substances may enter or exit the working surface of the tip 4020. The size, shape, quantity, location, spacing and/or other details of the openings 4032, 4034 can vary, as desired or required by a particular application or use.

In any of the embodiments disclosed herein, including the one illustrated in FIG. 44, the tip of the handpiece assembly can be configured to rotate, pivot, tilt and/or otherwise move, as desired or required by a particular application.

Figure 45:
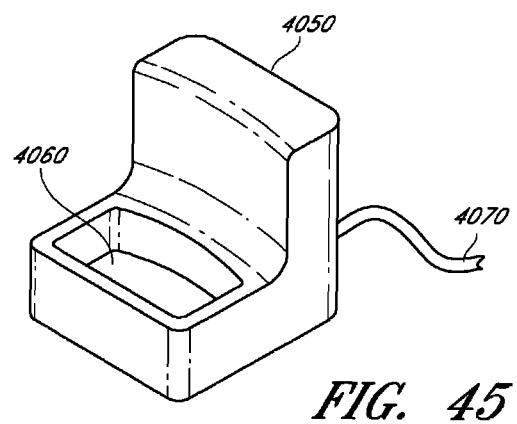
FIG. 45 illustrates a perspective view of a base charging member configured to receive a handpiece assembly according to one embodiment.

FIG. 45 illustrates a charger or docking station 4050 which can be sized, shaped and configured to receive a handpiece assembly. It will be appreciated that any other embodiments of a handpiece assembly disclosed herein can be configured to be placed and stored in such a docking station 4050. The station 4050 can include a cavity or other receiving area in which one or more portions of a handpiece assembly may be selectively inserted and removed. The station 4050 can be attached to a power cord 4070 or other power source so that a rechargeable battery located within the handpiece assembly can be charged.

Figure 46:
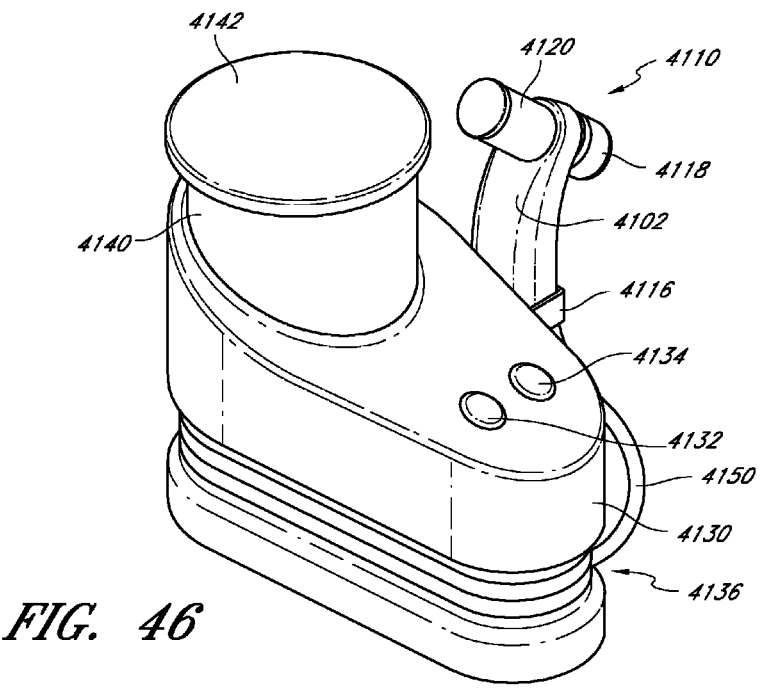
FIG. 46 illustrates a perspective view of a skin treatment system comprising a handpiece assembly and a base member having a waste canister according to one embodiment.
Figure 47:
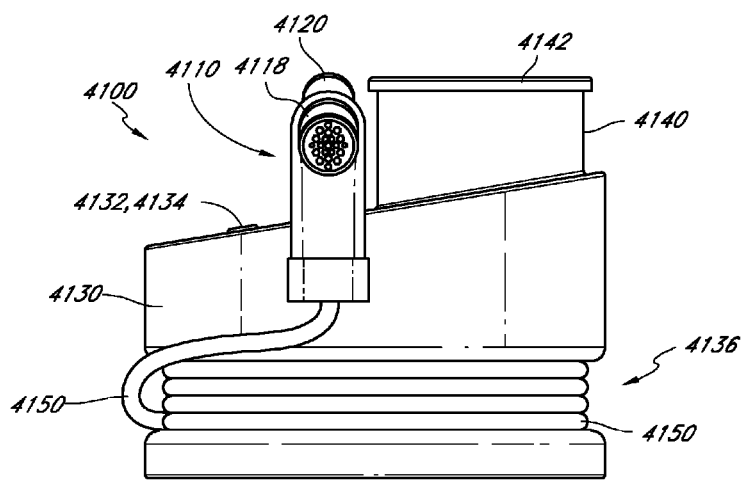
FIG. 47 illustrates a side elevation view of the system of FIG. 46.

Another embodiment of a skin treatment system 4100 comprising a handpiece assembly 4110, a base member 4130 and a waste cartridge 4140 is illustrated in FIGS. 46 and 47. As with other embodiments disclosed herein, the handpiece assembly 4110 can comprise a docking area in which a cartridge 4120 can be selectively removed or attached. In some arrangements, the handpiece assembly 4110 can be secured to a base member 4130 using one or more clips 4116, holders or other members. The handpiece assembly 4110 can be placed in fluid communication with a waste canister 4140 using one or more conduits 4150.

With continued reference to FIGS. 46 and 47, the waste canister 4140 can be configured to be selectively attached to and/or removed from the base member 4130 for emptying, cleaning and/or any other purpose. In some embodiments, the waste canister 4140 comprises a lid 4142 or other cover member. As with any other embodiments disclosed herein, the base member 4130 and/or the handpiece assembly 4110 can comprise one or more buttons 4132, 4134, dials and/or other control members to regulate the operation of the skin treatment system. In addition, the base member can include a recessed region 4136 can enables one or more fluid conduits 4150, power cables or other members to be conveniently coiled therearound. Further, the handpiece assembly 4110 can comprise a main body portion 31101 and a tip 4118 permanently or removably secured thereto.

According to another embodiment, a handpiece assembly can be configured to be used in a shower or in other wet or high moisture conditions. Thus, in some arrangements, the handpiece assembly is waterproof and/or water resistant. In such embodiments, the pump or other fluid transfer device can be driven by electrical power, by water pressure (e.g., one or more connections to running water), by pneumatic power and/or any other method or device. It will be appreciated that such alternative methods or devices of operating a pump or other fluid transfer device can be used with respect to any other embodiment disclosed herein.

FIGS. 48 and 49 illustrate another embodiment of a skin treatment device 4210 configured to be removably secured to a user's fingers during use. As shown, the device 4210 includes a main body portion 4220 having a distal end 4230. A removable tip 4250 can be selectively positioned along the distal end 4230 of the main body portion 4220. In some embodiments, the distal end 4230 of the main body portion 4220 includes one or more supply ports 4234 that are configured to selectively deliver treatment fluids and/or other materials to the skin surface being treated. The supply port 4234 can protrude away from the distal end 4230 of the main body portion 4220. According to some embodiments, the supply port 4234 comprises a cylindrical tube or other type of extension member. Regardless of its exact shape, size, position along the device 4210 and/or other characteristics, the supply port 4234 can be configured to mate with a corresponding portion of the removable tip 4250. In order to prevent undesirable leaks when fluids and/or other materials are being supplied to the tip 4250, one or more O-rings 4232 and/or other sealing members can be positioned near the interface of the main body portion 4220 and the tip 4250 (e.g., along the outside of the protruding supply port 4234, as illustrated in FIG. 48).

Further, the distal end 4230 of the main body portion 4220 can include one or more waste or vacuum ports 4236 that are configured to receive spent serums, other fluids, exfoliated skin and/or any other materials located along the tip-skin interface during use. As shown in FIG. 48, tubing 4260 can be used to place the supply port 4234 and/or the waste ports 4236 in fluid communication with a separate base member (e.g., waste canisters, fluid supply containers, etc.), as discussed herein with reference to FIGS. 24-47. In some embodiments, the tubing 4260 can be molded with two or more lumens 4262, 4264, each of which being configured to receive either waste materials or treatment supply materials. In other embodiments, a treatment supply container and/or a waste canister can be directly or indirectly secured to the device 4210, as desired or required.

The removable tip 4250 can have any size, shape and/or configuration, as desired or required by a particular application or use. For example, the tip 4250 can comprise a plurality of diamonds that are configured to abrade skin when the device 4210 is moved along a skin surface. Alternatively, the tip 4250 can include a plurality of posts, such as, for example, those illustrated in FIGS. 43B, 43C and 3044 herein or alternatives thereto. In other embodiments, the device 4210 is configured to receive a tip 4250 having a spiral abrading design, a generally abrasive surface (e.g., a gritty pad, sandpaper surface, etc.) and/or any other surface configured to abrade skin. Additional information regarding the various types of tips 4250 that can be selectively positioned onto and removed from the device 4210 are provided in U.S. patent application Ser. No. 12/362,353, filed Jan. 29, 2009 and published as on Jul. 30, 2009 as U.S. Patent Publication No. 2009/0192442, and U.S. patent application Ser. No. 11/392,348, filed on Mar. 29, 2006 and published on Jul. 5, 2007 as U.S. Patent Publication No. 2007/0156124, the entireties of both of which are hereby incorporated by reference herein.

With continued reference to FIGS. 48 and 49, the skin treatment device 4210 can be conveniently designed to be secured to a user's hand H. The device 4210 can include one or more finger holes 4228 that are sized, shaped and otherwise adapted to receive one or more fingers of a user's hand. To help maintain the device 4210 along the user's hand and to generally help stabilize the device 4210 during use, the device 4210 can include one or more wings 4222, 4224 on either side of the finger holes 4228 or other finger receiving portion. Although the illustrated embodiment shows the user's middle finger positioned within the finger hole 4228, a device 4210 can be designed so that one or more other fingers are configured to be placed within a corresponding finger receiving portion of the device 4210, either in lieu of or in addition to the middle finger. The finger holes 4228 or other finger receiving portion can include one or more flexible materials (e.g., elastic fabric) that conveniently permit the device 4210 to be secured to users having varying finger sizes.

The embodiment illustrated in FIGS. 48 and 49 offers certain advantages. For example, such a configuration allows a user to conveniently secure the device to his or her hand during use without the need to grasp the device. This can facilitate the treatment process, while reducing fatigue to the user resulting from a prolonged treatment procedure. In addition, given its simplicity, the device 4210 can be easier and cheaper to manufacture.

As discussed herein, in any of the embodiments disclosed herein, or equivalents thereof, such as, for example, those discussed herein with reference to FIGS. 1-49, one or more materials can be strategically embedded, impregnated, placed, stored and/or otherwise disposed on one or more surfaces or areas of the tip or other portion or component of the skin treatment system. Such materials can comprise solids, semi-solids, other dried substances, gels, concentrated solutions and/or the like. For example, such materials can be provided in loose form (e.g., positioned on or within a recess, other portion of the tip, within a cartridge or other container, adhered to one or more surfaces, etc.), as a tablet, capsule, pill, disc or other dissolvable solid, saturated within a foam pad or other sponge-like material and/or the like. Thus, in certain arrangements, water (e.g., distilled, tap water, filtered, etc.), saline, other dilutants and/or other fluids which are delivered to the tip can selectively dissolve, liquefy, melt, soften, dilute or otherwise prepare the materials embedded, impregnated and/or otherwise positioned on the tip, within a cartridge or other container and/or on or within another portion or component of a skin treatment system (e.g., handpiece assembly, fluid line upstream of the handpiece assembly, etc.). Accordingly, the desired human growth factors, cytokines, soluble collagen, antioxidants, matrix proteins, serums, water, saline, other dilutants or dissolvents, vitamins, chemical exfoliation agents, lotions, soothing agents, brightening or lightening agents, peptides, acids, anesthetics, medicants, other non-active or active compounds, other fluids or materials, combination or mixtures thereof and/or any other substance can be advantageously provided to the skin surface being treated, as desired or required. Additional information regarding such embedded or impregnated materials is provided in U.S. patent application Ser. No. 12/362,353, filed Jan. 29, 2009, the entirety of which is hereby incorporated by reference herein and made a part of the present specification.

Some or all of the embodiments disclosed herein can be particularly useful for less expensive and/or simpler microdermabrasion systems. In some embodiments, such systems can target the home consumer market.

In any of the embodiments described and/or illustrated herein, or variations thereof, treatment fluids and/or other materials can be delivered to the tip of a handpiece assembly using one or more ways. For example, in some embodiments, serums or other substances can be delivered through a supply canister or fluid bottle. Such serums, compositions, other fluids or substances can be pre mixed so that they are delivered to the tip and the skin unmodified or substantially unmodified.

In other embodiments, serums, fluids, gels or other materials can be in the form of a pack container dry granular material, viscous gels and/or the like. Such packs can be mixed with water or some other fluid by a user to a desired concentration. In other embodiments, one or more treatment materials can be impregnated or otherwise embedded into the tips of the handpiece assemblies. Thus, such materials (e.g., powers, solids, gels, etc.) can advantageously dissolve when they contact water, saline or some other liquid. In still other embodiments, the treatment materials can be contained within a capsule, tablet or other enclosure. Such enclosures can be configured to dissolve when placed in water or some other fluid. Therefore, in some embodiments, a user may be required to place a capsule, the contents of a pack or some other materials into a canister and add water or other fluid before use.

In some embodiments, one or more serums or other substances can be delivered to the treatment surface of a handpiece assembly to treat a particular skin condition. For example, the system can be used to treat acne, dry or oily skin, fine lines, sun-damaged skin, other skin diseases or disorders and/or like.

In some embodiments, the serums, other materials and/or a combination of such serums or other materials can be utilized for the treatment of substantially most or all skin types. For example, such serums and/or other materials can be used when the handpiece assembly exfoliates skin.

In another embodiment, the serums, other materials and/or a combination of such serums or other materials can be used during a follow-up (e.g., secondary, tertiary, etc.) or finish treatment step. For example, such serums and/or other materials can be used to hydrate the skin and/or lighten treat skin damage, either in lieu of or in addition to exfoliating skin. In such embodiments, the serums and/or other materials can comprise anti-oxidants, hyaluronic acid and/or the like.

In yet other embodiments, the serums, other materials and/or a combination of such serums or other materials can be used to target acne or oily skin conditions. It will be appreciated that other serums, other materials and/or combinations of such serums or other materials can be used to target one or more types of skin conditions or treatments. Further, a particular treatment procedure can utilize one, two or more of such serums or other materials during various treatment phases (e.g., exfoliation, finish or polishing treatment, etc.).

In some embodiments, one or more kits can be developed that target a specific type of user, skin condition, desired result and/or the like. For example, such a kit can comprise serums and/or other materials that target teenage acne. As discussed, the serums and/or other materials contained in such kits can be in one or more different forms, such as, for example, liquids, gels, other fluids, powders, solids and/or the like. In some embodiments, such serums and/or other materials can be configured for immediate use. Alternatively, a particular amount of water, saline or other liquids, other dilution or dissolving agents and/or the like may need to be added to the serums and/or other materials to get them to a usable state.

In addition, depending on who the target user is (e.g., teenagers, adults, etc.) and/or how severe a particular condition is, the concentration or strength of the serums and/or other materials can be varied. For example, for younger users, a kit directed at acne treatment can comprise lower concentrations of serums and/or other materials. By way of another example, kits comprising higher concentrations or strengths of serums and/or other materials can be used to treat oily skin or acne in adults. In another embodiment, a kit can be developed to target users whose skin is generally typical (e.g., the users' skin is not abnormally dry or oily, the users do not have excessive amount of acne or scarring, etc.).

As discussed, the kits can include one, two or more different types of treatment combinations. For example, a kit can comprise a first combination of serum(s) and/or other material(s) that is intended to target the exfoliation of skin. The same kit may include a second treatment combination that can be used in a follow-up treatment to treat oily skin or the like. In other embodiments, however, a kit can comprise more or fewer treatment combinations, as desired or required by a particular skin treatment procedure.

According to certain arrangements, treatment materials that are provided to the skin interface during a dermabrasion procedure are configured to be released or otherwise made available to a user's skin over a pre-selected, relatively extended time period. Such time release materials can be provided in the form of microcapsules, other capsules or enclosures and/or the like.

Regardless of the form in which they are provided (e.g., within microcapsules or other enclosures), time-release products or materials can be delivered to a skin surface directly through a cartridge or other container. Such a cartridge can be positioned within a handpiece assembly, such as, for example, those illustrated in FIGS. 1-4C, 13A-16B and 18B herein. Cartridges or other containers containing such time-release materials can be provided in various locations of a handpiece assembly, including, without limitation, a recess of the main portion, underneath or near a removable tip and/or the like. In certain embodiments, a cartridge or other container containing one or more time-release materials is separate from the handpiece assembly. For example, as illustrated in FIG. 18A, such a cartridge or other container can be placed along a delivery line, which selectively supplies fluids and/or other materials through the cartridge to a handpiece assembly. In other arrangements, such as, for example, those illustrated in FIGS. 6B, 7, 17 and 20A-23B herein, time-release materials can be provided to the handpiece assembly from one or more upstream containers or other sources via a delivery line. By way of example, in accordance with the configuration depicted herein in FIGS. 7 and 17, time-release and/or other products and substances can be placed within one or more containers of a manifold system. Such materials can be subsequently delivered through a handpiece assembly using one or more conduits to the skin area being treated.

Figure 12C:
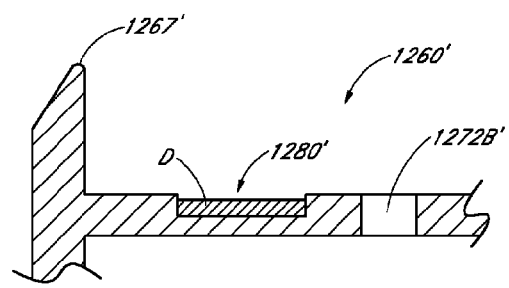
FIG. 12C illustrates a cross-sectional view of another embodiment of a tip comprising one or more recesses that are configured to selectively receive solids, gels and/or other materials.

In yet other arrangements, time-release materials are advantageously provided, either alone or in combination with one or more other substances, within a recess, cavity or other opening or a tip or other portion of a skin treatment system. For example, such recesses can be provided along a distal surface of the tip, as illustrated in FIGS. 12A-12C and discussed in greater detail herein. In certain embodiments, one or more time-release materials are embedded, impregnated, placed, stored and/or otherwise disposed on one or more surfaces or areas of the tip or other portion or component of the skin treatment system (e.g., the foam pads of FIG. 19A-20B). In one embodiment, such materials are impregnated onto a dissolvable strip or other member. Further, such time-release materials, which may be provided alone or in combination with any other materials, can comprise microcapsules, other capsules, solids, semi-solids, other dried substances, gels, concentrated solutions and/or the like. In some arrangements, time-release materials and/or other substances are provided in capsules (e.g., microcapsules), caps, loose form (e.g., positioned on or within a recess, other portion of the tip, within a cartridge or other container, adhered to one or more surfaces, etc.), as a tablet, pill, disc or other dissolvable solid, saturated within a foam pad or other sponge-like material and/or the like.

Thus, time-release materials can be provided in solid form (e.g., impregnated or otherwise disposed onto or near a tip of a handpiece assembly), as part of a solution being delivered to a handpiece assembly tip (e.g., in concentrated or un-concentrated form) and/or in any other form or manner. In some embodiments, regardless of how such materials (e.g., contained within capsules, microcapsules, other releasable enclosures or containers, etc.) delivered to a person's interface, they can be configured to release and become available to a skin surface at various times after delivery. Thus, by way of example, some capsules or enclosures can be configured to release their internal contents during an initial time frame, whereas other capsules or enclosure are adapted to release their internal contents at later time intervals. Consequently, the overall effective time period that the substances contained in such capsules or other enclosures can be extended. Therefore, the time-release microcapsules, capsules or other enclosures can be configured to release the media and/or other materials contained therein at time intervals that are offset from one another. In some arrangements, the time-release materials are released after a particular time exposure to a person's skin (e.g., in the presence of sweat, oil, etc.), air, heat, humidity, light, time and/or any other factor. In some arrangements, the offset time release of such materials can be accomplished by varying the thickness of the microcapsules or other enclosures.

Regardless of where the time-release materials are positioned relative to the handpiece assembly (e.g., within a cartridge or other container, within or outside of a handpiece assembly, in a recess or other opening of a tip or other portion of a handpiece assembly, within a foam pad, on a surface of a tip or other portion of a handpiece assembly, etc.), water (e.g., distilled, tap water, filtered, etc.), saline, other dilutants and/or other fluids can be used to selectively dissolve, liquefy, melt, soften, dilute or otherwise prepare the time-release and/or any other materials. Materials that can be included in such time-release capsules, microcapsules and/or any other enclosure include, but are not limited to, salicylic acid, other anti-acne materials, human growth factors, other types of growth factors, cytokines, soluble collagen, antioxidants, matrix proteins, peptides, amino acids, UVA and/or UVB sunblocks, other sunblocking agents, serums, vitamins, chemical exfoliation agents, lotions, soothing agents, skin brightening or lightening agents, skin tightening agents, acids, anesthetics, hyaluronic acid (HA), other hydration agents, hair removal or hair growth suppression agents, medicaments and pharmaceuticals, other non-active or active compounds, water, saline, other dilutants or dissolvents, other fluids or materials, combination or mixtures thereof and/or any other substance can be advantageously provided to the skin surface being treated, as desired or required.

According to certain embodiments, time-release materials include one or more active ingredients that target specific skin conditions or types. For instance, a time-release product used to help control skin acne can include salicylic acid. The salicylic acid can be provided alone or in combination with one or more other active and/or non-active ingredients (e.g., azelaic acid, topical retinoids, benzoyl peroxide, topical antibiotics, other anti-acne materials, saline, other dilutants or fluids, soaps, hardening agents, gels, other binders, lotions, moisturizers, etc.). In other embodiments, time release materials include one or more of the following, either alone or in combination with each other or another substance or material: salicylic acid, other anti-acne materials, human growth factors, other types of growth factors, cytokines, soluble collagen, antioxidants, matrix proteins, peptides, amino acids, UVA and/or UVB sunblocks, other sunblocking agents, serums, vitamins, chemical exfoliation agents, lotions, soothing agents, skin brightening or lightening agents, skin tightening agents, acids, anesthetics, hyaluronic acid (HA), other hydration agents, hair removal or hair growth suppression agents, medicaments and pharmaceuticals, other non-active or active compounds, water, saline, other dilutants or dissolvents, other fluids or materials.

Time-release salicylic acid capsules (e.g., microcapsules) and/or any other active or non-active ingredients included in a skin treatment material can be encapsulated within a solid binder, such as, for example, soap or gel. Thus, when water or another fluid is added to the material, the treatment material can at least partially dissolve, advantageously releasing capsules onto the skin surface. The capsules can be configured to release their internal contents at different time intervals after being deposited on or near a person's skin.

Alternatively, as discussed in greater detail herein, such microcapsules or other time-release materials can be provided within a cartridge, another container, a recess or other opening and/or the like. According to certain embodiments, the microcapsules or other time-release materials are included within a binder or are provided in loose form (e.g., as a solid, within a liquid, gel, other fluid or other medium, etc.). Thus, time-release materials can be selectively delivered to the skin (or be initially present at a tip-skin interface) in one or more different forms. Regardless of the exact manner in which they are provided to a person's skin, such time-release materials can help target certain skin ailments or conditions (e.g., acne, eczema, psoriasis, etc.), conditions (e.g., dry skin, oily skin, etc.) and/or the like.

In some embodiments, microcapsules and/or other time-release products delivered to the skin surface are configured to be released or otherwise become available to the skin at different times from each other. For example, microcapsules can be adapted to release salicylic acid and/or any other active or non-active ingredients contained therein in various time intervals (e.g., quarter-hour, half-hour, one-hour, two-hour, three-hour, etc.). Accordingly, the desired materials can be provided to a target skin surface to have an effect on such a surface over a longer period of time. This can facilitate a particular treatment procedure by effectively prolonging the overall treatment time-period. For example, in some embodiments, an acne treatment is more effective if salicylic acid is released over a targeted skin surface during a longer time period (e.g., less than 30 minutes, 1 hour, 2 hours, 4 hours, 6 hours, 8 hours, 10 hours, 12 hours, 24 hours, 36 hours, 48 hours, more than 48 hours, etc.).

In one embodiment, time-release materials are provided to a dermabrasion system which is adapted to treat skin having acne or another skin condition. A handpiece assembly having an abrasive distal end, such as, for example, a tip in accordance with any of the arrangements illustrated or otherwise disclosed herein, or equivalents thereof, can be used to treat a skin surface of a patient. As the tip is moved across the target skin area, exfoliated skin, infected waste and/or other materials can be advantageously removed. In addition, the treatment system can be configured to selectively deposit time-release product onto the treated skin before, after and/or contemporaneously with the exfoliation process. As discussed in greater detail herein, the time-release product can be delivered from a cartridge or other container located either within a handpiece assembly or separate from it. In some arrangements, water, saline and/or other dilutants are required to at least partially dissolve or otherwise release such substances (e.g., from a binder, gel, solid, etc.). Salicylic acid and/or any other materials contained within the time-release product (e.g., microcapsules, other capsules, caps, etc.) and/or other materials delivered to the patient's skin can be advantageously released over a longer time-period so as to help prevent or reduce the likelihood of bacterial infection, pain or discomfort, sensitivity to sunlight or other light sources and/or the like.

According to certain arrangements, time-release capsules or other materials containing salicylic acid and/or other skin solutions can be embedded on or near a surface of a tip using a binder. For example, glycerin soap or other base materials or hardening agents can be used to bind the time-release materials. As water, saline or other dilutants or fluids are selectively delivered to the bound materials, time-release materials can dissolve, allowing salicylic acid capsules to be released to a target area of the skin. In one configuration, the time-release materials comprise approximately 30% of the bound mixture by volume, while the soap or other base material and/or hardening agent comprises the remaining approximately 70%. In other embodiments, the volumetric ratio of time-release materials to base materials and hardening agents can be greater or less than 3:7, as required or desired (e.g., less than approximately 1:9, approximately 1:4, 2:3, 1:1, 3:2, 7:3, 4:1, more than approximately 4:1, etc.).

In any of the embodiments of a handpiece assembly disclosed herein, or equivalent thereof, one or more of the various treatment materials and/or other substances being conveyed to the skin surface can be selectively heated. Heating of fluids and/or other material streams to a desired temperature can help enhance one or more aspects of a skin treatment procedure. For example, in some arrangements, heated fluids and/or other materials are generally better absorbed into a skin surface, as the skin pores may be caused to open because of the elevated temperature. In other embodiments, heated fluids and other materials advantageously stimulate improved blood circulation along the skin surface (e.g., dermis). Further, heating of water, saline and/or other dilutants or dissolvents can help improve the manner in which solids, granulated materials, gels, concentrated fluids and/or other materials impregnated or otherwise positioned on a handpiece assembly dissolve, dilute and/or otherwise transform into the desired final product.

According to some embodiments, one or more heating devices or mechanisms are positioned within or on a handpiece assembly (e.g., the main body portion, the adjustable distal portion, the tip, etc.). In other configurations, heaters are positioned upstream of the handpiece assembly, such as, for example, on or within a cartridge or other container, a cartridge holder, fluid delivery lines and/or the like.

Fluid and/or other material streams being conveyed through a handpiece assembly can be heated conductively or convectively, as desired or required. Adequate heating devices or systems can include resistive heaters, other electrical heaters and/or the like. In other embodiments, heated air or other fluids can be used to thermally transfer heat to fluids and/or other materials being delivered through a handpiece assembly. In addition, such heaters can include one or more sensors, feedback loops, controllers and/or other components to help maintain the treatment materials being delivered to the skin surface at or near a desired temperature or within a desired range.

In some embodiments, one or more serums, salicylic acid, other anti-acne acids and materials, microcapsules, capsules, other time-release products and substances, other fluids and/or substances can be selectively delivered to or near a treatment surface of a handpiece assembly to help remedy a particular skin condition. For example, the system can be used to treat acne, dry or oily skin, fine lines, sun-damaged skin, other skin diseases or disorders and/or like. Further, the serums, other fluids, other materials and/or mixtures thereof can be customized to target a particular disorder, ailment, other treatable or chronic condition, skin type and/or the like.

In another embodiment, serums, medicants, other fluids, other materials, combinations thereof and/or the like are used during a follow-up step or procedure (e.g., secondary, tertiary, polishing, etc.) or post-treatment phase. For example, such materials and/or mixtures can be used to hydrate the skin and/or lighten treat skin damage, either in lieu of or in addition to exfoliating skin. In any such embodiments, the serums or other fluids or materials can comprise human growth factors, cytokines, soluble collagen, matrix proteins, other proteins, anti-oxidants, hyaluronic acid, medicants and/or the like.

According to certain configurations, the serums, other fluids, other materials and/or mixtures thereof are used to target acne, oily skin, dry skin, other skin types and/or other skin conditions, diseases or ailments. Further, a particular treatment procedure can utilize one, two or more of such serums, medicants and/or other fluids, materials or substances during various treatment phases (e.g., exfoliation, finish or polishing treatment, post-treatment, etc.).

One or more kits developed to target a specific type of user, skin condition, disease or ailment, desired result and/or the like can be provided to a user. For example, such a kit can comprise serums, salicylic acid, other anti-acne acids and materials, microcapsules, capsules, other time-release products and substances, medicants, other fluids, other materials, mixtures thereof and/or the like that target teenage acne. As discussed, the serums and/or other materials contained in such kits can be in one or more different forms, such as, for example, liquids, gels, other fluids, powders, dissolvable tablets or other packs, solids and/or the like. In some embodiments, such serums and/or other materials are configured for immediate use (e.g., by not requiring any dilution, premixing or other preparatory steps by a user). Alternatively, a particular amount of water, saline or other liquids, other dilution or dissolving agents and/or the like may need to be added to achieve a usable product. Kits can include one or more cartridges or other containers that are configured to be placed onto and removed from a handpiece assembly as discussed herein.

In addition, depending on who the target user is (e.g., teenagers, adults, etc.) and/or how severe a particular condition is, the concentration or strength of the serums, medicants, other fluids or materials, mixtures thereof and/or the like can be selectively varied. For example, for younger users, a kit directed at acne treatment can comprise lower concentrations of serums and/or other materials. According to another example, kits comprising higher concentrations or strengths of serums, medicants and/or other substances can be used to treat oily skin or acne in adults. In other arrangements, a kit targets users whose skin is generally normal or typical (e.g., the users' skin is not abnormally dry or oily, the users do not have excessive amount of acne or scarring, etc.).

As discussed, the kits can comprise one, two or more different types of medicants, other active or non-active agents, serums, other fluids, other materials, mixtures thereof and/or the like, as desired or required. For example, a kit can comprise a first combination of serum(s) and/or other material(s) that is intended to be used during a basic skin exfoliation procedure. Further, a kit may include a second treatment combination that is used in a follow-up treatment to treat oily skin, dry skin, another skin type, a skin disease or ailment, another skin condition and/or the like. However, a kit may comprise more or fewer treatment combinations, as desired or required by a particular skin treatment procedure.

The systems, apparatuses, devices and/or other articles disclosed herein may be formed through any suitable means. The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, it is not intended that the invention be limited, except as by the appended claims.

What is claimed is:

1. A device for treating a skin surface, comprising:
   a handpiece assembly comprising at least one delivery conduit; and
   a tip configured to be positioned along a distal end of the handpiece assembly, the tip being configured to contact the skin surface, wherein at least one time-release material is positioned along at least a portion of the tip;
   wherein the at least one delivery conduit is in fluid communication with at least one fluid source; and
   wherein the at least one fluid source is configured to at least partially dissolve the at least one time-release material positioned along the tip.

2. The device of claim 1, wherein the tip is removable from the handpiece assembly.

3. The device of claim 1, wherein the tip comprises at least one abrasive structure or element, wherein the at least one abrasive structure or element is configured to abrade skin tissue when the device is moved relative to skin surface.

4. The device of claim 3, wherein the at least one abrasive structure or element comprises a protruding member, a spiral ridge or an abrasive surface.

5. The device of claim 3, wherein the at least one abrasive structure or element comprises an abrasive disc configured to be separated from the tip.

6. The device of claim 1, wherein the at least one time-release material comprises a plurality of microcapsules, capsules or other enclosures configured to release their internal contents at various times following delivery to the skin surface.

7. The device of claim 1, wherein the at least one time-release material comprises salicylic acid.

8. The device of claim 1, wherein the at least one time-release material comprises a peptide, a growth factor, a sunblocking agent, an antioxidant, a hydration agent, a skin lightening agent or a skin tightening agent.

9. The device of claim 1, wherein the at least one time-release material is impregnated along at least a portion of the tip.

10. The device of claim 1, wherein the handpiece assembly comprises a recess configured to removably receive a cartridge, wherein an internal content of said cartridge is placed in fluid communication with the at least one delivery conduit when said cartridge is secured within the recess of the handpiece assembly.

11. The device of claim 10, wherein the cartridge comprises a movable piston therein, said movable piston configured to urge an internal content of the cartridge toward an outlet of the cartridge.

12. The device of claim 1, wherein the at least one fluid source comprises a container that is separate from the handpiece assembly, said container being in fluid communication with the at least one delivery conduit via a separate fluid conduit.

13. The device of claim 12, wherein the separate container is part of a larger manifold system.

14. A device for treating a skin surface, comprising:
    a handpiece assembly comprising at least one delivery conduit;
    a tip configured to be positioned along the distal end of the handpiece assembly, the tip being configured to contact the skin surface during a skin treatment procedure, wherein the tip comprises at least one time-release material, the at least one time-release material being configured to effectively prolong an overall time period of a skin treatment;

wherein the at least one delivery conduit is in fluid communication with at least one fluid source; and wherein the at least one fluid source comprises a diluting agent configured to at least partially dissolve the at least one time-release material located along the tip.

15. The device of claim 14, wherein the tip is removable from the handpiece assembly.

16. The device of claim 14, wherein the tip comprises at least one abrasive structure or element, wherein the at least one abrasive structure or element is configured to abrade skin tissue when the device is moved relative to skin surface.

17. The device of claim 16, wherein the at least one abrasive structure or element comprises a protruding member, a spiral ridge or an abrasive surface.

18. The device of claim 14, wherein the at least one time-release material comprises a peptide, a growth factor, a sunblocking agent, an antioxidant, a hydration agent, a skin lightening agent or a skin tightening agent.

19. The device of claim 14, wherein the at least one time-release material is impregnated along at least a portion of the tip.

20. The device of claim 14, wherein the at least one time-release material is located within a recess of the tip.

* * * * *